US010465239B2

(12) United States Patent
Li

(10) Patent No.: US 10,465,239 B2
(45) Date of Patent: *Nov. 5, 2019

(54) METHODS AND SYSTEMS FOR NUCLEIC ACID AMPLIFICATION

(71) Applicant: Coyote Bioscience Co., Ltd., Beijing (CN)

(72) Inventor: Xiang Li, Beijing (CN)

(73) Assignee: COYOTE BIOSCIENCE CO., LTD., Beijing (CN)

( * ) Notice: Subject to any disclaimer, the term of this patent is extended or adjusted under 35 U.S.C. 154(b) by 49 days.

This patent is subject to a terminal disclaimer.

(21) Appl. No.: 15/372,195

(22) Filed: Dec. 7, 2016

(65) Prior Publication Data

US 2017/0306375 A1   Oct. 26, 2017

Related U.S. Application Data

(63) Continuation of application No. 14/963,986, filed on Dec. 9, 2015, now Pat. No. 9,546,389, which is a continuation of application No. PCT/CN2014/094914, filed on Dec. 25, 2014, which is a continuation-in-part of application No. PCT/CN2013/090425, filed on Dec. 25, 2013.

(51) Int. Cl.
    *C12Q 1/686* (2018.01)
(52) U.S. Cl.
    CPC .................................. *C12Q 1/686* (2013.01)
(58) Field of Classification Search
    None
    See application file for complete search history.

(56) References Cited

U.S. PATENT DOCUMENTS

| 5,759,821 A | 6/1998 | Teasdale |
| 7,052,839 B2 | 5/2006 | Nelson et al. |
| 7,223,541 B2 | 5/2007 | Fuller et al. |
| 9,546,389 B2 | 1/2017 | Li et al. |
| 2003/0124576 A1 | 7/2003 | Kumar et al. |
| 2004/0209331 A1 | 10/2004 | Ririe |
| 2006/0054504 A1 | 3/2006 | Lee et al. |
| 2007/0072196 A1 | 3/2007 | Xu et al. |
| 2008/0085541 A1 | 4/2008 | Spangler |
| 2012/0308990 A1 | 12/2012 | Termaat et al. |
| 2013/0022963 A1 | 1/2013 | Exner et al. |
| 2018/0312913 A1 | 11/2018 | Li et al. |

FOREIGN PATENT DOCUMENTS

| CN | 1987446 A | 6/2007 |
| CN | 101597652 A | 12/2009 |
| CN | 102094002 A | 6/2011 |
| CN | 102174660 A | 9/2011 |
| CN | 102656448 A | 9/2012 |
| CN | 103074349 A | 5/2013 |
| CN | 103740832 A | 4/2014 |
| EP | 1069190 A2 | 1/2001 |
| GB | 2302590 A | 1/1997 |
| JP | 4186269 B2 | 11/2008 |
| JP | 2010536393 A | 12/2010 |
| JP | 2012034705 A | 2/2012 |
| WO | WO-2006082575 A1 | 8/2006 |
| WO | WO-2008002740 A2 | 1/2008 |
| WO | WO-2008144556 A1 | 11/2008 |
| WO | WO-2009094638 A2 | 7/2009 |
| WO | WO-2009156895 A1 | 12/2009 |
| WO | WO-2010002938 A2 | 1/2010 |
| WO | WO-2011121454 A2 | 10/2011 |
| WO | WO-2012109604 A1 | 8/2012 |
| WO | WO-2013006793 A2 | 1/2013 |
| WO | WO-2013006793 A3 | 5/2013 |
| WO | WO-2015096063 A1 | 7/2015 |
| WO | WO-2015096763 A1 | 7/2015 |
| WO | WO-2017088169 A1 | 6/2017 |
| WO | WO-2017088834 A1 | 6/2017 |

OTHER PUBLICATIONS

Qiagen Sensiscript Reverse Transcription Handbook. (Year: 2010).*
Qiagen Omniscript Reverse Transcription Handbook. (Year: 2010).*
Callahan, et al. Use of a portable real-time reverse transcriptase-polymerase chain reaction assay for rapid detection of foot-and-mouth disease virus. J Am Vet Med Assoc. Jun. 1, 2002;220(11):1636-42.
European search report and search opinion dated Jul. 3, 2017 for EP Application No. 14875135.7.
Gilbert, et al. Typing of bovine viral diarrhea viruses directly from blood of persistently infected cattle by multiplex PCR. J Clin Microbiol. Jun. 1999;37(6):2020-3.
International search report and written opinion dated Feb. 26, 2015 for PCT Application No. CN2014/094914.
International search report and written opinion dated Nov. 26, 2014 for PCT Application No. CN2013/090425.
Jing, et al. Amplification of deoxyribonucleic acid (DNA) fragment using two-step polymerase chain reaction (PCR). African Journal of Biotechnology 10.15 (2011): 2838-2843.
Kurata, et al. Reevaluation and reduction of a PCR bias caused by reannealing of templates. Applied and environmental microbiology 70.12 (2004): 7545-7549.
Lorenz, et al. Polymerase chain reaction: basic protocol plus troubleshooting and optimization strategies. Journal of visualized experiments: JoVE 63 (2012).
Notice of allowance dated Oct. 7, 2016 for U.S. Appl. No. 14/963,986.
Office action dated May 3, 2016 for U.S. Appl. No. 14/963,986.
Office action dated Sep. 15, 2016 for U.S. Appl. No. 14/963,986.

(Continued)

*Primary Examiner* — Samuel C Woolwine
(74) *Attorney, Agent, or Firm* — Wilson Sonsini Goodrich & Rosati

(57) ABSTRACT

The present disclosure provides methods and systems for amplifying nucleic acid samples. In some aspects, the methods and systems provided can be useful in conducting multiple nucleic acid amplification reactions in parallel. In some embodiments, methods and systems provided herein can be useful in conducting reverse transcription and DNA amplification in parallel. Moreover, in some aspects, the methods and systems described herein can be useful in analysis of nucleic acid samples. In some embodiments, methods and systems provided herein can be useful for conducting multiple series of primer extension reactions, which can aid in analysis of a nucleic acid sample.

23 Claims, 46 Drawing Sheets

(56) References Cited

OTHER PUBLICATIONS

Don, et al., 'Touchdown' PCR to circumvent spurious priming during gene amplification Nucleic Acids Research, 1991, 19(14):4008.
Fode-Vaughan, et al., Detection of Bacteria in Environmental Samples by Direct PCR without DNA Extraction, Biotechniques, Sep. 2001, vol. 31(3):598-607.
Foo, et al. Development of a thermostabilized, one-step, nested, tetraplex PCR assay for simultaneous identification and differentiation of *Entamoeba* species, *Entamoeba histolytica* and *Entamoeba dispar* from stool samples. J Med Microbiol. Sep. 2012;61(Pt 9):1219-25. doi: 10.1099/jmm.0.044552-0. Epub May 3, 2012.
Long et al. Evaluation of Application Performance for a New HBV-DNA Fluorescence Quantitative PCR Diagnostic Kit by Nucleic Acid Extraction-free Method, Clinical Medical & Engineering, May 31, 2011, 18(5):652-653.
Luo et al. Rapid method for hepatitis B virus DNA extraction from serum for quantitative PCR amplification, China Journal of Modern Medicine, Sep. 30, 2004, 14(18):124-126.
Lusi, et al. One-step nested PCR for detection of 2 LTR circles in PBMCs of HIV-1 infected patients with no detectable plasma HIV RNA. J Virol Methods. Apr. 2005;125(1):11-3. Epub Jan. 26, 2005.
Mohamed, et al., Experience from the development of a diagnostic single tube real-time PCR for human caliciviruses, Norovirus genogroups I and II, Journal of Virological Methods, Nov. 2005, 132:69-76.
"PCT/CN2015/095763 International Search Report and Written Opinion dated Aug. 31, 2016".
"PCT/CN2016/107443 International Search Report and Written Opinion dated Mar. 7, 2017".
Revello, et al. Prenatal diagnosis of rubella virus infection by direct detection and semiquantitation of viral RNA in clinical samples by reverse transcription-PCR. J Clin Microbiol. Mar. 1997;35(3):708-13.
"Tth Dna Polymerase, Manufactured by Roche Diagnostics Corporation, Available at www.roche-applied-science.com, Accessed on Mar. 15, 2018, 5 pages."

* cited by examiner

METHODS AND SYSTEMS FOR NUCLEIC ACID AMPLIFICATION

CROSS-REFERENCE

This application is a continuation of U.S. patent application Ser. No. 14/963,986, filed Dec. 9, 2015, which is a continuation of Patent Cooperation Treaty Application No. PCT/CN2014/09414, filed Dec. 25, 2014, which is a continuation-in-part of PCT/CN2013/090425, filed on Dec. 25, 2013, said application is incorporated herein by reference in its entirety for all purposes.

BACKGROUND

Nucleic acid amplification methods permit selected amplification and identification of nucleic acids of interest from a complex mixture, such as a biological sample. To detect a nucleic acid in a biological sample, the biological sample is typically processed to isolate nucleic acids from other components of the biological sample and other agents that may interfere with the nucleic acid and/or amplification. Following isolation of the nucleic acid of interest from the biological sample, the nucleic acid of interest can be amplified, via, for example, amplification methods known in the art, such as thermal cycling based approaches (e.g., polymerase chain reaction (PCR)). Following amplification of the nucleic acid of interest, the products of amplification can be detected and the results of detection interpreted by an end-user. The extraction of nucleic acid from a biological sample prior to amplification of the nucleic acid, however, can be time consuming, resulting in a reduced time efficiency for the process as a whole.

Point-of-care (POC) testing has the potential to improve the detection and management of infectious diseases in resource-limited settings with poor laboratory infrastructure, or in remote areas where there are delays in the receipt of laboratory results and potential complications to following up with patients. POC testing also could render state of the art health care facilities more capable of delivering sample-to-answer results to patients during a single visit. Inefficiencies in POC methods and devices, however, limit what can be achieved. For example, preparation of nucleic acids (e.g., of a pathogen) from complex sample types (e.g., biological samples) entails highly skilled personnel, in a dedicated laboratory space, to manually perform multiple processing steps and subsequent testing, with reporting of results often occurring hours or even days later.

Thus, there exists a need for rapid, accurate methods and devices for analyzing nucleic acids from complex sample types. Such methods and devices may be useful, for example, in realizing fast sample-to-answer detection and management of diseases detectable via their nucleic acid.

SUMMARY

The present disclosure provides methods and systems for efficient amplification of nucleic acids, such as RNA and DNA molecules. Amplified nucleic acid product can be detected rapidly and with good sensitivity.

In one aspect, the disclosure provides a method of amplifying a target ribonucleic acid (RNA) present in a biological sample obtained directly from a subject. In one embodiment, the method comprises: (a) providing a reaction vessel comprising the biological sample and reagents necessary for conducting reverse transcription amplification in parallel with deoxyribonucleic acid (DNA) amplification, the reagents comprising (i) a reverse transcriptase, (ii) a DNA polymerase, and (iii) a primer set for the target RNA, to obtain a reaction mixture; and (b) subjecting the reaction mixture in the reaction vessel to multiple cycles of a primer extension reaction to generate amplified DNA product that is indicative of the presence of the target RNA, each cycle comprising (i) incubating the reaction mixture at a denaturing temperature for a denaturing duration that is less than or equal to 60 seconds, followed by (ii) incubating the reaction mixture at an elongation temperature for an elongation duration that is less than or equal to 60 seconds, thereby amplifying the target RNA. In another embodiment, the method comprises: (a) receiving the biological sample that has been obtained from the subject; (b) providing a reaction vessel comprising the biological sample and reagents necessary for conducting reverse transcription amplification and optionally deoxyribonucleic acid (DNA) amplification, the reagents comprising (i) a reverse transcriptase and (ii) a primer set for the target RNA, to obtain a reaction mixture; (c) subjecting the reaction mixture to multiple cycles of a primer extension reaction to yield a detectable amount of amplified DNA product that is indicative of the presence of the target RNA in the biological sample; (d) detecting the amount of amplified DNA product of (c); and outputting information regarding the amount of amplified DNA product to a recipient, wherein an amount of time for completing (a)-(e) is less than or equal to about 30 minutes. In some embodiments, the amount of time is less than or equal to 20 minutes, less than or equal to 10 minutes, or less than or equal to 5 minutes.

In some embodiments, the reagents further comprise a reporter agent that yields a detectable signal indicative of the presence of the amplified DNA product. In some embodiments, the intensity of the detectable signal is proportional to the amount of the amplified DNA product or target RNA. In some embodiments, the reporter agent is a dye. In some embodiments, the primer set comprises one or more primers. In some embodiments, the primer set comprises a first primer to generate a strand that is complementary to the target RNA. In some embodiments, the primer set comprises a second primer to generate a strand that is complementary to a DNA product that is complementary to at least a portion of the target RNA. In some embodiments, the target RNA is viral RNA. In some embodiments, the viral RNA is pathogenic to the subject. In some embodiments, the viral RNA is selected from the group consisting of HIV I, HIV II, Ebola virus, Dengue virus, orthomyxoviruses, hepevirus, and/or hepatitis A, B, C (e.g., Armored RNA-HCV virus), D, and E viruses.

In some embodiments, the reaction vessel comprises a body and a cap. In some embodiments, the cap is removable. In some embodiments, the reaction vessel adopts a format of a pipette tip. In some embodiments, the reaction vessel is part of an array of reaction vessels. In some embodiments, the reaction vessel part of an array of reaction vessels is individually addressable by a fluid handling device. In some embodiments, the reaction vessel comprises two or more thermal zones. In some embodiments, the reaction vessel is sealed, optionally hermetically sealed.

In some embodiments, the denaturing temperature is from about 90° C. to 100° C., or from about 92° C. to 95° C. In some embodiments, the elongation temperature is from about 35° C. to 72° C., or from about 45° C. to 65° C. In some embodiments, the denaturing duration is less than or equal to 30 seconds. In some embodiments, the elongation duration is less than or equal to 30 seconds.

In some embodiments, the target RNA has not undergone concentration prior to providing a reaction vessel comprising the biological sample and reagents necessary for conducting reverse transcription amplification in parallel with deoxyribonucleic acid (DNA) amplification. In some embodiments, the biological sample has not undergone RNA extraction when providing a reaction vessel comprising the biological sample and reagents necessary for conducting reverse transcription amplification in parallel with deoxyribonucleic acid (DNA) amplification. In some embodiments, the method further comprises the step of adding a lysis agent to the reaction vessel prior to or during providing a reaction vessel comprising the biological sample and reagents necessary for conducting reverse transcription amplification in parallel with deoxyribonucleic acid (DNA) amplification. In some embodiments, the lysis agent comprises a buffer. In some embodiments, the target RNA is released from the biological sample during one or more cycles of the primer extension reaction.

In some embodiments, the biological sample is a biological fluid from the subject. In some embodiments, the biological sample is selected from the group consisting of breath, blood, urine, feces, saliva, cerebrospinal fluid and sweat.

In some embodiments, DNA amplification is via the polymerase chain reaction. In some embodiments, the polymerase chain reaction is nested polymerase chain reaction. In some embodiments, DNA amplification is linear amplification. In some embodiments, the amplifying yields a detectable amount of DNA product indicative of the presence of the target RNA in the biological sample at a cycle threshold value (Ct) of less than 50, less than 40, less than 30, less than 20, less than 10, or less than 5. In some embodiments, the amplifying yields a detectable amount of DNA product indicative to the presence of the target RNA in the biological sample at a time period of 30 minutes or less, 20 minutes or less, or 10 minutes or less. In some embodiments, the amplifying is non-emulsion based.

In some embodiments, the recipient is a treating physician, a pharmaceutical company, or the subject. In some embodiments, subjecting the reaction mixture to multiple cycles of a primer extension reaction to yield a detectable amount of amplified DNA product that is indicative of the presence of the target RNA in the biological sample is conducted in 30 cycles or less, 20 cycles or less, or 10 cycles or less. In some embodiments, detecting is optically detecting, electrostatically detecting, or electrochemically detecting. In some embodiments, the method comprises providing a reaction vessel comprising the biological sample and reagents necessary for conducting reverse transcription amplification and deoxyribonucleic acid (DNA) amplification.

In some embodiments, the information is outputted as a report. In some embodiments, the report is an electronic report. In some embodiments, the information is outputted to an electronic display.

In another aspect, the disclosure provides a method of amplifying a target nucleic acid present in a biological sample obtained from a subject. The method comprises: (a) providing a reaction vessel comprising the biological sample and reagents necessary for conducting nucleic acid amplification, the reagents comprising (i) a deoxyribonucleic acid (DNA) polymerase and optionally a reverse transcriptase, and (ii) a primer set for the target nucleic acid, to obtain a reaction mixture; and (b) subjecting the reaction mixture in the reaction vessel to a plurality of series of primer extension reactions to generate amplified product that is indicative of the presence of the target nucleic acid in the biological sample, each series comprising two or more cycles of (i) incubating the reaction mixture under a denaturing condition characterized by a denaturing temperature and a denaturing duration, followed by (ii) incubating the reaction mixture under an elongation condition characterized by an elongation temperature and an elongation duration, wherein an individual series differs from at least one other individual series of the plurality with respect to the denaturing condition and/or the elongation condition.

In some embodiments, the target nucleic acid is a ribonucleic acid. In some embodiments, the reagents are necessary for conducting reverse transcription amplification in parallel with deoxyribonucleic acid amplification. In some embodiments, the amplified product is amplified deoxyribonucleic acid product. In some embodiments, the biological sample is not purified in (a). In some embodiments, the method further comprises subjecting the target nucleic acid to one or more denaturing conditions prior to (b). In some embodiments, the one or more denaturing conditions are selected from a denaturing temperature profile and a denaturing agent.

In some embodiments, the biological sample is diluted. This may aid in minimizing inhibitions. In some embodiments, the biological sample is concentrated. This may aid in increasing or otherwise improving sensitivity.

In some embodiments, the method further comprises subjecting the target nucleic acid to one or more denaturing conditions between a first series and a second series of the plurality of series of primer extension reactions. In some embodiments, the individual series differ with respect to at least any one, at least any two, at least any three, or at least any four of ramping rate between denaturing temperature and elongation temperature, denaturing temperature, denaturing duration, elongation temperature and elongation duration. In some embodiments, the individual series differ with respect to ramping rate between denaturing temperature and elongation temperature, denaturing temperature, denaturing duration, elongation temperature and elongation duration.

In some embodiments, the plurality of series of primer extension reactions comprises a first series and a second series, the first series comprising more than ten cycles, each cycle of the first series comprising (i) incubating the reaction mixture at about 92° C.-95° C. for no more than 30 seconds, followed by (ii) incubating the reaction mixture at about 35° C.-65° C. for no more than 1 minute, the second series comprising more than ten cycles, each cycle of the second series comprising (i) incubating the reaction mixture at about 92° C.-95° C. for no more than 30 seconds, followed by (ii) incubating the reaction mixture at about 40° C.-60° C. for no more than 1 minute.

In some embodiments, the plurality of series of primer extension reactions yields a detectable amount of amplified product that is indicative of the presence of the target nucleic acid in the biological sample with a lower cycle threshold value as compared to a single series of primer extension reactions under comparable denaturing and elongation conditions. In some embodiments, the method further comprises, prior to (b), pre-heating the biological sample at a pre-heating temperature from 90° C. to 100° C. for a pre-heating duration of no more than 10 minutes, 2 minutes, or 1 minute. In some embodiments, the pre-heating temperature is from 92° C. to 95° C. In some embodiments, the pre-heating duration is no more than about 30 seconds.

In another aspect, the disclosure provides a system for amplifying a target ribonucleic acid (RNA) present in a biological sample obtained directly from a subject. In one embodiment, the systems comprises: (a) an input module that receives a user request to amplify the target RNA in the biological sample; (b) an amplification module that, in response to the user request: receives, in a reaction vessel, a reaction mixture comprising the biological sample and reagents necessary for conducting reverse transcription amplification in parallel with deoxyribonucleic acid (DNA) amplification, the reagents comprising (i) a reverse transcriptase, (ii) a DNA polymerase, and (iii) a primer set for the target RNA; and subjects the reaction mixture in the reaction vessel to multiple cycles of a primer extension reaction to generate amplified DNA product that is indicative of the presence of the target RNA, each cycle comprising (i) incubating the reaction mixture at a denaturing temperature for a denaturing duration that is less than or equal to 60 seconds, followed by (ii) incubating the reaction mixture at an elongation temperature for an elongation duration that is less than or equal to 60 seconds, thereby amplifying the target RNA; and (c) an output module operatively coupled to the amplification module, wherein the output module outputs information regarding the target RNA or the DNA product to a recipient.

In another embodiment, the system comprises (a) an input module that receives a user request to amplify the target RNA in the biological sample; (b) an amplification module that, in response to the user request: (i) receives, in a reaction vessel, a reaction mixture comprising the biological sample that has been obtained from the subject and reagents necessary for conducting reverse transcription amplification and optionally deoxyribonucleic acid (DNA) amplification, the reagents comprising (1) a reverse transcriptase and (2) a primer set for the target RNA; and (ii) subjects the reaction mixture to multiple cycles of a primer extension reaction to yield a detectable amount of amplified DNA product that is indicative of the presence of the target RNA in the biological sample; (iii) detects the amount of amplified DNA product of (iii); and (iv) outputs information regarding the amount of amplified DNA product to a recipient, wherein an amount of time for completing (i)-(iv) is less than or equal to about 30 minutes; and (c) an output module operatively coupled to the amplification module, wherein the output module transmits the information to a recipient. In some embodiments, the output module is an electronic display. In some embodiments, the electronic display comprises a user interface. In some embodiments, the output module is a communication interface operatively coupled to a computer network.

In another aspect, the disclosure provides a system for amplifying a target nucleic acid present in a biological sample obtained from a subject. The system comprises: (a) an input module that receives a user request to amplify the target nucleic acid in the biological sample; (b) an amplification module that, in response to the user request: receives, in a reaction vessel, a reaction mixture comprising the biological sample and reagents necessary for conducting nucleic acid amplification, the reagents comprising (i) a DNA polymerase and optionally a reverse transcriptase, and (ii) a primer set for the target nucleic acid; and subjects the reaction mixture in the reaction vessel to a plurality of series of primer extension reactions to generate amplified product that is indicative of the presence of the target nucleic acid in the biological sample, each series comprising two or more cycles of (i) incubating the reaction mixture under a denaturing condition characterized by a denaturing temperature and a denaturing duration, followed by (ii) incubating the reaction mixture under an elongation condition characterized by an elongation temperature and an elongation duration, wherein an individual series differs from at least one other individual series of the plurality with respect to the denaturing condition and/or the elongation condition; and (c) an output module operatively coupled to the amplification module, wherein the output module outputs information regarding the nucleic acid or the amplified product to a recipient.

In another aspect, the disclosure provides a computer readable medium comprising machine executable code that, upon execution by one or more computer processors, implements a method of amplifying a target ribonucleic acid (RNA) present in a biological sample obtained directly from a subject. In one embodiment, the method comprises: (a) providing a reaction vessel comprising the biological sample and reagents necessary for conducting reverse transcription amplification in parallel with deoxyribonucleic acid (DNA) amplification, the reagents comprising (i) a reverse transcriptase, (ii) a DNA polymerase, and (iii) a primer set for the target RNA, to obtain a reaction mixture; and (b) subjecting the reaction mixture in the reaction vessel to multiple cycles of a primer extension reaction to generate amplified DNA product that is indicative of the presence of the target RNA, each cycle comprising (i) incubating the reaction mixture at a denaturing temperature for a denaturing duration that is less than or equal to 60 seconds, followed by (ii) incubating the reaction mixture at an elongation temperature for an elongation duration that is less than or equal to 60 seconds, thereby amplifying the target RNA.

In another embodiment, the method comprises: (a) receiving the biological sample that has been obtained from the subject; (b) providing a reaction vessel comprising the biological sample and reagents necessary for conducting reverse transcription amplification and optionally deoxyribonucleic acid (DNA) amplification, the reagents comprising (i) a reverse transcriptase and (ii) a primer set for the target RNA, to obtain a reaction mixture; (c) subjecting the reaction mixture to multiple cycles of a primer extension reaction to yield a detectable amount of amplified DNA product that is indicative of the presence of the target RNA in the biological sample; (d) detecting the amount of DNA product of (c); and (e) outputting information regarding the amount of DNA product to a recipient, wherein an amount of time for completing (a)-(e) is less than or equal to about 30 minutes.

In another aspect, the disclosure provides a computer readable medium comprising machine executable code that, upon execution by one or more computer processors, implements a method of amplifying a target nucleic acid present in a biological sample obtained from a subject. In one embodiment, the method comprises (a) providing a reaction vessel comprising the biological sample and reagents necessary for conducting nucleic acid amplification, the reagents comprising (i) a DNA polymerase and optionally a reverse transcriptase, and (ii) a primer set for the target nucleic acid, to obtain a reaction mixture; and (b) subjecting the reaction mixture in the reaction vessel to a plurality of series of primer extension reactions to generate amplified product from the target nucleic acid, each series comprising two or more cycles of (i) incubating the reaction mixture under a denaturing condition characterized by a denaturing temperature and a denaturing duration, followed by (ii) incubating the reaction mixture under an elongation condition characterized by an elongation temperature and an elongation duration, wherein an individual series differs from at least one other individual series of the plurality with respect to the denaturing condition and/or the elongation condition.

An additional aspect of the disclosure provides a system for amplifying a target nucleic acid in a biological sample obtained from a subject. The system can comprise an electronic display screen that comprises a user interface that displays a graphical element that is accessible by a user to execute an amplification protocol to amplify the target nucleic acid in the biological sample. The system can also comprise a computer processor coupled to the electronic display screen and programmed to execute the amplification protocol upon selection of the graphical element by the user. The amplification protocol can comprise subjecting a reaction mixture comprising the biological sample and reagents necessary for conducting nucleic acid amplification to a plurality of series of primer extension reactions to generate amplified product that is indicative of the presence of the target nucleic acid in the biological sample. Each series of primer extension reactions can include two or more cycles of incubating the reaction mixture under a denaturing condition characterized by a denaturing temperature and a denaturing duration, followed by incubating the reaction mixture under an elongation condition characterized by an elongation temperature and an elongation duration. An individual series may differ from at least one other individual series of the plurality with respect to the denaturing condition and/or the elongation condition.

In some embodiments, the amplification protocol can further comprise selecting a primer set for the target nucleic acid. In some embodiments, the reagents may comprise a deoxyribonucleic acid (DNA) polymerase, an optional reverse transcriptase, and a primer set for the target nucleic acid. In some embodiments, the user interface can display a plurality of graphical elements. Each of the graphical elements can be associated with a given amplification protocol among a plurality of amplification protocols. In some embodiments, each of the graphical elements may be associated with a disease. A given amplification protocol among the plurality of amplification protocols can be directed to assaying a presence of the disease in the subject. In some embodiments, the disease may be associated with a virus such as for example an RNA virus or a DNA virus. In some embodiments, the virus can be selected from the group consisting of human immunodeficiency virus I (HIV I), human immunodeficiency virus II (HIV II), an orthomyxovirus, Ebola virus, Dengue virus, influenza viruses, hepevirus, hepatitis A virus, hepatitis B virus, hepatitis C virus, hepatitis D virus, hepatitis E virus, hepatitis G virus, Epstein-Barr virus, mononucleosis virus, cytomegalovirus, SARS virus, West Nile Fever virus, polio virus, measles virus, herpes simplex virus, smallpox virus, adenovirus, and Varicella virus. In some embodiments, the influenza virus can be selected from the group consisting of H1N1 virus, H3N2 virus, H7N9 virus and H5N1 virus. In some embodiments, the adenovirus may be adenovirus type 55 (ADV55) or adenovirus type 7 (ADV7). In some embodiments, the hepatitis C virus may be armored RNA-hepatitis C virus (RNA-HCV). In some embodiments, the disease may be associated with a pathogenic bacterium (e.g., *Mycobacterium tuberculosis*) or a pathogenic protozoan (e.g., *Plasmodium*).

In some embodiments, the target nucleic acid may be associated with a disease. In some embodiments, the amplification protocol can be directed to assaying a presence of the disease based on a presence of the amplified product. In some embodiments, the disease may be associated with a virus such as, for example, an RNA virus or a DNA virus. In some embodiments, the virus can be selected from the group consisting of human immunodeficiency virus I (HIV I), human immunodeficiency virus II (HIV II), an orthomyxovirus, Ebola virus, Dengue virus, influenza viruses, hepevirus, hepatitis A virus, hepatitis B virus, hepatitis C virus, hepatitis D virus, hepatitis E virus, hepatitis G virus, Epstein-Barr virus, mononucleosis virus, cytomegalovirus, SARS virus, West Nile Fever virus, polio virus, measles virus, herpes simplex virus, smallpox virus, adenovirus, and Varicella virus. In some embodiments, the influenza virus can be selected from the group consisting of H1N1 virus, H3N2 virus, H7N9 virus and H5N1 virus. In some embodiments, the adenovirus may be adenovirus type 55 (ADV55) or adenovirus type 7 (ADV7). In some embodiments, the hepatitis C virus may be armored RNA-hepatitis C virus (RNA-HCV). In some embodiments, the disease may be associated with a pathogenic bacterium (e.g., *Mycobacterium tuberculosis*) or a pathogenic protozoan (e.g., *Plasmodium*).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "Fig." herein), of which:

DETAILED DESCRIPTION

Figure 1:
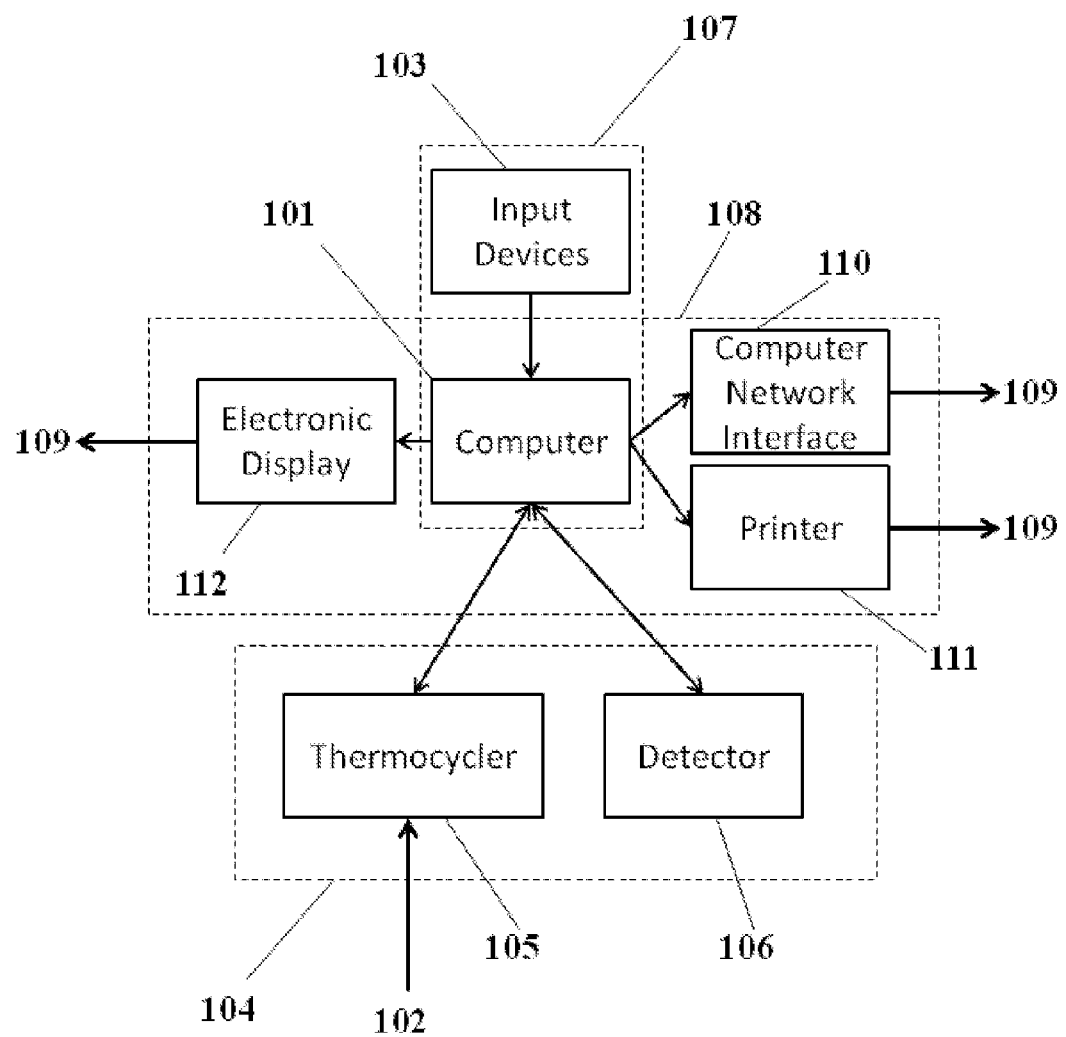
FIG. 1 is schematic depicting an example system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an" and "the" include plural references unless the context clearly dictates otherwise. For example, the term "a cell" includes a plurality of cells, including mixtures thereof.

As used herein, the terms "amplifying" and "amplification" are used interchangeably and generally refer to generating one or more copies or "amplified product" of a nucleic acid. The term "DNA amplification" generally refers to generating one or more copies of a DNA molecule or "amplified DNA product". The term "reverse transcription amplification" generally refers to the generation of deoxyribonucleic acid (DNA) from a ribonucleic acid (RNA) template via the action of a reverse transcriptase.

As used herein, the term "cycle threshold" or "Ct" generally refers to the cycle during thermocycling in which an increase in a detectable signal due to amplified product reaches a statistically significant level above background signal.

As used herein, the terms "denaturing" and "denaturation" are used interchangeably and generally refer to the full or partial unwinding of the helical structure of a double-stranded nucleic acid, and in some cases the unwinding of the secondary structure of a single stranded nucleic acid. Denaturation may include the inactivation of the cell wall(s) of a pathogen or the shell of a virus, and the inactivation of the protein(s) of inhibitors. Conditions at which denaturation may occur include a "denaturation temperature" that generally refers to a temperature at which denaturation is permitted to occur and a "denaturation duration" that generally refers to an amount of time allotted for denaturation to occur.

As used herein, the term "elongation" generally refers to the incorporation of nucleotides to a nucleic acid in a template directed fashion. Elongation may occur via the aid of an enzyme, such as, for example, a polymerase or reverse transcriptase. Conditions at which elongation may occur include an "elongation temperature" that generally refers to a temperature at which elongation is permitted to occur and an "elongation duration" that generally refers to an amount of time allotted for elongation to occur.

As used herein, the term "nucleic acid" generally refers to a polymeric form of nucleotides of any length, either deoxyribonucleotides (dNTPs) or ribonucleotides (rNTPs), or analogs thereof. Nucleic acids may have any three dimensional structure, and may perform any function, known or unknown. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non nucleotide components. A nucleic acid may be further modified after polymerization, such as by conjugation or binding with a reporter agent.

As used herein, the term "primer extension reaction" generally refers to the denaturing of a double-stranded nucleic acid, binding of a primer to one or both strands of the denatured nucleic acid, followed by elongation of the primer(s).

As used herein, the term "reaction mixture" generally refers to a composition comprising reagents necessary to complete nucleic acid amplification (e.g., DNA amplification, RNA amplification), with non-limiting examples of such reagents that include primer sets having specificity for target RNA or target DNA, DNA produced from reverse transcription of RNA, a DNA polymerase, a reverse transcriptase (e.g., for reverse transcription of RNA), suitable buffers (including zwitterionic buffers), co-factors (e.g., divalent and monovalent cations), dNTPs, and other enzymes (e.g., uracil-DNA glycosylase (UNG)), etc). In some cases, reaction mixtures can also comprise one or more reporter agents.

As used herein, a "reporter agent" generally refers to a composition that yields a detectable signal, the presence or absence of which can be used to detect the presence of amplified product.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogues thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the term "subject," generally refers to an entity or a medium that has testable or detectable genetic information. A subject can be a person or individual. A subject can be a vertebrate, such as, for example, a mammal. Non-limiting examples of mammals include murines, simians, humans, farm animals, sport animals, and pets. Other examples of subjects include food, plant, soil, and water.

In one aspect, the disclosure provides a method of amplifying a target ribonucleic acid (RNA) present in a biological sample obtained directly from a subject. The method comprises: (a) providing a reaction vessel comprising the biological sample and reagents necessary for conducting reverse transcription amplification in parallel with deoxyribonucleic acid (DNA) amplification, the reagents comprising (i) a reverse transcriptase, (ii) a DNA polymerase, and (iii) a primer set for the target RNA, to obtain a reaction mixture; and (b) subjecting the reaction mixture in the reaction vessel to multiple cycles of a primer extension reaction to generate amplified DNA product that is indicative of the presence of the target RNA, each cycle comprising (i) incubating the reaction mixture at a denaturing temperature for a denaturing duration that is less than or equal to 60 seconds, followed by (ii) incubating the reaction mixture at an elongation temperature for an elongation duration that is less than or equal to 60 seconds, thereby amplifying the target RNA.

In another aspect, the disclosure provides a method of amplifying a target ribonucleic acid (RNA) present in a biological sample obtained directly from a subject. The method comprises: (a) receiving the biological sample that has been obtained from the subject; (b) providing a reaction vessel comprising the biological sample and reagents necessary for conducting reverse transcription amplification and optionally deoxyribonucleic acid (DNA) amplification, the reagents comprising (i) a reverse transcriptase and (ii) a primer set for the target RNA, to obtain a reaction mixture; (c) subjecting the reaction mixture to multiple cycles of a primer extension reaction to yield a detectable amount of amplified DNA product that is indicative of the presence of the target RNA in the biological sample; (d) detecting the amount of amplified DNA product of (c); and (e) outputting information regarding the amount of amplified DNA product to a recipient, wherein an amount of time for completing (a)-(e) is less than or equal to about 30 minutes.

In one aspect, the disclosure provides a method of amplifying a target nucleic acid present in a biological sample obtained from a subject. The method comprises: (a) providing a reaction vessel comprising the biological sample and reagents necessary for conducting nucleic acid amplification, the reagents comprising (i) a deoxyribonucleic acid (DNA) polymerase and optionally a reverse transcriptase, and (ii) a primer set for the target nucleic acid, to obtain a reaction mixture; and (b) subjecting the reaction mixture in the reaction vessel to a plurality of series of primer extension reactions to generate amplified product that is indicative of the presence of the target nucleic acid in the biological sample, each series comprising two or more cycles of (i) incubating the reaction mixture under a denaturing condition characterized by a denaturing temperature and a denaturing duration, followed by (ii) incubating the reaction mixture under an elongation condition characterized by an elongation temperature and an elongation duration, wherein an individual series differs from at least one other individual series of the plurality with respect to the denaturing condition and/or the elongation condition.

In any of the various aspects, nucleic acid from a biological sample obtained from a subject is amplified. In some cases, the biological sample is obtained directly from the subject. A biological sample obtained directly from a subject generally refers to a biological sample that has not been further processed after being obtained from the subject, with the exception of any means used to collect the biological sample from the subject for further processing. For example, blood is obtained directly from a subject by accessing the subject's circulatory system, removing the blood from the subject (e.g., via a needle), and entering the removed blood into a receptacle. The receptacle may comprise reagents (e.g., anti-coagulants) such that the blood sample is useful for further analysis. In another example, a swab may be used to access epithelial cells on an oropharyngeal surface of the subject. After obtaining the biological sample from the subject, the swab containing the biological sample can be contacted with a fluid (e.g., a buffer) to collect the biological fluid from the swab.

In some embodiments, a biological sample has not been purified when provided in a reaction vessel. In some embodiments, the nucleic acid of a biological sample has not been extracted when the biological sample is provided to a reaction vessel. For example, the RNA or DNA in a biological sample may not be extracted from the biological sample when providing the biological sample to a reaction vessel. Moreover, in some embodiments, a target nucleic acid (e.g., a target RNA or target DNA) present in a biological sample may not be concentrated prior to providing the biological sample to a reaction vessel.

Any suitable biological sample that comprises nucleic acid may be obtained from a subject. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues.

A biological sample may be obtained from a subject by any means known in the art. Non-limiting examples of means to obtain a biological sample directly from a subject include accessing the circulatory system (e.g., intravenously or intra-arterially via a syringe or other needle), collecting a secreted biological sample (e.g., feces, urine, sputum, saliva, etc.), surgically (e.g., biopsy), swabbing (e.g., buccal swab, oropharyngeal swab), pipetting, and breathing. Moreover, a biological sample may be obtained from any anatomical part of a subject where a desired biological sample is located.

In any of the various aspects, a target nucleic acid is amplified to generate an amplified product. A target nucleic acid may be a target RNA or a target DNA. In cases where the target nucleic acid is a target RNA, the target RNA may be any type of RNA, including types of RNA described elsewhere herein. In some embodiments, the target RNA is viral RNA. In some embodiments, the viral RNA may be pathogenic to the subject. Non-limiting examples of pathogenic viral RNA include human immunodeficiency virus I (HIV I), human immunodeficiency virus II (HIV II), orthomyxoviruses, Ebola virus, Dengue virus, influenza viruses (e.g., H1N1, H3N2, H7N9, or H5N1), hepesvirus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

In cases where the target nucleic acid is a target DNA, the target DNA may be any type of DNA, including types of DNA described elsewhere herein. In some embodiments, the target DNA is viral DNA. In some embodiments, the viral DNA may be pathogenic to the subject. Non-limiting examples of DNA viruses include herpes simplex virus, smallpox, adenovirus (e.g., Adenovirus Type 55, Adenovirus Type 7) and Varicella virus (e.g., chickenpox). In some cases, a target DNA may be a bacterial DNA. The bacterial DNA may be from a bacterium pathogenic to the subject such as, for example, *Mycobacterium tuberculosis*—a bacterium known to cause tuberculosis. In some cases, a target DNA may be a DNA from a pathogenic protozoan, such as, for example one or more protozoans of the *Plasmodium* type that can cause Malaria.

In any of the various aspects of the present disclosure, a biological sample obtained from a subject is provided with reagents necessary for nucleic acid amplification in a reaction vessel to obtain a reaction mixture. Any suitable reaction vessel may be used. In some embodiments, a reaction vessel comprises a body that can include an interior surface, an exterior surface, an open end, and an opposing closed end. In some embodiments, a reaction vessel may comprise a cap. The cap may be configured to contact the body at its open end, such that when contact is made the open end of the reaction vessel is closed. In some cases, the cap is permanently associated with the reaction vessel such that it remains attached to the reaction vessel in open and closed configurations. In some cases, the cap is removable, such that when the reaction vessel is open, the cap is separated from the reaction vessel. In some embodiments, a reaction vessel may be sealed, optionally hermetically sealed.

A reaction vessel may be of varied size, shape, weight, and configuration. In some examples, a reaction vessel may be round or oval tubular shaped. In some embodiments, a reaction vessel may be rectangular, square, diamond, circular, elliptical, or triangular shaped. A reaction vessel may be regularly shaped or irregularly shaped. In some embodiments, the closed end of a reaction vessel may have a tapered, rounded, or flat surface. Non-limiting examples of types of a reaction vessel include a tube, a well, a capillary tube, a cartridge, a cuvette, a centrifuge tube, or a pipette tip. Reaction vessels may be constructed of any suitable material with non-limiting examples of such materials that include glasses, metals, plastics, and combinations thereof.

In some embodiments, a reaction vessel is part of an array of reaction vessels. An array of reaction vessels may be particularly useful for automating methods and/or simultaneously processing multiple samples. For example, a reaction vessel may be a well of a microwell plate comprised of a number of wells. In another example, a reaction vessel may be held in a well of a thermal block of a thermocycler, wherein the block of the thermal cycle comprises multiple wells each capable of receiving a sample vessel. An array comprised of reaction vessels may comprise any appropriate number of reaction vessels. For example, an array may comprise at least 2, 4, 6, 8, 10, 12, 14, 16, 18, 20, 25, 35, 48, 96, 144, 384, or more reaction vessels. A reaction vessel part of an array of reaction vessels may also be individually addressable by a fluid handling device, such that the fluid handling device can correctly identify a reaction vessel and dispense appropriate fluid materials into the reaction vessel. Fluid handling devices may be useful in automating the addition of fluid materials to reaction vessels.

In some embodiments, a reaction vessel may comprise multiple thermal zones. Thermal zones within a reaction vessel may be achieved by exposing different regions of the reaction vessel to different temperature cycling conditions. For example, a reaction vessel may comprise an upper thermal zone and a lower thermal zone. The upper thermal zone may be capable of a receiving a biological sample and reagents necessary to obtain a reaction mixture for nucleic acid amplification. The reaction mixture can then be subjected to a first thermocycling protocol. After a desired number of cycles, for example, the reaction mixture can slowly, but continuously leak from the upper thermal zone to the lower thermal zone. In the lower thermal zone, the reaction mixture is then subjected to a desired number of cycles of a second thermocycling protocol different from that in the upper thermal zone. Such a strategy may be particularly useful when nested PCR is used to amplify DNA. In some embodiments, thermal zones may be created within a reaction vessel with the aid of thermal sensitive layering materials within the reaction vessels. In such cases, heating of the thermal sensitive layering materials may be used to release reaction mixtures from one thermal zone to the next. In some embodiments, the reaction vessel comprises 2, 3, 4, 5, 6, 7, 8, 9, 10, 11, 12, 13, 14, 15 or more thermal zones.

In some embodiments, a reaction vessel comprising thermal zones may be used for processing of a biological sample prior to nucleic acid amplification. For example, a lysis agent may be added to a first thermal zone of a reaction vessel prior to adding a biological sample and reagents necessary for nucleic acid amplification. When the biological sample and reagents are added to the reaction vessel comprising the lysis agent, a reaction mixture capable of lysing species (e.g., cells or viral particles) within the biological is obtained. Alternatively, a lysis agent can be added to the first thermal zone of the reaction mixture concurrently with the biological sample and reagents. Subjecting the first thermal zone to temperature conditions suitable for action of the lysis agent may be used to lyse cells and viral particles in the biological sample in the first thermal zone, such that nucleic acids in the biological sample are released into the reaction mixture. After lysis, the reaction mixture can then be permitted to enter a second thermal zone of the reaction vessel for amplification of the released nucleic acid, using amplification methods described herein.

In cases where a lysis agent is desired, any suitable lysis agent known in the art may be used, including commercially available lysis agents. Non-limiting examples of lysis agents include Tris-HCl, EDTA, detergents (e.g., Triton X-100, SDS), lysozyme, glucolase, proteinase E, viral endolysins, exolysins zymolose, lyticase, proteinase K, endolysins and exolysins from bacteriophages, endolysins from bacteriophage PM2, endolysins from the *B. subtilis* bacteriophage PBSX, endolysins from *Lactobacillus* prophages Lj928, Lj965, bacteriophage 15 Phiadh, endolysin from the *Streptococcus pneumoniae* bacteriophage Cp-I, bifunctional peptidoglycan lysin of *Streptococcus agalactiae* bacteriophage B30, endolysins and exolysins from prophage bacteria, endolysins from *Listeria* bacteriophages, holin-endolysin, cell 20 lysis genes, holWMY *Staphylococcus wameri* M phage varphiWMY, ly5WMY of the *Staphylococcus wameri* M phage varphiWMY, and combinations thereof. In some cases a buffer may comprise a lysis agent (e.g., a lysis buffer). An example of a lysis buffer is sodium hydroxide (NaOH).

Any type of nucleic acid amplification reaction known in the art may be used to amplify a target nucleic acid and generate an amplified product. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction, ligase chain reaction, helicase-dependent amplification, asymmetric amplification, rolling circle amplification, and multiple displacement amplification (MDA). In some embodiments, the amplified product may be DNA. In cases where a target RNA is amplified, DNA can be obtained by reverse transcription of the RNA and subsequent amplification of the DNA can be used to generate an amplified DNA product. The amplified DNA product may be indicative of the presence of the target RNA in the biological sample. In cases where DNA is amplified, any DNA amplification method known in the art may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

In various aspects, nucleic acid amplification reactions described herein may be conducted in parallel. In general, parallel amplification reactions are amplification reactions that occur in the same reaction vessel and at the same time. Parallel nucleic acid amplification reactions may be conducted, for example, by including reagents necessary for each nucleic acid amplification reaction in a reaction vessel to obtain a reaction mixture and subjecting the reaction mixture to conditions necessary for each nucleic amplification reaction. For example, reverse transcription amplification and DNA amplification may be conducted in parallel, by providing reagents necessary for both amplification methods in a reaction vessel to form to obtain a reaction mixture and subjecting the reaction mixture to conditions suitable for conducting both amplification reactions. DNA generated from reverse transcription of the RNA may be amplified in parallel to generate an amplified DNA product. Any suitable number of nucleic acid amplification reactions may be conducted in parallel. In some cases, at least 1, 2, 3, 4, 5, 6, 7, 8, 9, 10, 11, 12, 13, 14, 15, 16, 17, 18, 19, 20, or more nucleic acid amplification reactions are conducted in parallel.

An advantage of conducting nucleic acid amplification reactions in parallel can include fast transitions between coupled nucleic acid amplification reactions. For example, a target nucleic acid (e.g., target RNA, target DNA) may be extracted or released from a biological sample during heating phases of parallel nucleic acid amplification. In the case of a target RNA, for example, the biological sample comprising the target RNA can be heated and the target RNA released from the biological sample. The released target RNA can immediately begin reverse transcription (via reverse transcription amplification) to produce complementary DNA. The complementary DNA can then be immediately amplified, often on the order of seconds. Short times between release of a target RNA from a biological sample and reverse transcription of the target RNA to complementary DNA may help minimize the effects of inhibitors in the biological sample that may impede reverse transcription and/or DNA amplification.

In any of the various aspects, primer sets directed to a target nucleic acid may be utilized to conduct nucleic acid amplification reaction. Primer sets generally comprise one or more primers. For example, a primer set may comprise about 1, 2, 3, 4, 5, 6, 7, 8, 9, 10, or more primers. In some cases, a primer set or may comprise primers directed to different amplified products or different nucleic acid amplification reactions. For example, a primer set may comprise a first primer necessary to generate a first strand of nucleic acid product that is complementary to at least a portion of the target nucleic acid and a second primer complementary to the nucleic acid strand product necessary to generate a second strand of nucleic acid product that is complementary to at least a portion of the first strand of nucleic acid product.

For example, a primer set may be directed to a target RNA. The primer set may comprise a first primer that can be used to generate a first strand of nucleic acid product that is complementary to at least a portion the target RNA. In the case of a reverse transcription reaction, the first strand of nucleic acid product may be DNA. The primer set may also comprise a second primer that can be used to generate a second strand of nucleic acid product that is complementary to at least a portion of the first strand of nucleic acid product. In the case of a reverse transcription reaction conducted in parallel with DNA amplification, the second strand of nucleic acid product may be a strand of nucleic acid (e.g., DNA) product that is complementary to a strand of DNA generated from an RNA template.

Where desired, any suitable number of primer sets may be used. For example, about 1, 2, 3, 4, 5, 6, 7, 8, 9, 10, or more primer sets may be used. Where multiple primer sets are used, one or more primer sets may each correspond to a particular nucleic acid amplification reaction or amplified product.

In some embodiments, a DNA polymerase is used. Any suitable DNA polymerase may be used, including commercially available DNA polymerases. A DNA polymerase generally refers to an enzyme that is capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products and derivatives thereof. For certain Hot Start Polymerase, a denaturation step at 94° C.-95° C. for 2 minutes to 10 minutes may be required, which may change the thermal profile based on different polymerases.

In some embodiments, a reverse transcriptase is used. Any suitable reverse transcriptase may be used. A reverse transcriptase generally refers to an enzyme that is capable of incorporating nucleotides to a strand of DNA, when bound to an RNA template. Non-limiting examples of reverse transcriptases include HIV-1 reverse transcriptase, M-MLV reverse transcriptase, AMV reverse transcriptase, telomerase reverse transcriptase, and variants, modified products and derivatives thereof.

In various aspects, primer extension reactions are utilized to generate amplified product. Primer extension reactions generally comprise a cycle of incubating a reaction mixture at a denaturation temperature for a denaturation duration and incubating a reaction mixture at an elongation temperature for an elongation duration.

Denaturation temperatures may vary depending upon, for example, the particular biological sample analyzed, the particular source of target nucleic acid (e.g., viral particle, bacteria) in the biological sample, the reagents used, and/or the desired reaction conditions. For example, a denaturation temperature may be from about 80° C. to about 110° C. In some examples, a denaturation temperature may be from about 90° C. to about 100° C. In some examples, a denaturation temperature may be from about 90° C. to about 97° C. In some examples, a denaturation temperature may be from about 92° C. to about 95° C. In still other examples, a denaturation temperature may be about 80°, 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

Denaturation durations may vary depending upon, for example, the particular biological sample analyzed, the particular source of target nucleic acid (e.g., viral particle, bacteria) in the biological sample, the reagents used, and/or the desired reaction conditions. For example, a denaturation duration may be less than or equal to 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. For example, a denaturation duration may be no more than 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

Elongation temperatures may vary depending upon, for example, the particular biological sample analyzed, the particular source of target nucleic acid (e.g., viral particle, bacteria) in the biological sample, the reagents used, and/or the desired reaction conditions. For example, an elongation temperature may be from about 30° C. to about 80° C. In some examples, an elongation temperature may be from about 35° C. to about 72° C. In some examples, an elongation temperature may be from about 45° C. to about 65° C. In some examples, an elongation temperature may be from about 35° C. to about 65° C. In some examples, an elongation temperature may be from about 40° C. to about 60° C. In some examples, an elongation temperature may be from about 50° C. to about 60° C. In still other examples, an elongation temperature may be about 35°, 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

Elongation durations may vary depending upon, for example, the particular biological sample analyzed, the particular source of target nucleic acid (e.g., viral particle, bacteria) in the biological sample, the reagents used, and/or the desired reaction conditions. For example, an elongation duration may be less than or equal to 300 seconds, 240 seconds, 180 seconds, 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second. For example, an elongation duration may be no more than 120 seconds, 90 seconds, 60 seconds, 55 seconds, 50 seconds, 45 seconds, 40 seconds, 35 seconds, 30 seconds, 25 seconds, 20 seconds, 15 seconds, 10 seconds, 5 seconds, 2 seconds, or 1 second.

In any of the various aspects, multiple cycles of a primer extension reaction can be conducted. Any suitable number of cycles may be conducted. For example, the number of cycles conducted may be less than about 100, 90, 80, 70, 60, 50, 40, 30, 20, 10, or 5 cycles. The number of cycles conducted may depend upon, for example, the number of cycles (e.g., cycle threshold value (Ct)) necessary to obtain a detectable amplified product (e.g., a detectable amount of amplified DNA product that is indicative of the presence of a target RNA in a biological sample). For example, the number of cycles necessary to obtain a detectable amplified product (e.g., a detectable amount of DNA product that is indicative of the presence of a target RNA in a biological sample) may be less than about or about 100 cycles, 75 cycles, 70 cycles, 65 cycles, 60 cycles, 55 cycles, 50 cycles, 40 cycles, 35 cycles, 30 cycles, 25 cycles, 20 cycles, 15 cycles, 10 cycles, or 5 cycles. Moreover, in some embodiments, a detectable amount of an amplifiable product (e.g., a detectable amount of DNA product that is indicative of the presence of a target RNA in a biological sample) may be obtained at a cycle threshold value (Ct) of less than 100, 75, 70, 65, 60, 55, 50, 45, 40, 35, 30, 25, 20, 15, 10, or 5.

The time for which amplification yields a detectable amount of amplified product indicative of the presence of a target nucleic acid amplified can vary depending upon the biological sample from which the target nucleic acid was obtained, the particular nucleic acid amplification reactions to be conducted, and the particular number of cycles of amplification reaction desired. For example, amplification of a target nucleic acid may yield a detectable amount of amplified product indicative to the presence of the target nucleic acid at time period of 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less.

In some embodiments, amplification of a target RNA may yield a detectable amount of amplified DNA product indicative to the presence of the target RNA at time period of 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less.

In some embodiments, a reaction mixture may be subjected to a plurality of series of primer extension reactions. An individual series of the plurality may comprise multiple cycles of a particular primer extension reaction, characterized, for example, by particular denaturation and elongation conditions as described elsewhere herein. Generally, each individual series differs from at least one other individual series in the plurality with respect to, for example, a denaturation condition and/or elongation condition. An individual series may differ from another individual series in a plurality of series, for example, with respect to any one, two, three, or all four of denaturing temperature, denaturing duration, elongation temperature, and elongation duration. Moreover, a plurality of series may comprise any number of individual series such as, for example, at least about or about 2, 3, 4, 5, 6, 7, 8, 9, 10, or more individual series.

For example, a plurality of series of primer extension reactions may comprise a first series and a second series. The first series, for example, may comprise more than ten cycles of a primer extension reaction, where each cycle of the first series comprises (i) incubating a reaction mixture at about 92° C. to about 95° C. for no more than 30 seconds followed by (ii) incubating the reaction mixture at about 35° C. to about 65° C. for no more than about one minute. The second series, for example, may comprise more than ten cycles of a primer extension reaction, where each cycle of the second series comprises (i) incubating the reaction mixture at about 92° C. to about 95° C. for no more than 30 seconds followed by (ii) incubating the reaction mixture at about 40° C. to about 60° C. for no more than about 1 minute. In this particular example, the first and second series differ in their elongation temperature condition. The example, however, is not meant to be limiting as any combination of different elongation and denaturing conditions could be used.

In some embodiments, the ramping time (i.e., the time the thermal cycler takes to transition from one temperature to another) and/or ramping rate can be important factors in amplification. For example, the temperature and time for which amplification yields a detectable amount of amplified product indicative of the presence of a target nucleic acid can vary depending upon the ramping rate and/or ramping time. The ramping rate can impact the temperature(s) and time(s) used for amplification.

In some cases, the ramping time and/or ramping rate can be different between cycles. In some situations, however, the ramping time and/or ramping rate between cycles can be the same. The ramping time and/or ramping rate can be adjusted based on the sample(s) that are being processed.

In some situations, the ramping time between different temperatures can be determined, for example, based on the nature of the sample and the reaction conditions. The exact temperature and incubation time can also be determined based on the nature of the sample and the reaction conditions. In some embodiments, a single sample can be processed (e.g., subjected to amplification conditions) multiple times using multiple thermal cycles, with each thermal cycle differing for example by the ramping time, temperature, and/or incubation time. The best or optimum thermal cycle can then be chosen for that particular sample. This provides a robust and efficient method of tailoring the thermal cycles to the specific sample or combination of samples being tested.

In some embodiments, a target nucleic acid may be subjected to a denaturing condition prior to initiation of a primer extension reaction. In the case of a plurality of series of primer extension reactions, the target nucleic acid may be subjected to a denaturing condition prior to executing the plurality of series or may be subjected to a denaturing condition between series of the plurality. For example, the target nucleic acid may be subjected to a denaturing condition between a first series and a second series of a plurality of series. Non-limiting examples of such denaturing conditions include a denaturing temperature profile (e.g., one or more denaturing temperatures) and a denaturing agent.

An advantage of conducting a plurality of series of primer extension reaction may be that, when compared to a single series of primer extension reactions under comparable denaturing and elongation conditions, the plurality of series approach yields a detectable amount of amplified product that is indicative of the presence of a target nucleic acid in a biological sample with a lower cycle threshold value. Use of a plurality of series of primer extension reactions may reduce such cycle threshold values by at least about or about 1%, 5%, 10%, 15%, 20%, 25%, 30%, 35%, 40%, 45%, 50%, 55%, 60%, 65%, 70%, 75%, 80%, 85%, 90%, or 95% when compared to a single series under comparable denaturing and elongation conditions.

In some embodiments, a biological sample may be preheated prior to conducting a primer extension reaction. The temperature (e.g., a preheating temperature) at which and duration (e.g., a preheating duration) for which a biological sample is preheated may vary depending upon, for example, the particular biological sample being analyzed. In some examples, a biological sample may be preheated for no more than about 60 minutes, 50 minutes, 40 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, 1 minute, 45 seconds, 30 seconds, 20 seconds, 15 seconds, 10 seconds, or 5 seconds. In some examples, a biological sample may be preheated at a temperature from about 80° C. to about 110° C. In some examples, a biological sample may be preheated at a temperature from about 90° C. to about 100° C. In some examples, a biological sample may be preheated at a temperature from about 90° C. to about 97° C. In some examples, a biological sample may be preheated at a temperature from about 92° C. to about 95° C. In still other examples, a biological sample may be preheated at a temperature of about 80°, 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

In some embodiments, reagents necessary for conducting nucleic acid amplification, including reagents necessary for conduction of parallel nucleic acid amplification may also include a reporter agent that yields a detectable signal whose presence or absence is indicative of the presence of an amplified product. The intensity of the detectable signal may be proportional to the amount of amplified product. In some cases, where amplified product is generated of a different type of nucleic acid than the target nucleic acid initially amplified, the intensity of the detectable signal may be proportional to the amount of target nucleic acid initially amplified. For example, in the case of amplifying a target RNA via parallel reverse transcription and amplification of the DNA obtained from reverse transcription, reagents necessary for both reactions may also comprise a reporter agent may yield a detectable signal that is indicative of the presence of the amplified DNA product and/or the target RNA amplified. The intensity of the detectable signal may be proportional to the amount of the amplified DNA product and/or the original target RNA amplified. The use of a reporter agent also enables real-time amplification methods, including real-time PCR for DNA amplification.

Reporter agents may be linked with nucleic acids, including amplified products, by covalent or non-covalent means. Non-limiting examples of non-covalent means include ionic interactions, Van der Waals forces, hydrophobic interactions, hydrogen bonding, and combinations thereof. In some embodiments, reporter agents may bind to initial reactants and changes in reporter agent levels may be used to detect amplified product. In some embodiments, reporter agents may only be detectable (or non-detectable) as nucleic acid amplification progresses. In some embodiments, an optically-active dye (e.g., a fluorescent dye) may be used as may be used as a reporter agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5-(or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-aminomethyl-coumarin, 7-Amino-4-methylcoumarin-3-acetic acid (AMCA), BODIPY fluorophores, 8-methoxypyrene-1, 3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some embodiments, a reporter agent may be a sequence-specific oligonucleotide probe that is optically active when hybridized with an amplified product. Due to sequence-specific binding of the probe to the amplified product, use of oligonucleotide probes can increase specificity and sensitivity of detection. A probe may be linked to any of the optically-active reporter agents (e.g., dyes) described herein and may also include a quencher capable of blocking the optical activity of an associated dye. Non-limiting examples of probes that may be useful used as reporter agents include TaqMan probes, TaqMan Tamara probes, TaqMan MGB probes, or Lion probes.

In some embodiments and where a reporter agent may be an RNA olignucleotide probe that includes an optically-active dye (e.g., fluorescent dye) and a quencher positioned adjacently on the probe. The close proximity of the dye with the quencher can block the optical activity of the dye. The probe may bind to a target sequence to be amplified. Upon the breakdown of the probe with the exonuclease activity of a DNA polymerase during amplification, the quencher and dye are separated, and the free dye regains its optical activity that can subsequently be detected.

In some embodiments, a reporter agent may be a molecular beacon. A molecular beacon includes, for example, a quencher linked at one end of an oligonucleotide in a hairpin conformation. At the other end of the oligonucleotide is an optically active dye, such as, for example, a fluorescent dye. In the hairpin configuration, the optically-active dye and quencher are brought in close enough proximity such that the quencher is capable of blocking the optical activity of the dye. Upon hybridizing with amplified product, however, the oligonucleotide assumes a linear conformation and hybridizes with a target sequence on the amplified product. Linearization of the oligonucleotide results in separation of the optically-active dye and quencher, such that the optical activity is restored and can be detected. The sequence specificity of the molecular beacon for a target sequence on the amplified product can improve specificity and sensitivity of detection.

In some embodiments, a reporter agent may be a radioactive species. Non-limiting examples of radioactive species include $^{14}C$, $^{123}I$, $^{124}I$, $^{125}I$, $^{131}I$, Tc99m, $^{35}S$, or $^{3}H$.

In some embodiments, a reporter agent may be an enzyme that is capable of generating a detectable signal. Detectable signal may be produced by activity of the enzyme with its substrate or a particular substrate in the case the enzyme has multiple substrates. Non-limiting examples of enzymes that may be used as reporter agents include alkaline phosphatase, horseradish peroxidase, $I^2$-galactosidase, alkaline phosphatase, β-galactosidase, acetylcholinesterase, and luciferase.

In various aspects, amplified product (e.g., amplified DNA product, amplified RNA product) may be detected. Detection of amplified product, including amplified DNA, may be accomplished with any suitable detection method known in the art. The particular type of detection method used may depend, for example, on the particular amplified product, the type of reaction vessel used for amplification, other reagents in a reaction mixture, whether or not a reporter agent was included in a reaction mixture, and if a reporter agent was used, the particular type of reporter agent use. Non-limiting examples of detection methods include optical detection, spectroscopic detection, electrostatic detection, electrochemical detection, and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

In any of the various aspects, the time required to complete the elements of a method may vary depending upon the particular steps of the method. For example, an amount of time for completing the elements of a method may be from about 5 minutes to about 120 minutes. In other examples, an amount of time for completing the elements of a method may be from about 5 minutes to about 60 minutes. In other examples, an amount of time for completing the elements of a method may be from about 5 minutes to about 30 minutes. In other examples, an amount of time for completing the elements of a method may be less than or equal to 120 minutes, less than or equal to 90 minutes, less than or equal to 75 minutes, less than or equal to 60 minutes, less than or equal to 45 minutes, less than or equal to 40 minutes, less than or equal to 35 minutes, less than or equal to 30 minutes, less than or equal to 25 minutes, less than or equal to 20 minutes, less than or equal to 15 minutes, less than or equal to 10 minutes, or less than or equal to 5 minutes.

In some embodiments, information regarding the presence of and/or an amount of amplified product (e.g., amplified DNA product) may be outputted to a recipient. Information regarding amplified product may be outputted via any suitable means known in the art. In some embodiments, such information may be provided verbally to a recipient. In some embodiments, such information may be provided in a report. A report may include any number of desired elements, with non-limiting examples that include information regarding the subject (e.g., sex, age, race, health status, etc.) raw data, processed data (e.g. graphical displays (e.g., figures, charts, data tables, data summaries), determined cycle threshold values, calculation of starting amount of target polynucleotide), conclusions about the presence of the target nucleic acid, diagnosis information, prognosis information, disease information, and the like, and combinations thereof. The report may be provided as a printed report (e.g., a hard copy) or may be provided as an electronic report. In some embodiments, including cases where an electronic report is provided, such information may be outputted via an electronic display (e.g., an electronic display screen), such as a monitor or television, a screen operatively linked with a unit used to obtain the amplified product, a tablet computer screen, a mobile device screen, and the like. Both printed and electronic reports may be stored in files or in databases, respectively, such that they are accessible for comparison with future reports.

Moreover, a report may be transmitted to the recipient at a local or remote location using any suitable communication medium including, for example, a network connection, a wireless connection, or an internet connection. In some embodiments, a report can be sent to a recipient's device, such as a personal computer, phone, tablet, or other device. The report may be viewed online, saved on the recipient's device, or printed. A report can also be transmitted by any other suitable means for transmitting information, with non-limiting examples that include mailing a hard-copy report for reception and/or for review by a recipient.

Moreover, such information may be outputted to various types of recipients. Non-limiting examples of such recipients include the subject from which the biological sample was obtained, a physician, a physician treating the subject, a clinical monitor for a clinical trial, a nurse, a researcher, a laboratory technician, a representative of a pharmaceutical company, a health care company, a biotechnology company, a hospital, a human aid organization, a health care manager, an electronic system (e.g., one or more computers and/or one or more computer servers storing, for example, a subject's medical records), a public health worker, other medical personnel, and other medical facilities.

In an aspect, the disclosure provides a system that implements a method according to any of the methods disclosed herein. In another aspect, the disclosure provides a system for amplifying a target ribonucleic acid (RNA) present in a biological sample obtained directly from a subject. The system comprises: (a) an input module that receives a user request to amplify the target RNA in the biological sample; (b) an amplification module that, in response to the user request: receives, in a reaction vessel, a reaction mixture comprising the biological sample and reagents necessary for conducting reverse transcription amplification in parallel with deoxyribonucleic acid (DNA) amplification, the reagents comprising (i) a reverse transcriptase, (ii) a DNA polymerase, and (iii) a primer set for the target RNA; and subjects the reaction mixture in the reaction vessel to multiple cycles of a primer extension reaction to generate amplified DNA product that is indicative of the presence of the target RNA, each cycle comprising (i) incubating the reaction mixture at a denaturing temperature for a denaturing duration that is less than or equal to 60 seconds, followed by (ii) incubating the reaction mixture at an elongation temperature for an elongation duration that is less than or equal to 60 seconds, thereby amplifying the target RNA; and (c) an output module operatively coupled to the amplification module, wherein the output module outputs information regarding the target RNA or the DNA product to a recipient.

In another aspect, the disclosure provides a system for amplifying a target ribonucleic acid (RNA) present in a biological sample obtained directly from a subject. The system comprises: (a) an input module that receives a user request to amplify the target RNA in the biological sample; (b) an amplification module that, in response to the user request: (i) receives, in a reaction vessel, a reaction mixture comprising the biological sample that has been obtained from the subject and reagents necessary for conducting reverse transcription amplification and optionally deoxyribonucleic acid (DNA) amplification, the reagents comprising (1) a reverse transcriptase and (2) a primer set for the target RNA; and (ii) subjects the reaction mixture to multiple cycles of a primer extension reaction to yield a detectable amount of amplified DNA product that is indicative of the presence of the target RNA in the biological sample; (iii) detects the amount of amplified DNA product of (iii); and (iv) outputs information regarding the amount of amplified DNA product to a recipient, wherein an amount of time for completing (i)-(iv) is less than or equal to about 30 minutes; and (c) an output module operatively coupled to the amplification module, wherein the output module transmits the information to a recipient.

In another aspect, the disclosure provides a system for amplifying a target nucleic acid present in a biological sample obtained from a subject. The system comprises: (a) an input module that receives a user request to amplify the target RNA in the biological sample; (b) an amplification module that, in response to the user request: receives, in a reaction vessel, a reaction mixture comprising the biological sample and reagents necessary for conducting nucleic acid amplification, the reagents comprising (i) a DNA polymerase and optionally a reverse transcriptase, and (ii) a primer set for the target nucleic acid; and subjects the reaction mixture in the reaction vessel to a plurality of series of primer extension reactions to generate amplified product that is indicative of the presence of the target nucleic acid in the biological sample, each series comprising two or more cycles of (i) incubating the reaction mixture under a denaturing condition characterized by a denaturing temperature and a denaturing duration, followed by (ii) incubating the reaction mixture under an elongation condition characterized by an elongation temperature and an elongation duration, wherein an individual series differs from at least one other individual series of the plurality with respect to the denaturing condition and/or the elongation condition; and (c) an output module operatively coupled to the amplification module, wherein the output module outputs information regarding the target RNA or the DNA product to a recipient.

In another aspect, the disclosure provides a system for amplifying a target nucleic acid in a biological sample obtained from a subject. The system can include an electronic display screen that has a user interface that displays a graphical element that is accessible by a user to execute an amplification protocol to amplify the target nucleic acid in the biological sample. The system can also include a computer processor (including any suitable device having a computer processor as described elsewhere herein) coupled to the electronic display screen and programmed to execute the amplification protocol upon selection of the graphical element by the user. The amplification protocol can comprise subjecting a reaction mixture comprising the biological sample and reagents necessary for conducting nucleic acid amplification to a plurality of series of primer extension reactions to generate amplified product. The amplified product can be indicative of the presence of the target nucleic acid in the biological sample. Moreover, each series of primer extension reactions can comprise two or more cycles of incubating the reaction mixture under a denaturing condition that is characterized by a denaturing temperature and a denaturing duration, followed by incubating the reaction mixture under an elongation condition that is characterized by an elongation temperature and an elongation duration. An individual series can differ from at least one other individual series of the plurality with respect to the denaturing condition and/or the elongation condition.

In some embodiments, the target nucleic acid may be associated with a disease. The disease may be, for example, associated with an RNA virus or a DNA virus. Examples of viruses are provided elsewhere herein. In some embodiments, the disease may be associated with a pathogenic bacterium (e.g., *Mycobacterium tuberculosis*) or a pathogenic protozoan (e.g., *Plasmodium* as in Malaria), including examples of such pathogens described elsewhere herein. In some embodiments, the amplification protocol can be directed to assaying for the presence of said disease based on a presence of the amplified product.

In some cases, a user interface can be a graphical user interface. Moreover, a user interface can include one or more graphical elements. Graphical elements can include image and/or textual information, such as pictures, icons and text. The graphical elements can have various sizes and orientations on the user interface. Furthermore, an electronic display screen may be any suitable electronic display including examples described elsewhere herein. Non-limiting examples of electronic display screens include a monitor, a mobile device screen, a laptop computer screen, a television, a portable video game system screen and a calculator screen. In some embodiments, an electronic display screen may include a touch screen (e.g., a capacitive or resistive touch screen) such that graphical elements displayed on a user interface of the electronic display screen can be selected via user touch with the electronic display screen.

In some embodiments, the amplification protocol may further include selecting a primer set for the target nucleic acid. In such cases, the primer set may be a primer set specifically designed to amplify one or more sequences of the target nucleic acid molecule. In some embodiments, the amplification protocol may further include selecting a reporter agent (e.g., an oligonucleotide probe comprising an optically-active species or other type of reporter agent described elsewhere herein) that is specific for one or more sequences of the target nucleic acid molecule. Moreover, in some embodiments, the reagents may comprise any suitable reagents necessary for nucleic acid amplification as described elsewhere herein, such as, for example, a deoxyribonucleic acid (DNA) polymerase, a primer set for the target nucleic acid, and (optionally) a reverse transcriptase.

Figure 28A:
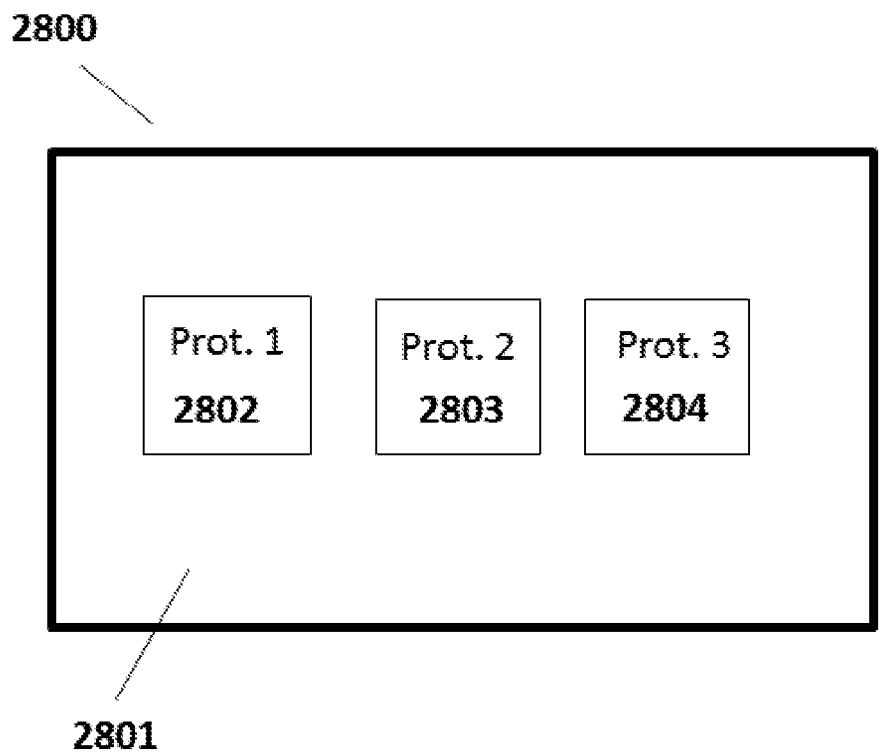
FIG. 28A is a schematic of an example electronic display having an example user interface.

In some embodiments, the user interface can display a plurality of graphical elements. Each of the graphical elements can be associated with a given amplification protocol among a plurality of amplification protocols. Each of the plurality of amplification protocols may include a different combination of series of primer extension reaction. In some cases, though, a user interface may display a plurality of graphical elements associated with the same amplification protocol. An example of a user interface having a plurality of graphical elements each associated with a given amplification protocol is shown in FIG. 28A. As shown in FIG. 28A, an example electronic display screen 2800 associated with a computer processor includes a user interface 2801. The user interface 2801 includes a display of graphical elements 2802, 2803 and 2804. Each of the graphical elements can be associated with a particular amplification protocol (e.g., "Prot. 1" for graphical element 2802, "Prot. 2" for graphical element 2803 and "Prot. 4" for graphical element 2804). Upon user selection (e.g., user touch when the electronic display screen 2800 includes a touch-screen having the user interface) of particular graphical element, the particular amplification protocol associated with the graphical element can be executed by an associated computer processor. For example, when a user selects graphical element 2803, amplification "Prot. 2" is executed by the associated computer processor. Where only three graphical elements are shown in the example user interface 2801 of FIG. 28A, a user interface may have any suitable number of graphical elements. Moreover, where each graphical element shown in the user interface 2801 of FIG. 28A is associated with only one amplification protocol, each graphical element of a user interface can be associated with one or more amplification protocols (e.g., a series of amplification protocols) such that an associated computer processor executes a series of amplification protocols upon user interaction with the graphical element.

In some embodiments, each of the graphical elements and/or may be associated with a disease, and a given amplification protocol among the plurality of amplification protocols may be directed to assaying a presence of the disease in the subject. Thus, in such cases, a user can select a graphical element in order to run an amplification protocol (or series of amplification protocols) to assay for a particular disease. In some embodiments, the disease may be associated with a virus such as, for example, any RNA virus or DNA virus including examples of such viruses described elsewhere herein. Non-limiting examples of viruses include human immunodeficiency virus I (HIV I), human immunodeficiency virus II (HIV II), an orthomyxovirus, Ebola virus, Dengue virus, influenza viruses (e.g., H1N1 virus, H3N2 virus, H7N9 virus or H5N1 virus), hepevirus, hepatitis A virus, hepatitis B virus, hepatitis C virus (e.g., armored RNA-hepatitis C virus (RNA-HCV)), hepatitis D virus, hepatitis E virus, hepatitis G virus, Epstein-Barr virus, mononucleosis virus, cytomegalovirus, SARS virus, West Nile Fever virus, polio virus, measles virus, herpes simplex virus, smallpox virus, adenovirus (e.g., adenovirus type 55 (ADV55), adenovirus type 7 (ADV7)) and Varicella virus. In some embodiments, the disease may be associated with a pathogenic bacterium (e.g., *Mycobacterium tuberculosis*) or a pathogenic protozoan (e.g., *Plasmodium* as in Malaria), including examples of such pathogens described elsewhere herein.

Figure 28B:
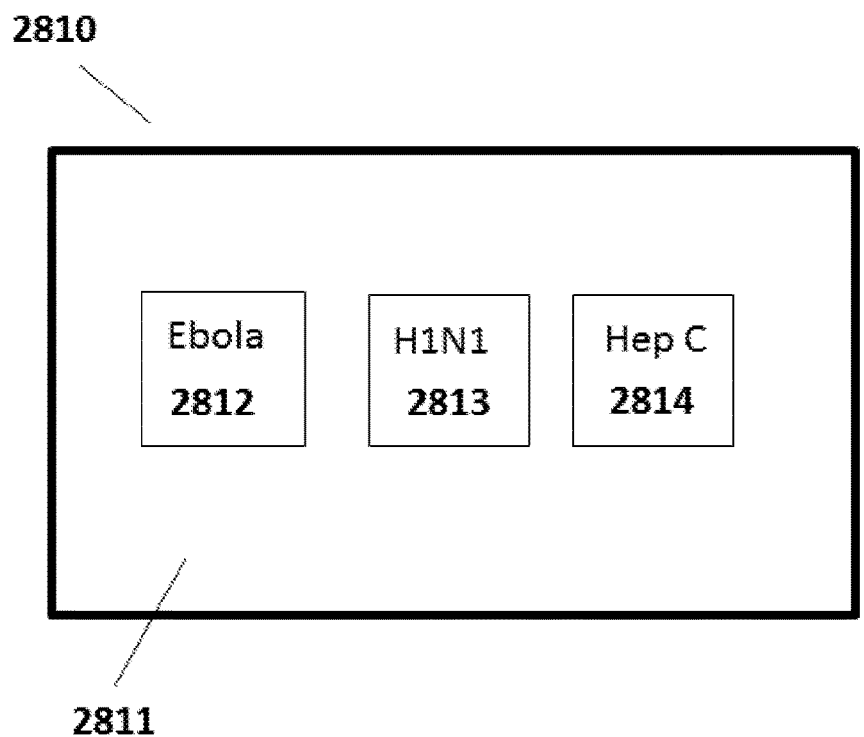
FIG. 28B is a schematic of an example electronic display having an example user interface.

An example of a user interface having a plurality of graphical elements each associated with a given amplification protocol is shown in FIG. 28B. As shown in FIG. 28B, an example electronic display screen 2810 associated with a computer processor includes a user interface 2811. The user interface 2811 includes a display of graphical elements 2812, 2813 and 2814. Each of the graphical elements can be associated with a particular disease (e.g., "Ebola" for graphical element 2812, "H1N1" for graphical element 2813 and "Hep C" (Hepatitis C) for graphical element 2814) that is, in turn, associated with one or more amplification protocols directed toward the particular disease. Upon user selection (e.g., user touch when the electronic display screen 2810 includes a touch-screen having the user interface) with a particular graphical element, the particular amplification protocol(s) associated with the disease associated with the graphical element can be executed by an associated computer processor. For example, when a user interacts with graphical element 2812, one or more amplification protocols associated with assaying for Ebola virus can be executed by the associated computer processor. Where only three graphical elements are shown in the example user interface 2811 of FIG. 28B, a user interface may have any suitable number of graphical elements each corresponding to a various disease. Moreover, where each graphical element shown in the user interface 2811 of FIG. 28B is associated with only one disease, each graphical element of a user interface can be associated with one or more diseases such that an associated computer processor executes a series of amplification protocols (e.g., each individual amplification protocol directed to a particular disease) upon user selection of the graphical element. For example, a graphical element may correspond to Ebola virus and H1N1 virus such that selection of the graphical element results in an associated computer processor executing amplification protocols for both Ebola virus and H1N1 virus.

In various aspects, the system comprises an input module that receives a user request to amplify a target nucleic acid (e.g., target RNA, target DNA) present in a biological sample obtained direct from a subject. Any suitable module capable of accepting such a user request may be used. The input module may comprise, for example, a device that comprises one or more processors. Non-limiting examples of devices that comprise processors (e.g., computer processors) include a desktop computer, a laptop computer, a tablet computer (e.g., Apple® iPad, Samsung® Galaxy Tab), a cell phone, a smart phone (e.g., Apple® iPhone, Android® enabled phone), a personal digital assistant (PDA), a video-game console, a television, a music playback device (e.g., Apple® iPod), a video playback device, a pager, and a calculator. Processors may be associated with one or more controllers, calculation units, and/or other units of a computer system, or implanted in firmware as desired. If implemented in software, the routines (or programs) may be stored in any computer readable memory such as in RAM, ROM, flash memory, a magnetic disk, a laser disk, or other storage medium. Likewise, this software may be delivered to a device via any known delivery method including, for example, over a communication channel such as a telephone line, the internet, a local intranet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

In some embodiments, the input module is configured to receive a user request to perform amplification of the target nucleic acid. The input module may receive the user request directly (e.g. by way of an input device such as a keyboard, mouse, or touch screen operated by the user) or indirectly (e.g. through a wired or wireless connection, including over the internet). Via output electronics, the input module may provide the user's request to the amplification module. In some embodiments, an input module may include a user interface (UI), such as a graphical user interface (GUI), that is configured to enable a user provide a request to amplify the target nucleic acid. A GUI can include textual, graphical and/or audio components. A GUI can be provided on an electronic display, including the display of a device comprising a computer processor. Such a display may include a resistive or capacitive touch screen.

Non-limiting examples of users include the subject from which the biological sample was obtained, medical personnel, clinicians (e.g., doctors, nurses, laboratory technicians), laboratory personnel (e.g., hospital laboratory technicians, research scientists, pharmaceutical scientists), a clinical monitor for a clinical trial, or others in the health care industry.

In various aspects, the system comprises an amplification module for performing nucleic acid amplification reaction on target nucleic acid or a portion thereof, in response to a user request received by the input module. The amplification module may be capable of executing any of the methods described herein and may include any of a fluid handling device, one or more thermocyclers, means for receiving one or more reaction vessels (e.g., wells of a thermal block of a thermocycler), a detector (e.g., optical detector, spectroscopic detector, electrochemical detector) capable of detecting amplified product, and means for outputting information (e.g., raw data, processed data, or any other type of information described herein) regarding the presence and/or amount of amplified product (e.g., amplified DNA product) to a recipient. In some cases, the amplification module may comprise a device with a computer processor as described elsewhere herein and may also be capable of analyzing raw data from detection, with the aid of appropriate software. Moreover, in some embodiments, the amplification module may comprise input electronics necessary to receive instructions from the input module and may comprise output electronics necessary to communicate with the output module.

In some embodiments, one or more steps of providing materials to a reaction vessel, amplification of nucleic acids, detection of amplified product, and outputting information may be automated by the amplification module. In some embodiments, automation may comprise the use of one or more fluid handlers and associated software. Several commercially available fluid handling systems can be utilized to run the automation of such processes. Non-limiting examples of such fluid handlers include fluid handlers from Perkin-Elmer, Caliper Life Sciences, Tecan, Eppendorf, Apricot Design, and Velocity 11.

In some embodiments, an amplification module may include a real-time detection instrument. Non-limiting examples of such instruments include a real-time PCR thermocycler, ABI PRISM® 7000 Sequence Detection System, ABI PRISM® 7700 Sequence Detection System, Applied Biosystems 7300 Real-Time PCR System, Applied Biosystems 7500 Real-Time PCR System, Applied Biosystems 7900 HT Fast Real-Time PCR System (all from Applied Biosystems); LightCycler™ System (Roche Diagnostics GmbH); Mx3000P™ Real-Time PCR System, Mx3005P™ Real-Time PCR System, and Mx4000® Multiplex Quantitative PCR System (Stratagene, La Jolla, Calif.); and Smart Cycler System (Cepheid, distributed by Fisher Scientific). In some embodiments, an amplification module may comprise another automated instrument such as, for example, a COBAS® AmpliPrep/COBAS® TaqMan® system (Roche Molecular Systems), a TIGRIS DTS system (Hologic Gen-Probe, San Diego, Calif.), a PANTHER system (Hologic Gen-Probe, San Diego, Calif.), a BD MAX™ system (Becton Dickinson), a GeneXpert System (Cepheid), a Filmarray® (BioFire Diagnostics) system, an iCubate system, an IDBox system (Luminex), an EncompassMDx™ (Rheonix) system, a Liat™ Aanlyzer (IQuum) system, a Biocartis' Molecular Diagnostic Platform system, an Enigma® ML system (Enigma Diagnostics), a T2Dx® system (T2 Biosystems), a Verigene® system (NanoSphere), a Great Basin's Diagnostic System, a Unyvero™ System (Curetis), a PanNAT system (Micronics), or a Spartan™ RX system (Spartan Bioscience).

In various aspects, the system comprises an output module operatively connected to the amplification module. In some embodiments the output module may comprise a device with a processor as described above for the input module. The output module may include input devices as described herein and/or may comprise input electronics for communication with the amplification module. In some embodiments, the output module may be an electronic display, in some cases the electronic display comprising a UI. In some embodiments, the output module is a communication interface operatively coupled to a computer network such as, for example, the internet. In some embodiments, the output module may transmit information to a recipient at a local or remote location using any suitable communication medium, including a computer network, a wireless network, a local intranet, or the internet. In some embodiments, the output module is capable of analyzing data received from the amplification module. In some cases, the output module includes a report generator capable of generating a report and transmitting the report to a recipient, wherein the report contains any information regarding the amount and/or presence of amplified product as described elsewhere herein. In some embodiments, the output module may transmit information automatically in response to information received from the amplification module, such as in the form of raw data or data analysis performed by software included in the amplification module. Alternatively, the output module may transmit information after receiving instructions from a user. Information transmitted by the output module may be viewed electronically or printed from a printer.

One or more of the input module, amplification module, and output module may be contained within the same device or may comprise one or more of the same components. For example, an amplification module may also comprise an input module, an output module, or both. In other examples, a device comprising a processor may be included in both the input module and the output module. A user may use the device to request that a target nucleic acid be amplified and may also be used as a means to transmit information regarding amplified product to a recipient. In some cases, a device comprising a processor may be included in all three modules, such that the device comprising a processor may also be used to control, provide instructions to, and receive information back from instrumentation (e.g., a thermocycler, a detector, a fluid handling device) included in the amplification module or any other module.

An example system for amplifying a target nucleic acid according to methods described herein is depicted in FIG. 1. The system comprises a computer 101 that may serve as part of both the input and output modules. A user enters a reaction vessel 102 comprising a reaction mixture ready for nucleic acid amplification into the amplification module 104. The amplification module comprises a thermocycler 105 and a detector 106. The input module 107 comprises computer 101 and associated input devices 103 (e.g., keyboard, mouse, etc.) that can receive the user's request to amplify a target nucleic acid in the reaction mixture. The input module 107 communicates the user's request to the amplification module 104 and nucleic acid amplification commences in the thermocycler 105. As amplification proceeds, the detector 106 of the amplification module detects amplified product. Information (e.g., raw data obtained by the detector) regarding the amplified product is transmitted from the detector 106 back to the computer 101, which also serves as a component of the output module 108. The computer 101 receives the information from the amplification module 104, performs any additional manipulations to the information, and then generates a report containing the processed information. Once the report is generated, the computer 101 then transmits the report to its end recipient 109 over a computer network (e.g., an intranet, the internet) via computer network interface 110, in hard copy format via printer 111, or via the electronic display 112 operatively linked to computer 101. In some cases, the electronic display 112

In one aspect, the disclosure provides a computer-readable medium comprising machine executable code that, upon execution by one or more processors, implements a method according to any of the methods disclosed herein. In another aspect, the disclosure provides a computer readable medium comprising machine executable code that, upon execution by one or more computer processors, implements a method of amplifying a target ribonucleic acid (RNA) present in a biological sample obtained directly from a subject, the method comprising: (a) providing a reaction vessel comprising the biological sample and reagents necessary for conducting reverse transcription amplification in parallel with deoxyribonucleic acid (DNA) amplification, the reagents comprising (i) a reverse transcriptase, (ii) a DNA polymerase, and (iii) a primer set for the target RNA, to obtain a reaction mixture; and (b) subjecting the reaction mixture in the reaction vessel to multiple cycles of a primer extension reaction to generate amplified DNA product that is indicative of the presence of the target RNA, each cycle comprising (i) incubating the reaction mixture at a denaturing temperature for a denaturing duration that is less than or equal to 60 seconds, followed by (ii) incubating the reaction mixture at an elongation temperature for an elongation duration that is less than or equal to 60 seconds, thereby amplifying the target RNA.

In another aspect, the disclosure provides a computer readable medium comprising machine executable code that, upon execution by one or more computer processors, implements a method of amplifying a target ribonucleic acid (RNA) present in a biological sample obtained directly from a subject, the method comprising: (a) receiving the biological sample that has been obtained from the subject; (b) providing a reaction vessel comprising the biological sample and reagents necessary for conducting reverse transcription amplification and optionally deoxyribonucleic acid (DNA) amplification, the reagents comprising (i) a reverse transcriptase and (ii) a primer set for the target RNA, to obtain a reaction mixture; (c) subjecting the reaction mixture to multiple cycles of a primer extension reaction to yield a detectable amount of amplified DNA product that is indicative of the presence of the target RNA in the biological sample; (d) detecting the amount of DNA product of (c); and (e) outputting information regarding the amount of DNA product to a recipient, wherein an amount of time for completing (a)-(e) is less than or equal to about 30 minutes.

In one aspect, the disclosure provides a computer readable medium comprising machine executable code that, upon execution by one or more computer processors, implements a method of amplifying a target ribonucleic acid (RNA) present in a biological sample obtained from a subject, the method comprising: (a) providing a reaction vessel comprising the biological sample and reagents necessary for conducting nucleic acid amplification, the reagents comprising (i) a DNA polymerase and optionally a reverse transcriptase, and (ii) a primer set for the target nucleic acid, to obtain a reaction mixture; and (b) subjecting the reaction mixture in the reaction vessel to a plurality of series of primer extension reactions to generate amplified product from the target nucleic acid, each series comprising two or more cycles of (i) incubating the reaction mixture under a denaturing condition characterized by a denaturing temperature and a denaturing duration, followed by (ii) incubating the reaction mixture under an elongation condition characterized by an elongation temperature and an elongation duration, wherein an individual series differs from at least one other individual series of the plurality with respect to the denaturing condition and/or the elongation condition.

Computer readable medium may take many forms, including but not limited to, a tangible (or non-transitory) storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

EXAMPLES

Example 1: Amplification and Detection of Nucleic Acids in Viral Stock Samples and Biological Samples Amplification and detection experiments were performed to compare results obtained from viral standard samples and biological samples. Biological samples comprising an RNA viral pathogen and standard samples of the viral pathogen were subject to amplification conditions, such that RNA of the pathogen was amplified. A set of experiments was conducted for each of the H3N2 and H1N1 (2007) influenza viruses. Each biological sample was obtained directly from a subject via an oropharyngeal swab. Each viral standard sample was obtained as a serial dilution of a stock solution comprising the virus. The concentrations of H3N2 and H1N1 (2007) were $10^6$ IU/mL. For H5N1 and H1N1 (2007), dilutions of 1/2, 1/20, 1/200, 1/2000, and 1/20000 were subject to amplification. In each experimental set, a negative control (e.g., a sample comprising no viral RNA) was also subject to amplification.

Five microliters of each sample were combined in a 25 µL reaction tube with reagents necessary to conduct reverse transcription of the viral RNA and reagents necessary to complete amplification of the complementary DNA obtained from reverse transcription (e.g., parallel nucleic acid amplification). The reagents necessary to conduct reverse transcription and DNA amplification were supplied as a commercially available pre-mixture (e.g., Qiagen One-Step RT-PCR or One-Step RT-qPCR kit) comprising reverse transcriptases (e.g., Sensiscript and Omniscript transcriptases), a DNA Polymerase (e.g., HotStarTaq DNA Polymerase), and dNTPs. Moreover, the reaction tubes also included a TaqMan probe comprising a FAM dye for detection of amplified DNA product. To generate amplified DNA product, each reaction mixture was incubated according to a protocol of denaturing and elongation conditions comprising 5 min at 95° C., followed by 20 min at 45° C., followed by 2 min at 95° C., and followed by 40 cycles of 5 seconds at 95° C. and 30 seconds at 55° C. in a real-time PCR thermocycler. Detection of amplified product occurred during incubations.

Figure 2A:
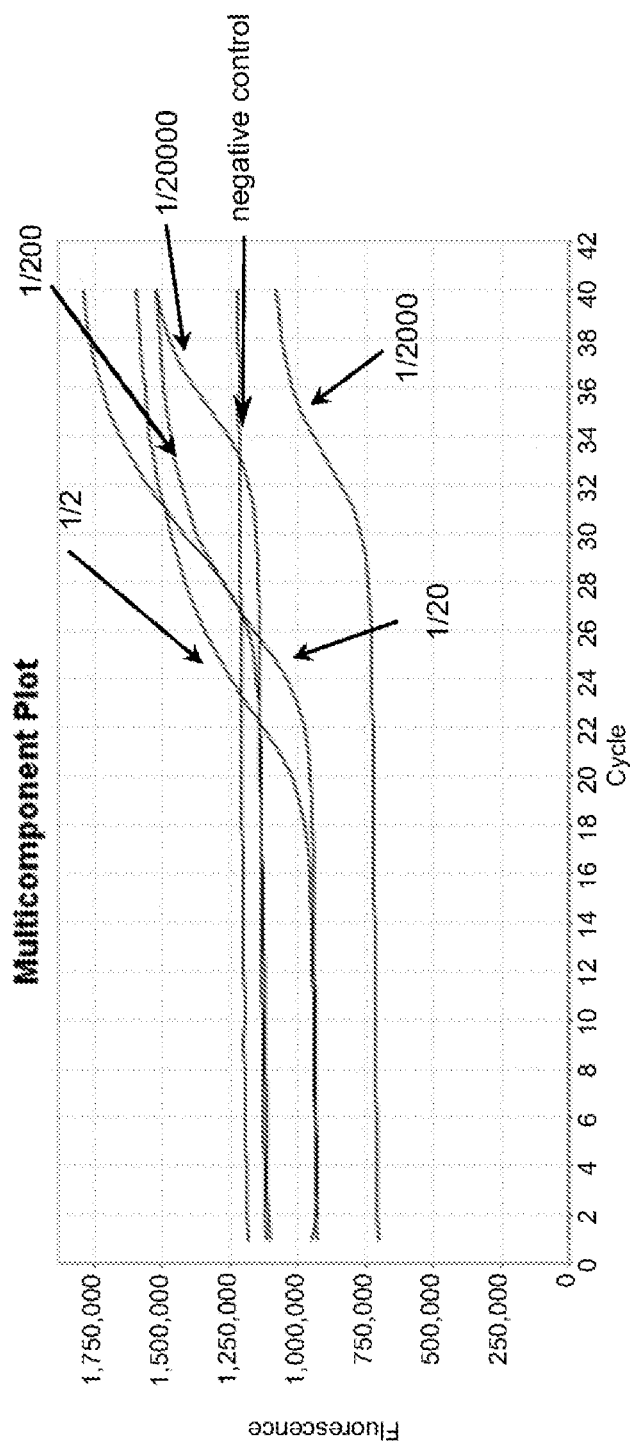
FIGS. 2A and 2B are graphs depicting results of example nucleic acid amplification reactions described in Example 1.
Figure 2B:
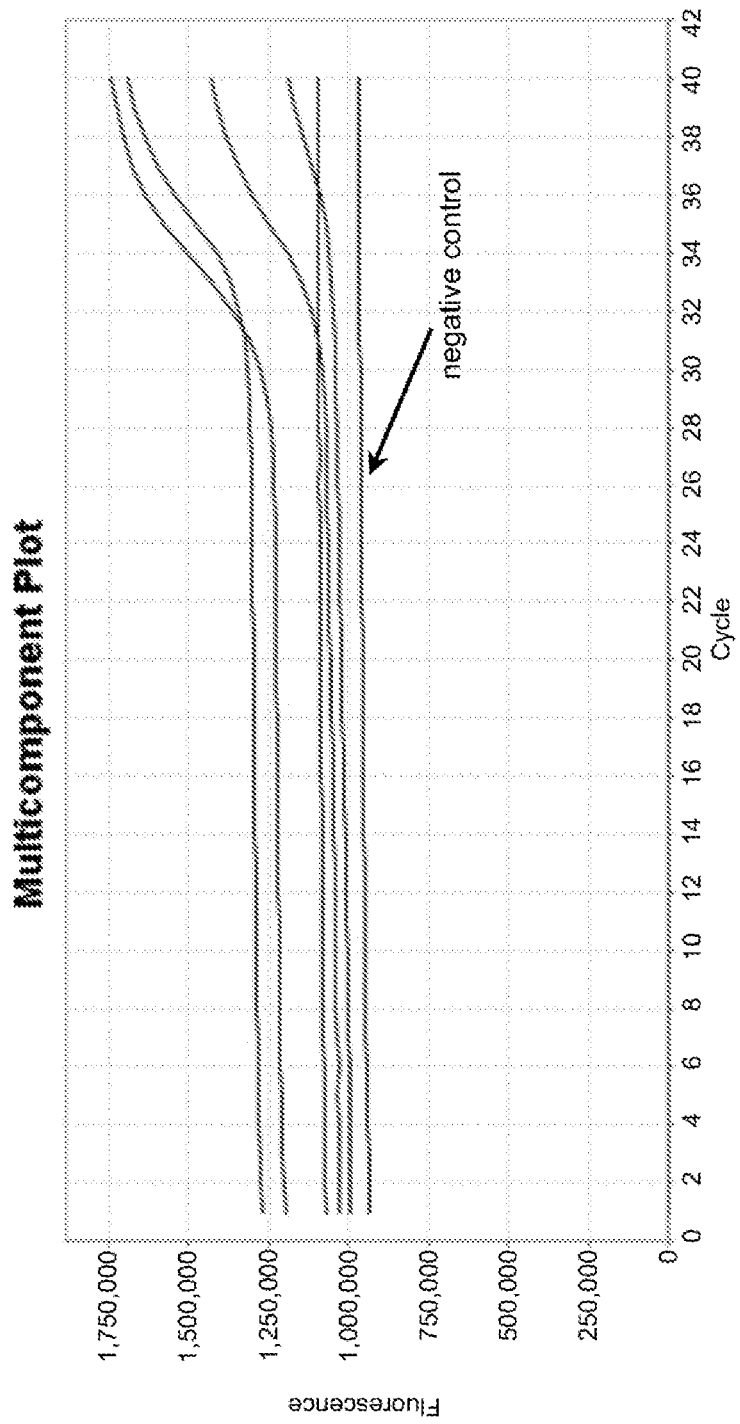
Figure 3A:
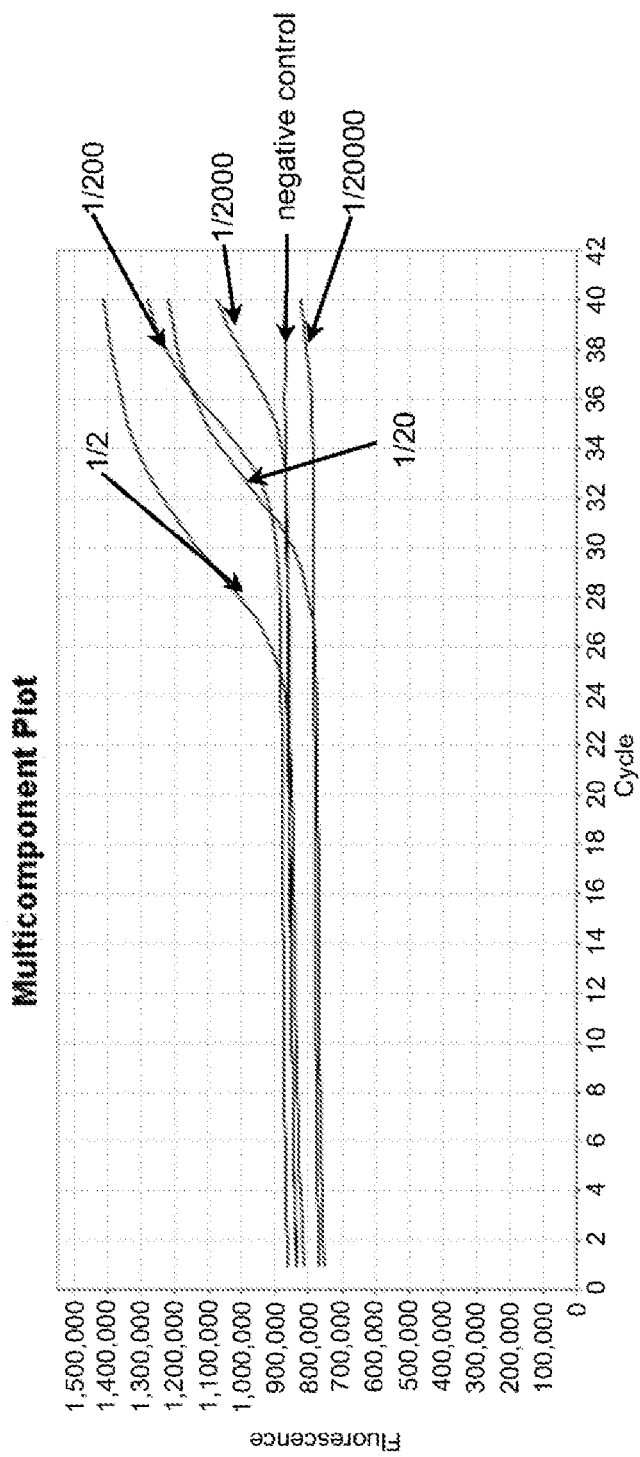
FIGS. 3A and 3B are graphs depicting results of example nucleic acid amplification reactions described in Example 1.
Figure 3B:
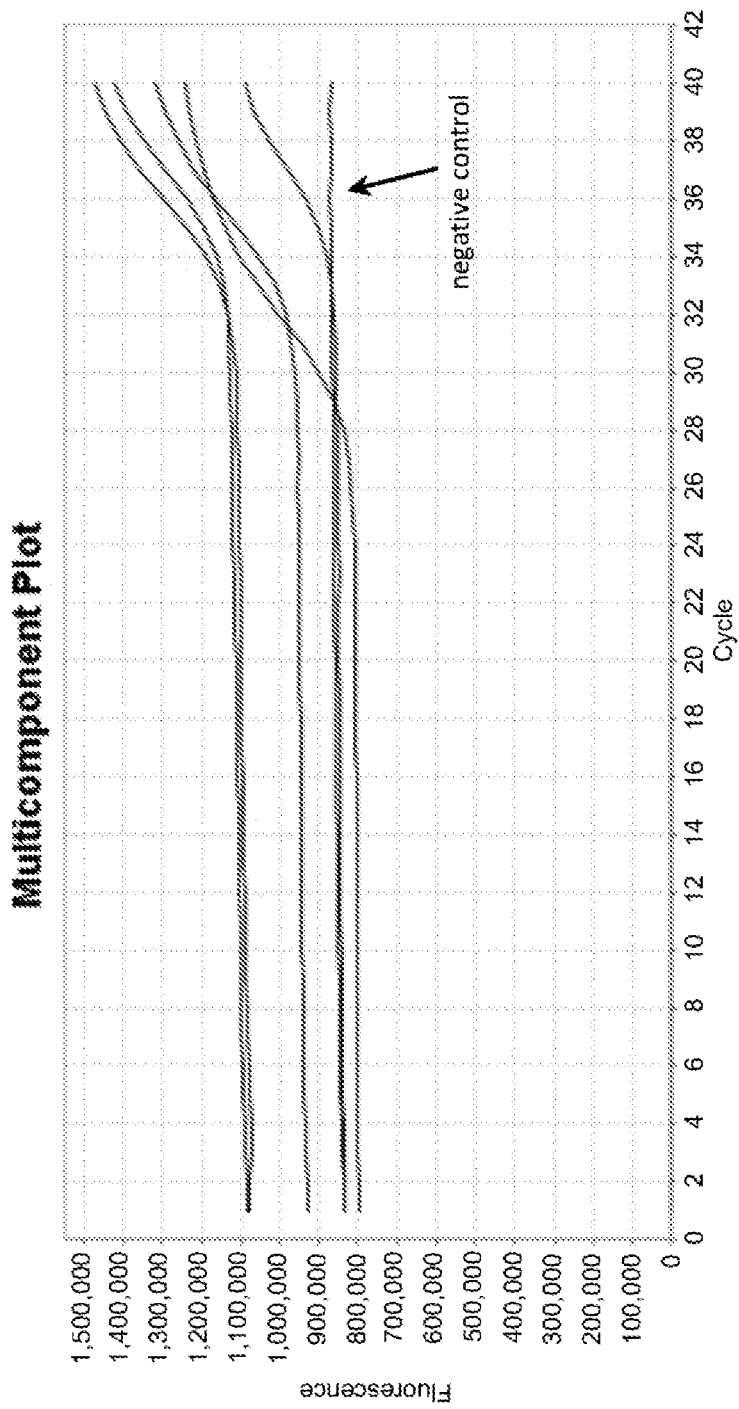
Figure 4A:
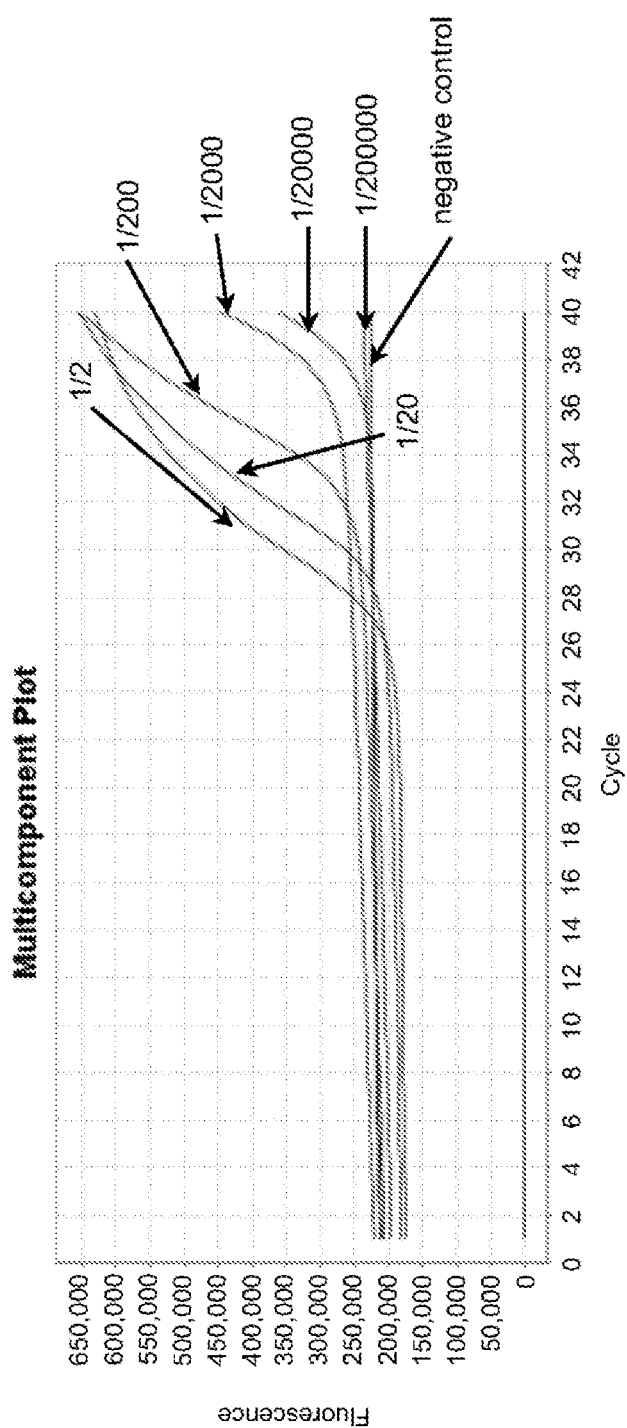
FIGS. 4A and 4B are graphs depicting results of example nucleic acid amplification reactions described in Example 2.
Figure 4B:
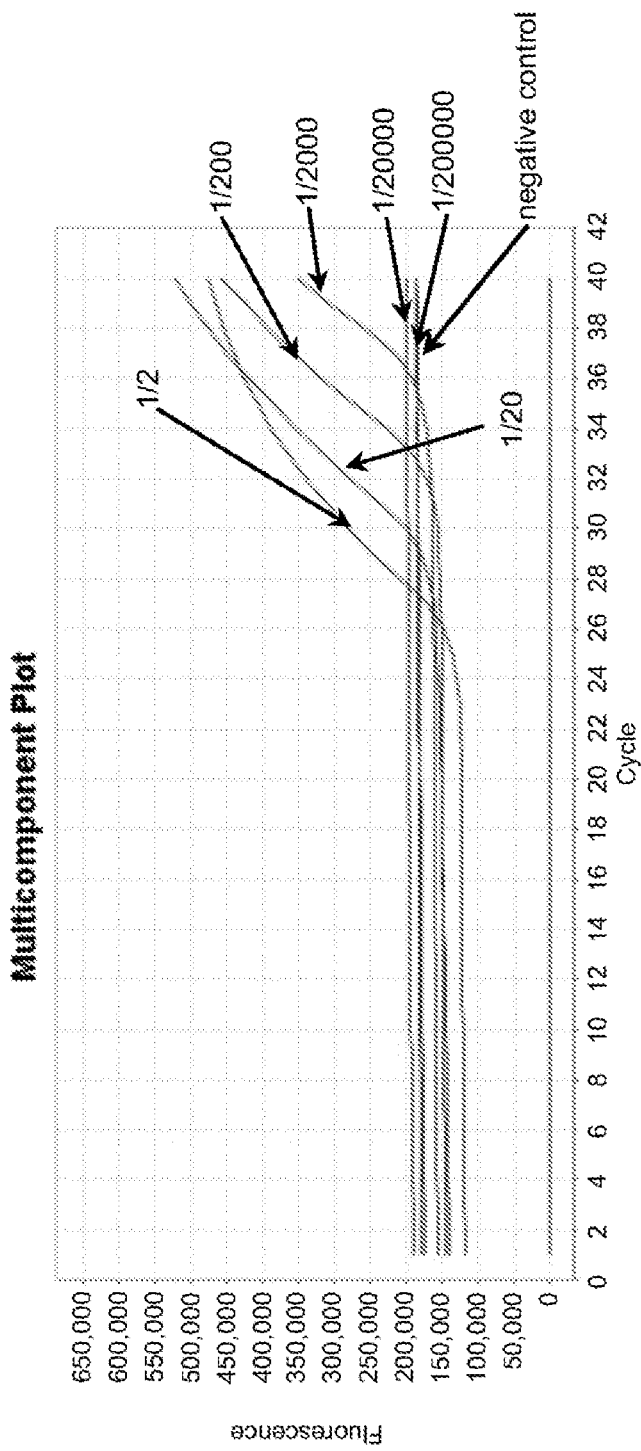
Figure 5:
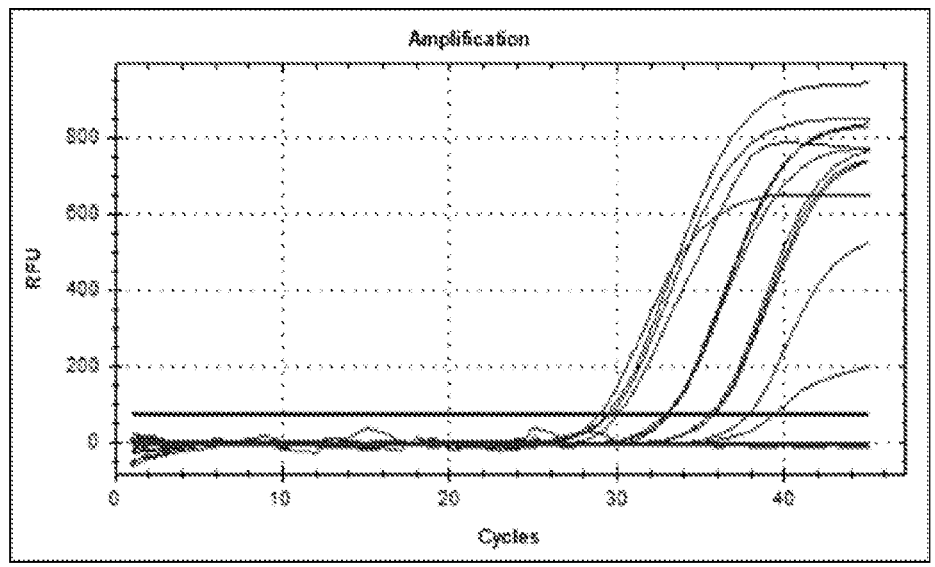
FIG. 5 is a graph depicting results of example nucleic acid amplification reactions described in Example 3.

Amplification results for H3N2 are graphically depicted in FIG. 2 (FIG. 2A corresponds to the various viral standard samples, FIG. 2B corresponds to the biological samples) and amplification results for H1N1 (2007) are graphically depicted in FIG. 3 (FIG. 3A corresponds to the various viral standard samples, FIG. 3B corresponds to the biological samples). Recorded fluorescence of the FAM dye is plotted against the number of cycles.

As shown in FIG. 2A, each of the H3N2 viral standard samples showed detectable signal over the negative control, with Ct values ranging from 18 to 32. As shown in FIG. 2B, each of the viral H3N2 biological samples showed detectable signal over the negative control, with Ct values ranging from 29-35.

As shown in FIG. 3A and with the exception of the 1/20000 dilution, each of the H1N1 (2007) viral standard samples showed detectable signal over the negative control, with Ct values ranging from 24-35. As shown in FIG. 3B, each of the H1N1 (2007) biological samples showed detectable signal over the negative control, with Ct values ranging from 28-35.

In general, the data shown in FIG. 2 and FIG. 3 indicate that the tested viruses could be detected, via amplified DNA product, with good sensitivity, at concentrations as low as 50 IU/mL and over a 4-log concentration range with cycle threshold values of no more than about 40. Moreover, data also indicate that detection of viral RNA obtained from a biological sample obtained from a subject could also be detected in a similar fashion.

Example 2: Amplification and Detection of Viral Nucleic Acid in Different Buffer Systems Amplification and detection experiments were performed to compare results obtained from using different buffer systems for amplification. A set of experiments was conducted for two different buffer systems, S1 and S2. The S1 buffer included a zwitterionic buffering agent and BSA, and the S2 buffer included zwitterionic buffering agent and Sodium hydroxide. Experiments for each buffer were completed using a set of H5N1 influenza virus standard samples obtained as serial dilutions of a stock solution comprising the virus. The concentration H5N1 was $10^6$ IU/mL. Dilutions of 1/2, 1/20, 1/200, 1/2000, 1/20000, 1/200000, and a negative control were subject to amplification.

Five microliters of each sample were combined in a 25 μL reaction tube with reagents necessary to conduct reverse transcription of the viral RNA and reagents necessary to complete amplification of the complementary DNA obtained from reverse transcription (e.g., parallel nucleic acid amplification). The reagents necessary to conduct reverse transcription and DNA amplification included reverse transcriptases, a DNA polymerase, dNTPs, and the appropriate S1 or S2 buffer. Moreover, the reaction tubes also included a TaqMan probe comprising a FAM dye for detection of amplified DNA product. To generate amplified DNA product, each reaction mixture incubated according to a protocol of denaturing and elongation conditions comprising 5 min at 95° C., followed by 20 min at 45° C., followed by 2 min at 95° C., and followed by 40 cycles of 5 seconds at 95° C. and 30 seconds at 55° C. in a real-time PCR thermocycler. Detection of amplified product occurred during incubations.

Amplification results for buffer system S1 are graphically depicted in FIG. 4A and amplification results for buffer system S2 were graphically depicted in FIG. 4B. Recorded fluorescence of the FAM dye is plotted against the number of cycles.

As shown in FIG. 4A each of the viral standard samples amplified in buffer system S1 showed detectable signal over the negative control, with Ct values ranging from 25 to 36. As shown in FIG. 4B, each of the viral standard samples amplified in buffer S2 showed detectable signal over the negative control, with Ct values ranging from 25-35.

In general, the data shown in FIG. 4 indicate that the tested virus could be detected, via amplified DNA product, with good sensitivity, at concentrations as low as 50 IU/mL and over a 5-log concentration range with cycle threshold values of no more than about 40. Moreover, data also indicate that similar amplification results can be obtained with different buffer systems.

Example 3: Amplification and Detection of Hepatitis B Virus (HBV) in Plasma Samples Amplification experiments were performed to determine the robustness of an amplification method to detect target nucleic acid in a biological sample. Diluted human blood plasma samples comprising hepatitis B virus (HBV) at various concentrations (e.g., 50 infective units per milliliter (IU/mL), 200 IU/mL, 2000 IU/mL, 20000 IU/mL) were each subject to amplification reactions. HBV is a DNA virus that replicates via an RNA intermediate. HBV is detectable via direct PCR of the DNA virus. Multiple samples (n=2-4) were tested for each concentration in additional to multiple samples of a negative control (e.g., plasma not comprising HBV).

2.5 μL of each sample with reagents necessary to conduct reverse transcription of the RNA and reagents necessary to complete amplification of the complementary DNA obtained from reverse transcription (e.g., parallel nucleic acid amplification) in a 50 μL reaction tube to obtain a reaction mixture. The reagents necessary to conduct reverse transcription and DNA amplification were supplied as a commercially available pre-mixture (e.g., Qiagen One-Step RT-PCR or One-Step RT-qPCR kit) comprising reverse transcriptases (e.g., Sensiscript and Omniscript transcriptases), a DNA Polymerase (e.g., HotStarTaq DNA Polymerase), and dNTPs. Moreover, the mixture also included a TaqMan probe comprising a FAM dye for detection of amplified DNA product. Also, the reaction mixture included a zwitterionic buffering agent and a uracil-DNA glycosylase (UNG) enzyme to prevent inhibitory effects of amplification inhibitors found in plasma. Each reaction mixture was incubated according to a protocol of denaturing and elongation conditions comprising 1 min at 94° C., followed by 10 min at 50° C., followed by 2 min at 94° C., and followed by 50 cycles of 5 seconds at 94° C. and 35 seconds at 58° C. in a real-time PCR thermocyler. Detection of amplified product occurred during incubations.

Amplification results are graphically depicted in FIG. 5 and determined Ct values tabulated in Table 1. Recorded relative fluorescence units (RFU) of the FAM dye is plotted against the number of cycles in FIG. 5. As shown in FIG. 5 and Table 1, HBV could be detected at each concentration tested with cycle threshold values ranging from 28.99 to 39.39. In general, higher concentration samples corresponded to lower cycle threshold values.

In general, the data shown in FIG. 5 and Table 1 indicate HBV could be detected, via amplified DNA product, with good sensitivity, at concentrations as low as 50 IU/mL (the lowest tested) with cycle threshold values of no more than about 40. While the highest concentration tested (20000 IU/mL) was 400 times more concentrated than the lowest concentration tested (50 IU/mL), cycle threshold values were only about 25% higher for lower concentrations, indicating that the amplification scheme was generally robust.

TABLE 1

Ct Results from Experiments in Example 3

| Sample # | IU/mL | Ct |
|---|---|---|
| 1 | 2000 | 33.09 |
| 2 | 50 | 39.39 |
| 3 | 2.00E+04 | 29 |
| 4 | 2000 | 32.97 |
| 5 | 200 | 35.51 |
| 6 | 2000 | 33.07 |
| 7 | 2.00E+04 | 30.03 |
| 8 | 200 | 35.78 |
| 9 | 50 | 37.91 |
| 10 | 2.00E+04 | 29.37 |
| 11 | 200 | 35.73 |
| 12 | 2.00E+04 | 28.99 |

Example 4: Pre-Heating a Biological Sample Prior to Amplification of Nucleic Acid in the Biological Sample and Series of Amplification Reactions Amplification experiments were conducted to determine the effect of pre-heating a biological sample on detection sensitivity and also to determine the effect of using multiple series of amplification reactions on detection sensitivity.

Twenty 25 µL reaction mixtures were prepared, with each reaction mixture comprising 1 µL of a pathogenic species, reagents necessary to complete appropriate nucleic acid amplification reactions (e.g., reverse transcription and DNA amplification for RNA species, and DNA amplification for DNA species), and a TaqMan probe comprising a FAM dye. Four of the reaction mixtures contained H1N1 (2007) (i.e., an RNA virus four of the reaction mixtures contained H3N2 (i.e., an RNA virus), four of the reaction mixtures contained H1N1 (2009), four of the reaction mixtures contained tuberculosis (TB) (i.e., a bacterial sample), and four of the reaction mixtures contained Aleutian disease virus (ADV) (i.e., a DNA virus). H1N1 (2007), H1N1 (2009), H3N2, and ADV pathogenic species were from oropharyngeal swabs obtained from subjects. TB was obtained from a bacterium stock.

Various combinations of pre-heating and amplification protocols were utilized and are summarized in Table 2. For the first reaction mixture for each pathogenic species, the pathogenic species was pre-heated 10 min at 95° C. prior to being added to the reaction mixture. After addition of the pathogenic species to the reaction mixture, the reaction mixture was incubated according to a protocol of denaturing and elongation conditions comprising 2 minutes at 95° C. followed by 40 cycles of 5 seconds at 95° C. and 30 seconds at 55° C. in a real-time PCR thermocycler. Detection of amplified product occurred during incubations. These reaction mixtures are referred to as PH-1 mixtures.

For the second reaction mixture for each pathogenic species, the pathogenic species was pre-heated 30 min at 50° C. prior to being added to the reaction mixture. After addition of the pathogenic species to the reaction mixture, the reaction mixture was incubated according to a protocol of denaturing and elongation conditions comprising 2 minutes at 95° C. followed by 40 cycles of 5 seconds at 95° C. and 30 seconds at 55° C. in a real-time PCR thermocycler. Detection of amplified product occurred during incubations. These reaction mixtures are referred to as PH-2 mixtures.

For the third reaction mixture for each pathogenic species, the pathogenic species was not pre-heated prior to being added to the reaction mixture. These reaction mixtures incubated according to a protocol of denaturing and elongation conditions comprising 1 min at 95° C., followed by 10 minutes at 55° C., followed by 2 minutes at 95° C., followed by 40 cycles of 5 seconds at 95° C. and 30 seconds at 55° C. in a real-time PCR thermocycler. Detection of amplified product occurred during incubations. These reaction mixtures are referred to as PTC-1 mixtures.

For the fourth reaction mixture for each pathogenic species, the pathogenic species was not pre-heated prior to being added to the reaction mixture. These reaction mixtures were subjected to a protocol comprising a plurality of series of amplification reactions, with each series comprising multiple cycles of denaturing and elongation conditions. Reaction mixtures were incubated according to such a protocol comprising 1 minute at 95° C., followed by 10 cycles of Series 1 (95° C. for 5 seconds, 20 seconds of 60-50° C., stepping down 1° C./cycle, and 60° C. for 10 seconds), followed by 2 minutes 95° C. for 2 minutes, followed by 40 cycles of Series 2 (95° C. for 5 seconds, 55° C. for 30 seconds) in a real-time PCR thermocycler. Series 1 and Series 2 differ in their elongation temperature and elongation duration. Detection of amplified product occurred during incubations. These reaction mixtures are referred to as PTC-2 mixtures.

TABLE 2

Experimental Conditions of Example 4

| Reaction Mixture Type | Protocol |
|---|---|
| PH-1 | 95° C. 10 minute preheating on pathogenic species before adding to the reaction mixture, then 95° C. for 2 minutes, (95° C. for 5 seconds, 55° C. for 30 seconds) × 40 cycles |
| PH-2 | 50° C. 30 minute preheating on pathogenic before adding to the reaction mixture, then 95° C. for 2 minutes, (95° C. for 5 seconds, 55° C. for 30 seconds) × 40 cycles |
| PTC-1 | 95° C. for 1 minute, 55° C. for 10 minutes, then 95° C. for 2 minutes, (95° C. for 5 seconds, 55° C. for 30 seconds) × 40 cycles |
| PTC-2 | 95° C. for 1 minute, (95° C. for 5 seconds, 60-50° C., stepping down 1° C./cycle, for 20 seconds, 60° C. for 10 seconds) × 10 cycles, then 95° C. for 2 minutes, (95° C. for 5 seconds, 55° C. for 30 seconds) × 40 cycles |

Figure 6A:
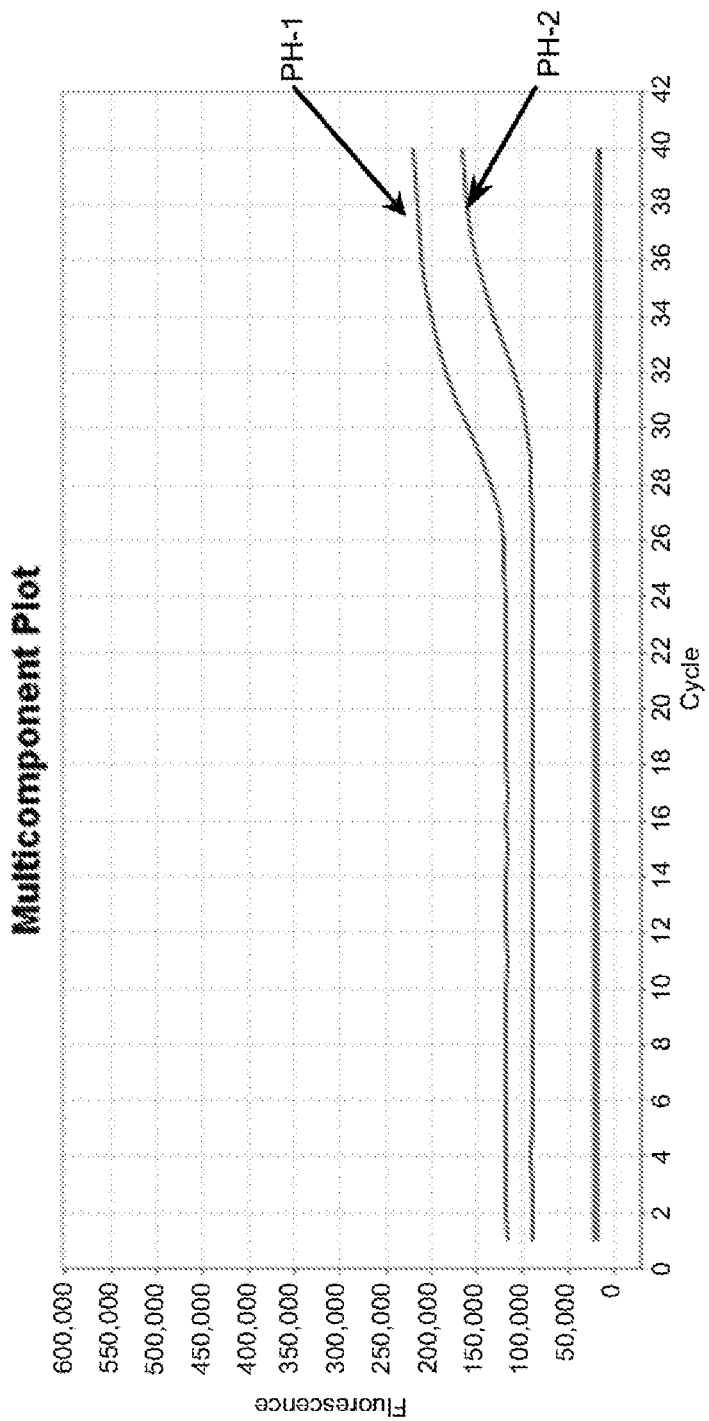
FIGS. 6A and 6B are graphs depicting results of example nucleic acid amplification reactions described in Example 4.
Figure 6B:
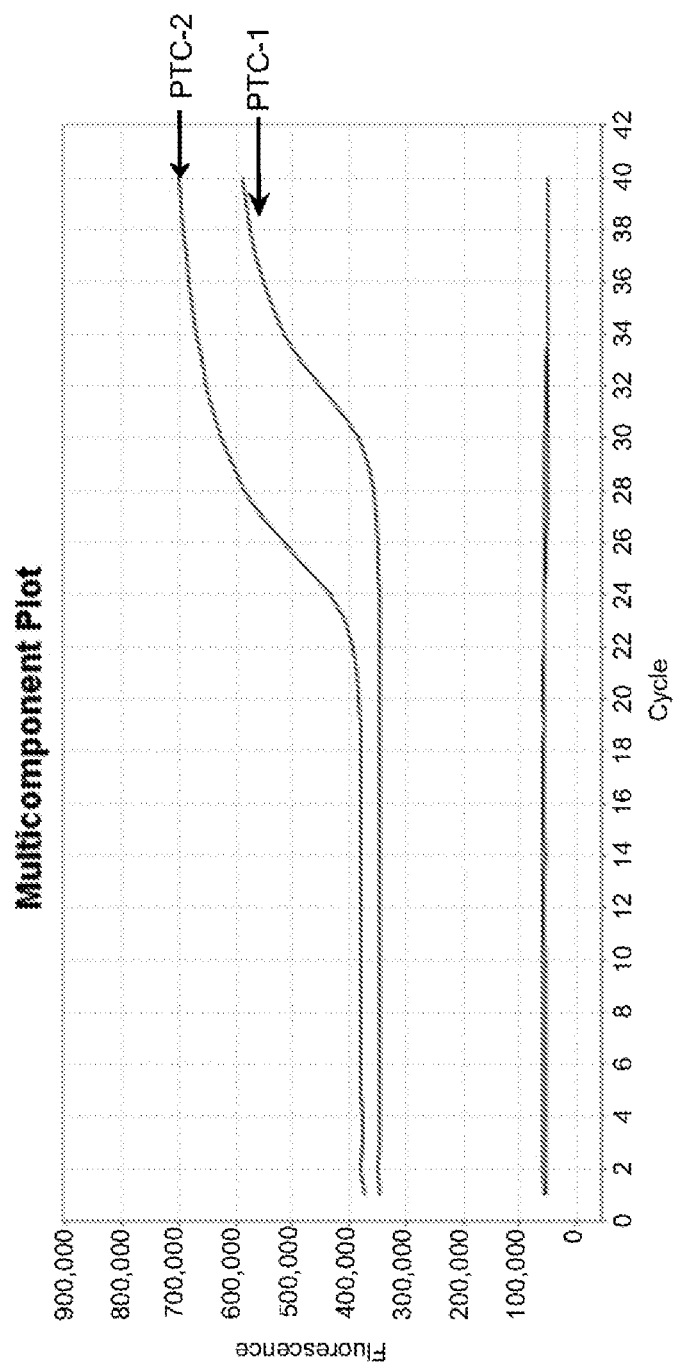
Figure 7A:
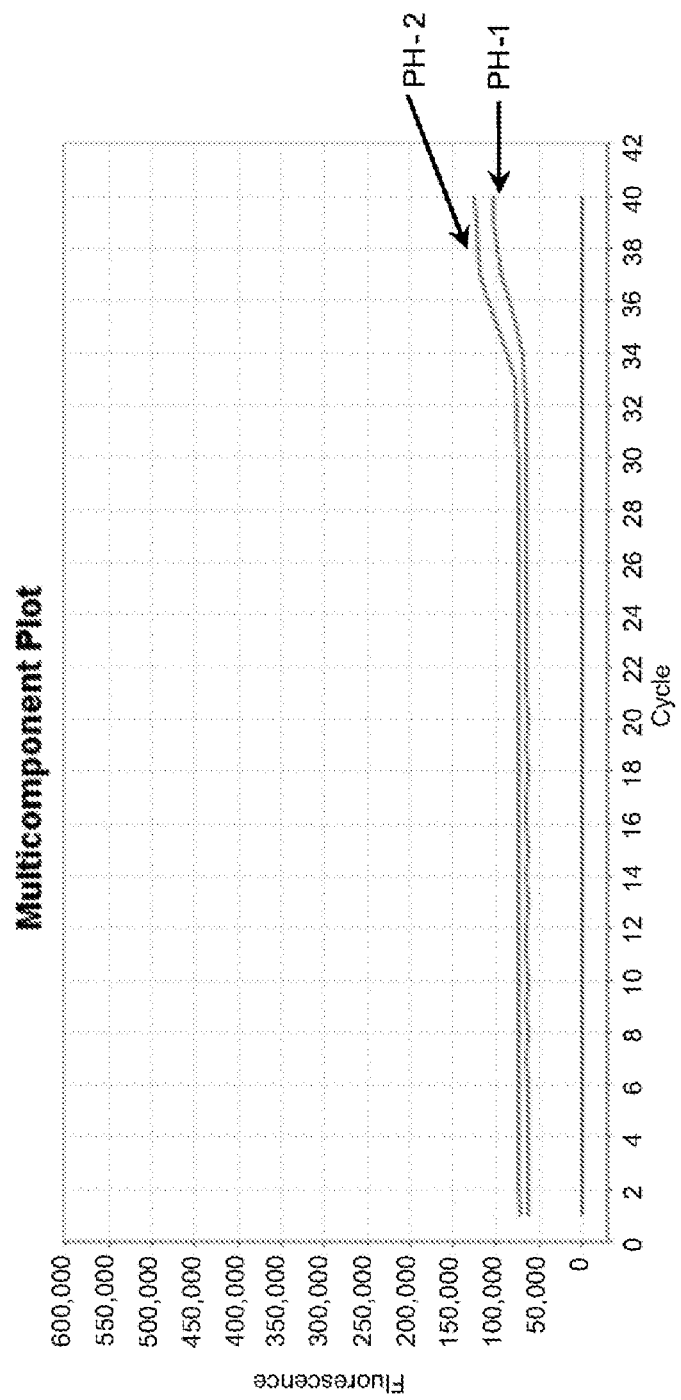
FIGS. 7A and 7B are graphs depicting results of example nucleic acid amplification reactions described in Example 4.
Figure 7B:
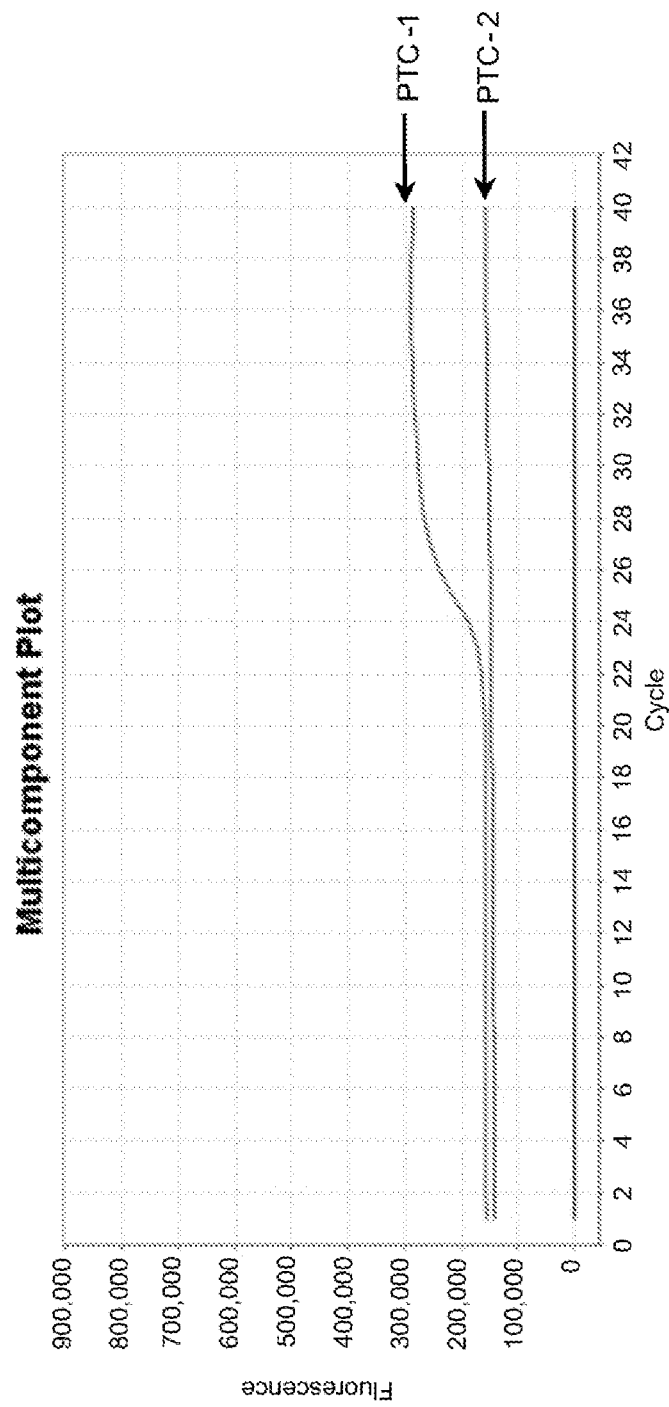
Figure 8A:
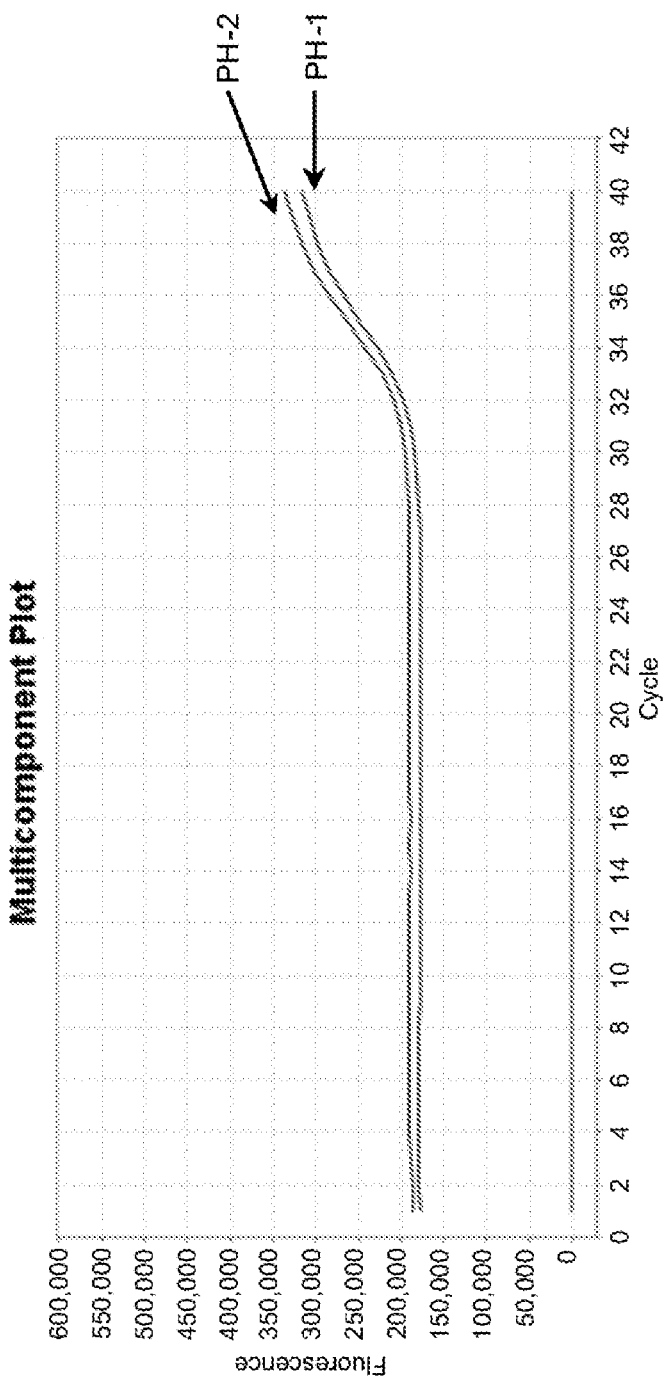
FIGS. 8A and 8B are graphs depicting results of example nucleic acid amplification reactions described in Example 4.
Figure 8B:
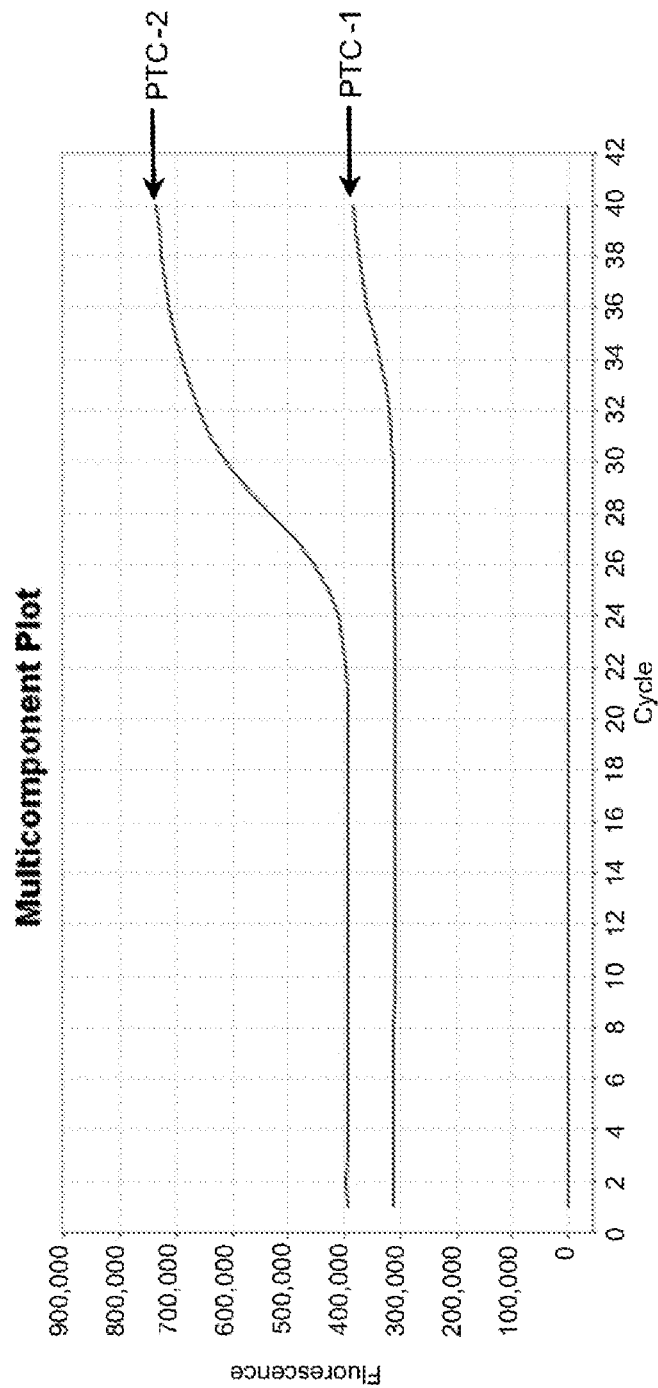
Figure 9A:
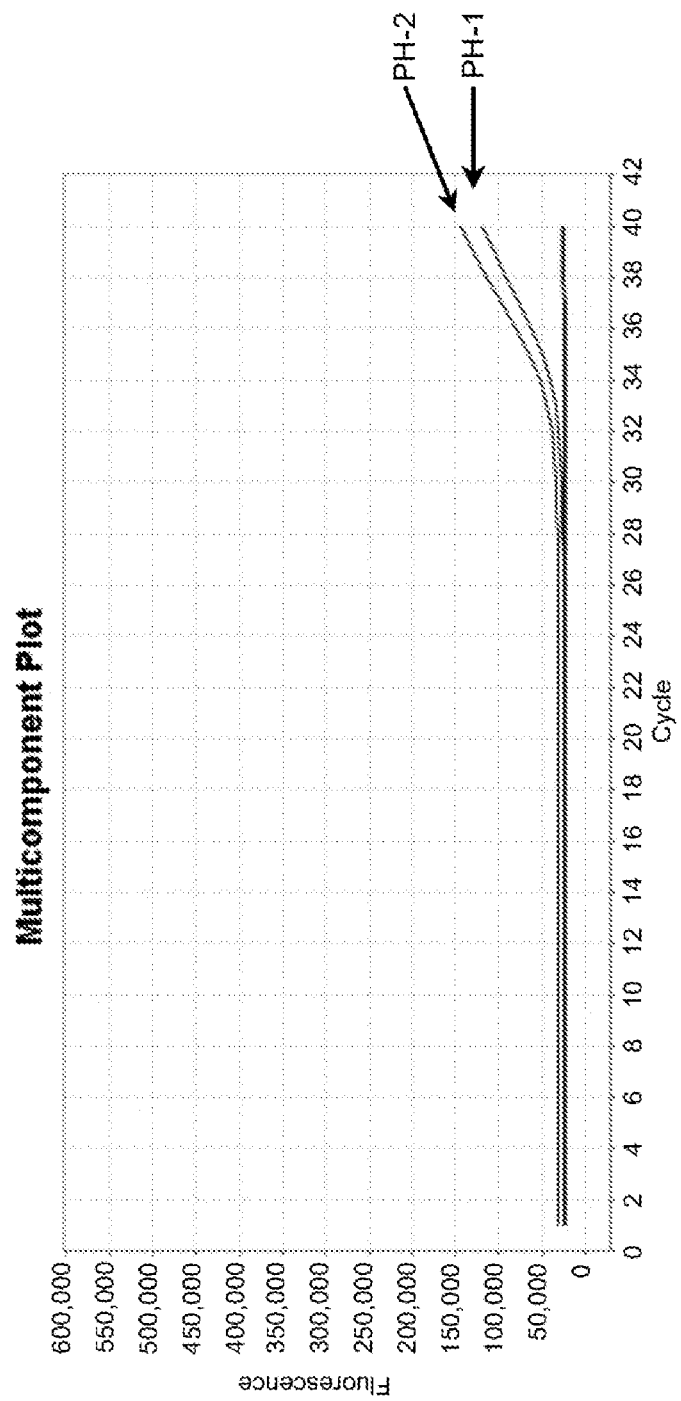
FIGS. 9A and 9B are graphs depicting results of example nucleic acid amplification reactions described in Example 4.
Figure 9B:
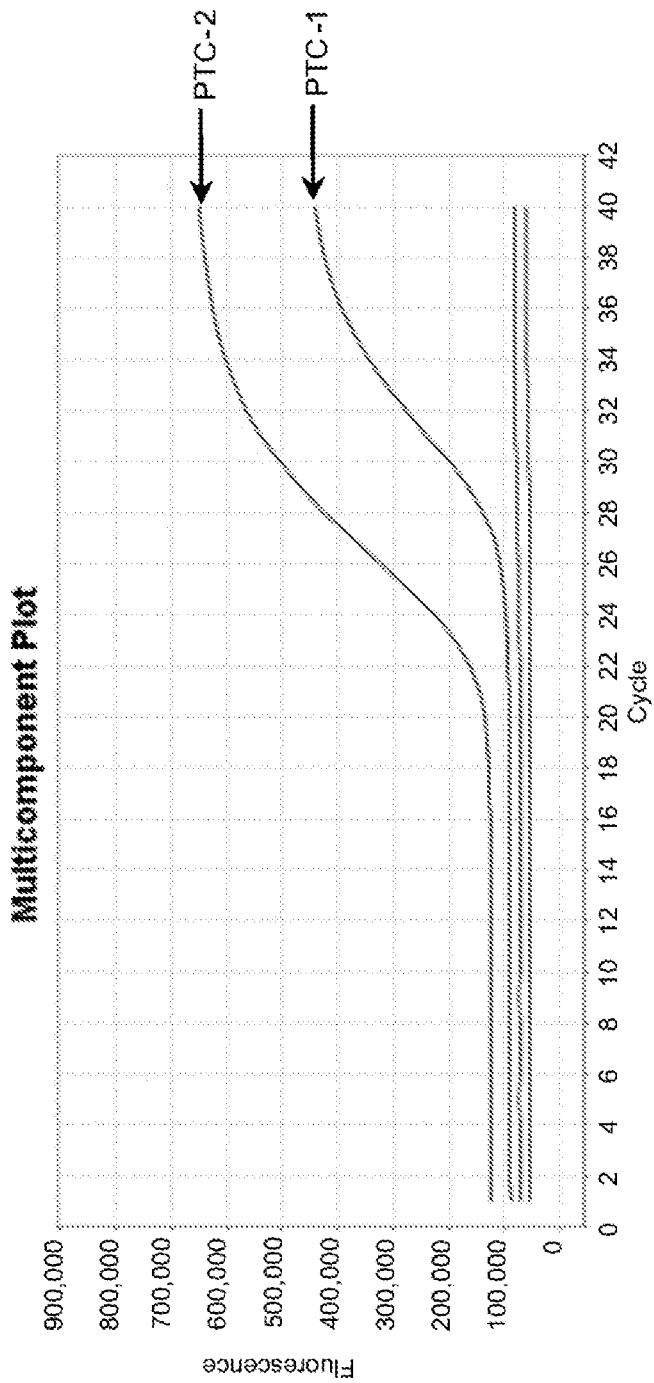
Figure 10A:
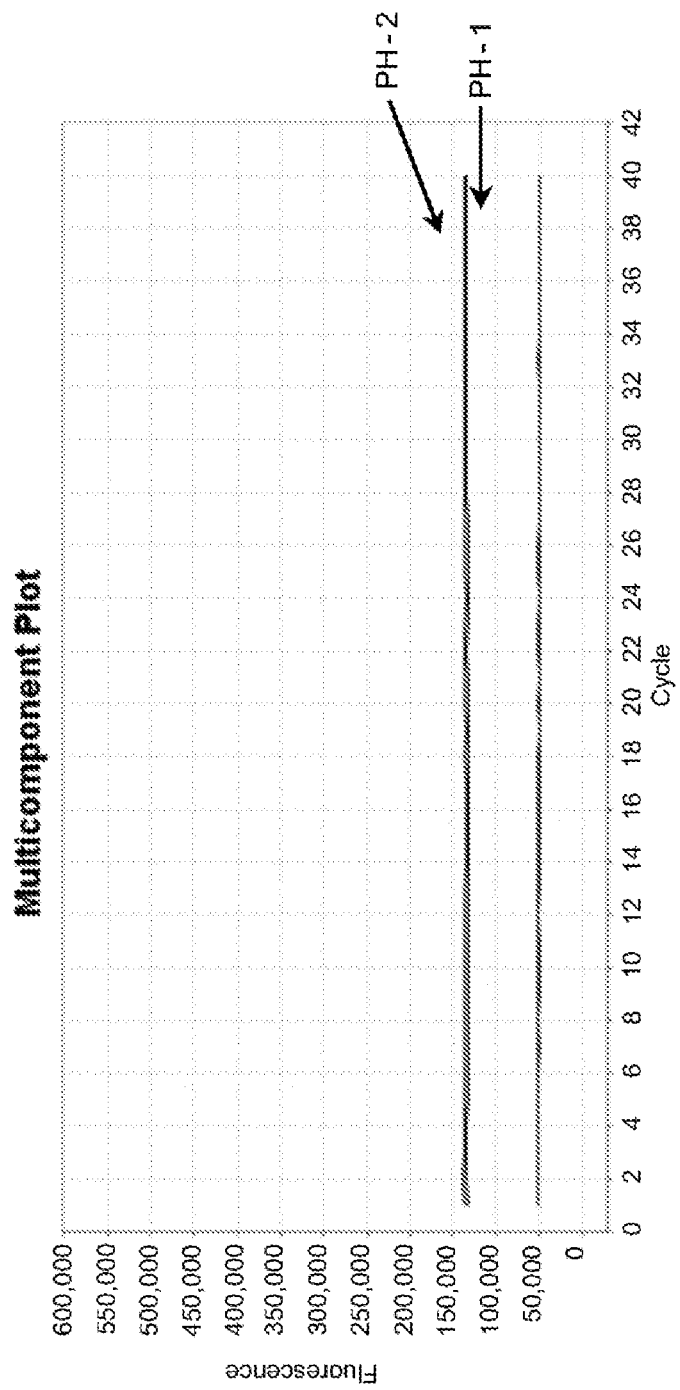
FIGS. 10A and 10B are graphs depicting results of example nucleic acid amplification reactions described in Example 4.
Figure 10B:
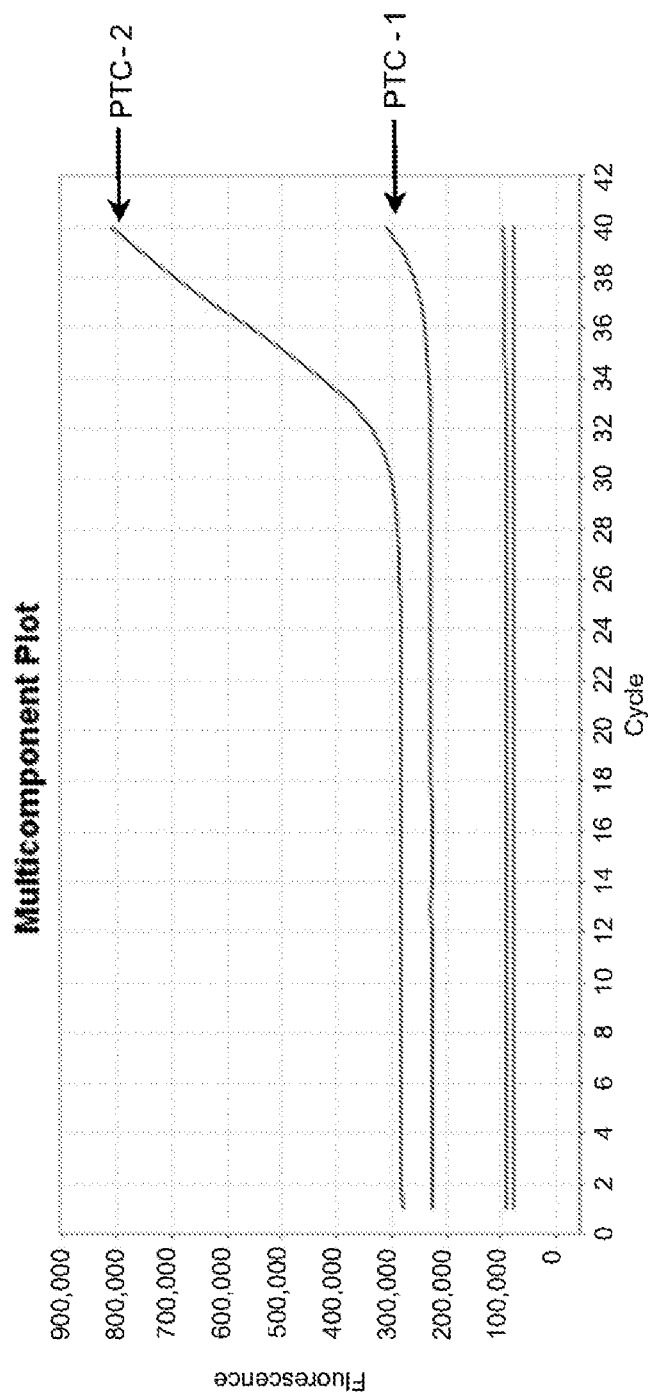

Results from each pathogenic species are graphically depicted in FIG. 6 (H1N1 (2007), FIG. 7 (H3N2), FIG. 8 (H1N1 (2009)), FIG. 9 (TB), and FIG. 10 (ADV). Item A in each of FIGS. 6-10 represents results obtained for reaction mixtures PH-1 and PH-2, whereas Item B in each of FIGS. 6-10 represents results obtained for reaction mixture PTC-1 and PTC-2. Ct values determined for each experiments are summarized in Table 3. Ct values could not be determined for PH-1 and PH-2 ADV reaction mixtures, commensurate with the data shown in FIG. 10A.

According to data shown in Table 3, Ct values between were fairly similar between PH-1 and PH-2 reaction mixtures, indicating that a pathogenic species (or biological sample comprising a pathogenic species) could be pre-heated at a range of conditions to obtain similar detection sensitivity. Moreover, PTC-1 reaction mixtures had Ct values similar to those determined for PH-1 and PH-2 reaction mixtures. PTC-1 and PH-1/PH-2 protocols were similar, except that PTC-1 did not include a pre-heating step. Thus, a comparison of PTC-1 data with PH-1/PH-2 data indicates that pre-heating of a pathogenic species prior to providing it to a reaction mixture may not be necessary for obtaining results with good sensitivity. However, in some cases with TB and ADV samples, pre-heating can be even worse than without pre-heating.

However, for all pathogenic species tested, PTC-2 Ct values were lower than any of PH-1, PH-2, or PTC-1. A comparison of PTC-1 and PTC-2 data indicate that subjecting reaction mixtures to a multiple series of amplification reactions, with each series comprising multiple cycles of denaturing and elongation conditions, may improve detection sensitivity.

TABLE 3

Ct Results from Experiments in Example 4

| Type | Sample | PH-1 (Ct) | PH-2 (Ct) | PTC-1 (Ct) | PTC-2 (Ct) |
|---|---|---|---|---|---|
| RNA virus | H1N1(2007) | 27 | 30 | 28 | 22 |
| RNA virus | H3N2 | 34 | 33 | 32 | 23 |

TABLE 3-continued

Ct Results from Experiments in Example 4

| Type | Sample | PH-1 (Ct) | PH-2 (Ct) | PTC-1 (Ct) | PTC-2 (Ct) |
|---|---|---|---|---|---|
| RNA virus | H1N1(2009) | 32 | 32 | 32 | 24 |
| DNA bacteria | TB | 34 | 32 | 26 | 20 |
| DNA virus | ADV | — | — | 36 | 30 |

Example 5: Multiplexing Samples

Amplification and detection experiments were performed to benchmark various amplification protocols and to determine whether multiplexing could be achieved. Biological samples comprising RNA (e.g., H1N1 (2007), H1N1 (2009), H3N2) or DNA (e.g., ADV, human bocavirus (HBoV) viral pathogens or DNA bacterial pathogens (e.g., TB) were subject to various amplification conditions. Each biological sample was obtained directly from a subject via an oropharyngeal swab, except for TB samples which were from a bacterium stock. One microliter of each sample was combined in a 25 µL reaction tube with reagents necessary to conduct nucleic acid amplification and to detect amplified product as described herein to obtain a reaction mixture.

To assess the multiplexing capabilities of an amplification protocol, three reaction mixtures, each comprising one of H3N2, ADV, or a mixture of H3N2 and ADV were incubated according to an amplification protocol comprising 2 min at 94° C., 20 min at 45° C., 1 min at 94° C., followed by 50 cycles of 5 seconds at 94° C. and 35 seconds at 55° C. in a real time PCR thermocycler. Detection of amplified product occurred during incubations.

Figure 11:
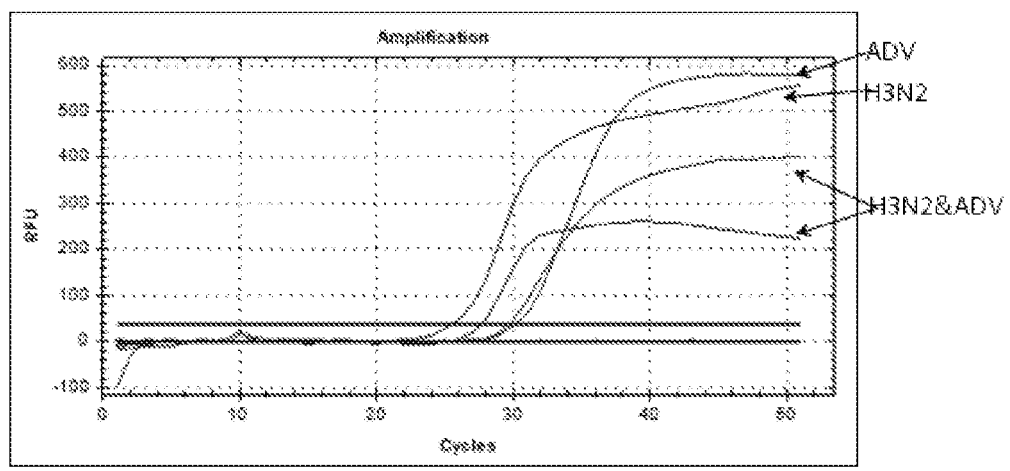
FIG. 11 is a graph depicting results of example nucleic acid amplification reactions described in Example 5.

Results of the experiments are graphically depicted in FIG. 11 and shown below in Table 4. As shown in FIG. 11, both H3N2 and TB could be detected similarly when in combination or in the absence of the other. In the absence of ADV, a Ct value of 26.03 was recorded for the H3N2 reaction mixture and in the absence of H3N2, a Ct value of 30.5 was recorded for the ADV reaction mixture. When both of H3N2 and ADV were combined into a single reaction mixture, Ct values of 26 (H3N2) and 30 (ADV) were obtained. Ct values were nearly identical for the combined reaction mixture when compared to the single component reaction mixtures. Results indicate that multiplexing is achievable with good sensitivity and that both RNA and DNA species can be detected.

TABLE 4

Results from H3N2 and ADV Multiplexing Experiment in Example 5

| Type | Sample | Ct |
|---|---|---|
| RNA virus | H3N2 | 26.03 |
| DNA virus | ADV | 30.5 |
| RNA & DNA virus | H3N2 & ADV | 26(H3N2) & 30(ADV) |

In another experiment to assess the multiplexing capabilities of an amplification protocol, three reaction mixtures, each comprising one of H3N2, TB, or a mixture of H3N2 and TB were incubated according to an amplification protocol comprising 2 min at 95° C., followed by 40 cycles of 5 seconds at 95° C. and 30 seconds at 55° C. in a real time PCR thermocycler. Detection of amplified product occurred during incubations.

Figure 12:
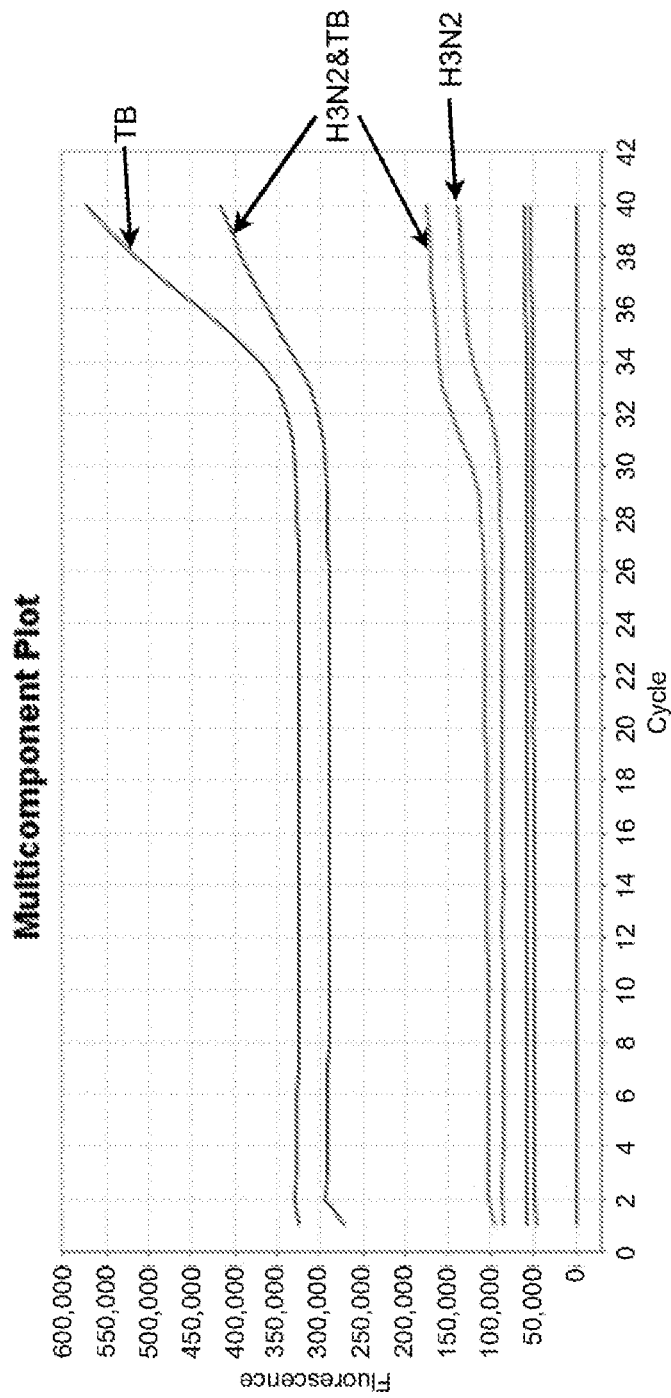
FIG. 12 is a graph depicting results of example nucleic acid amplification reactions described in Example 5.

Results of the experiments are graphically depicted in FIG. 12 and shown below in Table 5. As shown in FIG. 12, both H3N2 and TB could be detected similarly when in combination or in the absence of the other. In the absence of TB, a Ct value of 32 was recorded for the H3N2 reaction mixture and in the absence of H3N2, a Ct value of 32 was recorded for the TB reaction mixture. When both of H3N2 and TB were combined into a single reaction mixture, Ct values of 29 (H3N2) and 30 (TB) were obtained. Ct values were similar for the combined reaction mixture when compared to the single component reaction mixtures. Results indicate that multiplexing is achievable with good sensitivity and that both RNA and DNA species can be detected in a multiplexing scheme.

TABLE 5

Results from H3N2 and TB Multiplexing Experiment in Example 5

| Type | Sample | Ct |
|---|---|---|
| RNA virus | H3N2 | 32 |
| DNA virus | TB | 32 |
| RNA & DNA virus | H3N2 & TB | 29(H3N2) & 30(TB) |

Example 6: Benchmarking Multiple Series of Amplification Reactions

Amplification and detection experiments were performed to benchmark various amplification protocols comprising multiple series of amplification reactions. Biological samples comprising RNA (e.g., H1N1 (2007), H1N1 (2009), H3N2) or DNA (e.g., ADV, human bocavirus (HBoV) viral pathogens or DNA bacterial pathogens (e.g., TB) were subject to various amplification conditions. Each biological sample was obtained directly from a subject via an oropharyngeal swab, except for TB samples which were from a bacterium stock. One microliter of each sample was combined in a 25 µL reaction tube with reagents necessary to conduct nucleic acid amplification and to detect amplified product as described herein to obtain a reaction mixture.

In one set of experiments, amplification mixtures were subjected to an amplification protocol comprising two series of amplification reactions, each series comprising different denaturation and elongation conditions. Six reaction mixtures (two comprising H3N2, two comprising ADV, two comprising HBoV) were incubated according to an amplification protocol comprising 1 second at 94° C., followed by 11 cycles of Series 1 (1 second at 94° C. and 10 seconds at 45° C.), followed by 1 minute at 95° C., followed by 40 cycles of Series 2 (5 seconds at 95° C. and 30 seconds at 55° C.) in a real time PCR thermocycler. Detection of amplified product occurred during incubations.

Results of the experiments are shown below in Table 6. As shown in Table 6, determined Ct values ranged from 8.35 to 23. Results indicate that protocols comprising multiple series of amplification reactions can be useful in achieving good sensitivity. Moreover, results also indicate that both RNA and DNA species can be detected with protocols comprising multiple series of amplification reactions.

TABLE 6

Results from H3N2, ADV, and HBoV Experiment in Example 6

| Type | Sample | Ct |
|---|---|---|
| RNA virus | H3N2-1 | 17 |
| RNA virus | H3N2-2 | 20 |
| DNA virus | ADV-1 | 18.8 |
| DNA virus | ADV-2 | 23 |
| DNA virus | HBoV-1 | 8.35 |
| DNA virus | HBoV-2 | 18.37 |

In another set of experiments, amplification mixtures were subjected to an amplification protocol comprising three series of amplification reactions, the series differing from the others with respect to their denaturation and/or elongation condition. Five reaction mixtures (one comprising sH1N1 (2007), one comprising H3N2, one comprising pH1N1 (2009), one comprising ADV, and one comprising TB) were incubated according to an amplification protocol comprising 1 minute at 94° C., followed by 5 cycles of Series 1 (5 seconds at 94° C. and 30 seconds at 60-50° C. stepped down 1° C./cycle), followed 5 cycles of Series 2 (5 seconds at 94° C. and 30 seconds at 50° C.), followed by 2 minutes at 95° C., followed by 40 cycles of Series 3 (5 seconds at 95° C. and 30 seconds at 55° C.) in a real time PCR thermocycler. Detection of amplified product occurred during incubations.

Results of the experiments are shown below in Table 7. As shown in Table 7, determined Ct values ranged from 20 to 30. Results indicate that protocols comprising multiple series of amplification reactions can be useful in achieving good sensitivity. Moreover, results also indicate that both RNA and DNA species can be detected with protocols comprising multiple series of amplification reactions.

TABLE 7

Results from sH1N1(2007), H3N2, pH1N1(2009), ADV, and TB Experiment in Example 6

| Type | Sample | Ct |
|---|---|---|
| RNA virus | sH1N1(2007) | 22 |
| RNA virus | H3N2 | 23 |
| RNA virus | pH1N1(2009) | 24 |
| DNA virus | ADV | 30 |
| DNA bacteria | TB | 20 |

Example 7: Benchmarking Multiple Series of Amplification Reactions

Amplification and detection experiments were performed to benchmark various amplification protocols comprising multiple series of amplification reactions. Biological samples comprising H3N2 were subject to various amplification conditions. Each biological sample was obtained directly from a subject via an oropharyngeal swab. One microliter of each sample was combined in a 25 µL reaction tube with reagents necessary to conduct nucleic acid amplification and to detect amplified product as described herein to obtain a reaction mixture.

Amplification mixtures were subjected to amplification protocols, some comprising one of three different first series of amplification reactions and the same second series, the three first series comprising different denaturation and elongation conditions than the second series. Each of first series and the second series comprised multiple cycles. Another experiment was conducted without a first series, comprising only the second series. In a real time PCR thermocycler, each of four reaction mixtures comprising H3N2 were incubated according to one of the amplification protocols shown below in Table 8:

TABLE 8

Experimental Protocols in Example 7

| Reaction Mixture | Protocol |
|---|---|
| 1 | 94° C. for 1 minute, (Series 1A -- 94° C. for 1 second, 45° C. for 2 minutes) × 5 cycles, 95° C. for 1 minute, (Series 2 -- 95° C. for 5 seconds, 55° C. for 30 seconds) × 50 cycles |
| 2 | 80° C. for 2 minutes, (Series 1B -- 80° C. for 1 second, 45° C. for 2 minutes) × 5 cycles, 95° C. for 1 minute, (Series 2 -- 95° C. for 5 seconds, 55° C. for 30 seconds) × 50 cycles |
| 3 | 80° C. for 2 minutes, 45° C. for 30 minutes, 95° C. for 1 minute, (Series 2 -- 95° C. for 5 seconds, 55° C. for 30 seconds) × 50 cycles |
| 4 | 94° C. for 1 second, (Series 1C -- 94° C. for 1 second, 45° C. for 30 seconds) × 50 cycles, (Series 2 -- 95° C. for 5 seconds, 55° C. for 30 seconds) × 50 cycles |

Figure 13:
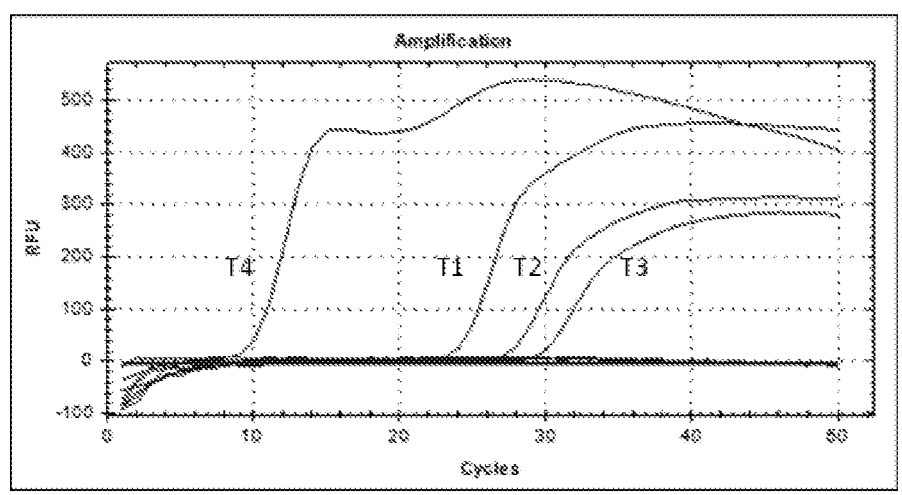
FIG. 13 is a graph depicting results of example nucleic acid amplification reactions described in Example 7.

Results of the experiments are graphically depicted in FIG. 13 and tabulated below in Table 9. As shown in FIG. 13, reaction mixture 3 had the highest Ct value (28.59). The others comprising multiple series had lower values ranging from 8.5 to 26.5. Results indicate that protocols comprising multiple series of amplification reactions can be useful in achieving good sensitivity. Moreover, results also indicate that protocols comprising multiple series of amplification reactions may achieve better sensitivity when compared to protocols with only a single series.

TABLE 9

Experimental Results of Example 7

| Reaction Mixture | Ct |
|---|---|
| 1 | 22.97 |
| 2 | 26.5 |
| 3 | 28.59 |
| 4 | 8.5 |

Example 8: Benchmarking Multiple Series of Amplification Reactions

Amplification and detection experiments were performed to benchmark various amplification protocols comprising multiple series of amplification reactions. Biological samples comprising H3N2 were subject to various amplification conditions. Each biological sample was obtained directly from a subject via an oropharyngeal swab. One microliter of each sample was combined in a 25 µL reaction tube with reagents necessary to conduct nucleic acid amplification and to detect amplified product as described herein to obtain a reaction mixture.

Amplification mixtures were subjected to amplification protocols, some comprising one of six first series of amplification reactions and the same second series, the six first series comprising different denaturation and elongation conditions than the second series. Another six experiments were conducted without a first series. In a real time PCR thermocycler, each of twelve reaction mixtures comprising H3N2 were incubated according to one of the amplification protocols shown below in Table 10:

TABLE 10

Experimental Protocols in Example 8

| Reaction Mixture | Protocol |
|---|---|
| 1 | 95° C. for 3 minutes, 45° C. for 5 minutes, 95° C. for 1 minute, (Series 2 -- 95° C. for 5 seconds, 55° C. for 30 seconds) × 40 cycles |
| 2 | 95° C. for 10 minutes, 45° C. for 5 minutes, 95° C. for 1 minute, (Series 2 -- 95° C. for 5 seconds, 55° C. for 30 seconds) × 40 cycles |
| 3 | 95° C. for 3 minutes, 45° C. for 20 minutes, 95° C. for 1 minute, (Series 2 -- 95° C. for 5 seconds, 55° C. for 30 seconds) × 40 cycles |
| 4 | 95° C. for 10 minutes, 45° C. for 20 minutes, 95° C. for 1 minute, (Series 2 -- 95° C. for 5 seconds, 55° C. for 30 seconds) × 40 cycles |
| 5 | 95° C. for 10 minutes, 45° C. for 3 minutes, 95° C. for 1 minute, (Series 2 -- 95° C. for 5 seconds, 55° C. for 30 seconds) × 40 cycles |
| 6 | 45° C. for 20 minutes, 95° C. for 1 minute, (Series 2 -- 95° C. for 5 seconds, 55° C. for 30 seconds) × 40 cycles |
| 7 | 94° C. for 2 minutes, (Series 1A -- 94° C. for 1 second, 45° C. for 10 seconds) × 10 cycles, 95° C. for 1 minute, (Series 2 -- 95° C. for 5 seconds, 55° C. for 30 seconds) × 50 cycles |
| 8 | 94° C. for 10 seconds, (Series 1B -- 94° C. for 1 second, 45° C. for 10 seconds) × 10 cycles, 95° C. for 1 minute, (Series 2 -- 95° C. for 5 seconds, 55° C. for 30 seconds) × 50 cycles |
| 9 | 94° C. for 2 minutes, (Series 1C -- 94° C. for 10 seconds, 45° C. for 20 seconds) × 10 cycles, 95° C. for 1 minute, (Series 2 -- 95° C. for 5 seconds, 55° C. for 30 seconds) × 50 cycles |
| 10 | 94° C. for 10 seconds, (Series 1D -- 94° C. for 10 seconds, 45° C. for 20 seconds) × 10 cycles, 95° C. for 1 minute, (Series 2 -- 95° C. for 5 seconds, 55° C. for 30 seconds) × 50 cycles |
| 11 | 94° C. for 2 minutes, (Series 1E -- 94° C. for 30 seconds, 45° C. for 60 seconds) × 10 cycles, 95° C. for 1 minute, (Series 2 -- 95° C. for 5 seconds, 55° C. for 30 seconds) × 50 cycles |
| 12 | 94° C. for 10 seconds, (Series 1F -- 94° C. for 30 seconds, 45° C. for 60 seconds) × 10 cycles, 95° C. for 1 minute, (Series 2 -- 95° C. for 5 seconds, 55° C. for 30 seconds) × 50 cycles |

Results of the experiments are tabulated below in Table 11. Ct values ranged from 14.53 to 27.28, with reaction mixtures 2-5 having no detected product. Generally speaking, reaction mixtures not subjected to multiple series of amplification reactions had either no detectable product or had higher Ct values than reaction mixtures subjected to multiple series of amplification reaction. Results indicate that protocols comprising multiple series of amplification reactions can be useful in achieving good sensitivity. Moreover, results also indicate that protocols comprising multiple series of amplification reactions may achieve better sensitivity when compared to protocols with only a single series. In some cases, multiple series of amplification reactions may be necessary for producing detectable quantities of amplified product.

TABLE 11

Experimental Results of Example 8

| Reaction Mixture | Ct |
|---|---|
| 1 | 26.03 |
| 2 | — |
| 3 | — |
| 4 | — |
| 5 | — |
| 6 | 27.28 |
| 7 | 21.64 |
| 8 | 19.56 |
| 9 | 17.2 |
| 10 | 14.53 |
| 11 | 19.2 |
| 12 | — |

Example 9: Comparing Results with Purified and Unpurified Sample

Amplification and detection experiments were performed to compare results obtained with purified and unpurified samples. Purified and un-purified biological samples comprising H1N1 were subject an amplification protocol. Each biological sample was obtained directly from a subject via an oropharyngeal swab. One microliter of each sample was combined in a 25 µL reaction tube with reagents necessary to conduct nucleic acid amplification and to detect amplified product as described herein to obtain a reaction mixture. Three reaction mixtures were generated, with two of the reaction mixtures comprising sample purified by one of column purification or magnetic purification. The third reaction mixture comprised unpurified sample.

The reaction mixtures were incubated according to an amplification protocol comprising 2 minutes at 94° C., 20 minutes at 45° C., 1 minute at 94° C., followed by 50 cycles of 5 seconds at 94° C. and 35 seconds at 55° C. in a real time PCR thermocycler. Detection of amplified product occurred during incubations.

Figure 14:
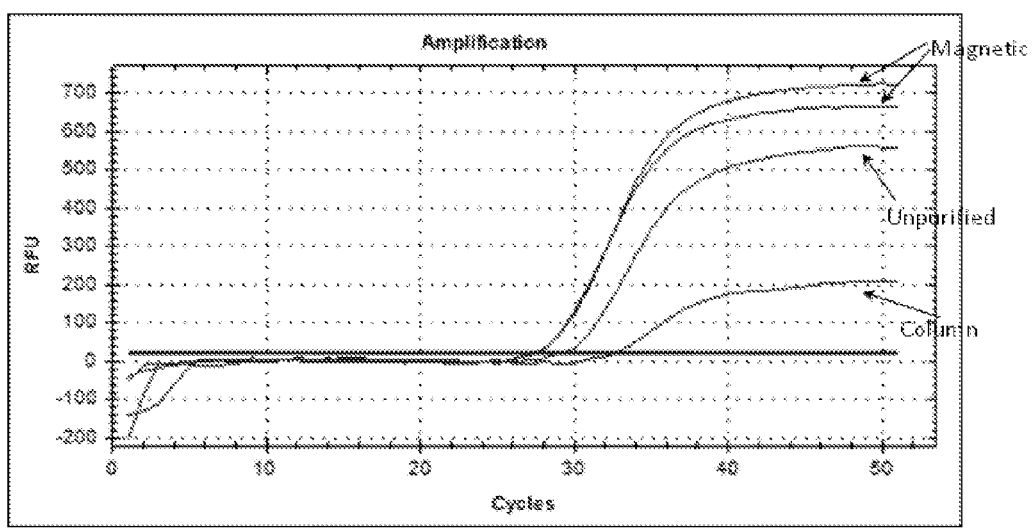
FIG. 14 is a graph depicting results of example nucleic acid amplification reactions described in Example 9.

Results of the experiments are graphically depicted in FIG. 14 and shown below in Table 12. As shown in Table 12, determined Ct values ranged from 27 to 31 and were similar between unpurified sample and sample purified by various means. Results indicate that purification of sample may be not necessary to achieve similar detection sensitivity.

TABLE 12

Experimental Results of Example 9

| Sample Type | Ct |
|---|---|
| Column Purification | 31 |
| Magnetic Beads Purification | 27 |
| Unpurified | 28 |

Example 10: Analysis of Whole Blood and Saliva Samples

Amplification and detection experiments were performed on H3N2 virus-containing blood and saliva samples. Four different samples were tested. Two samples comprising either of the whole blood or saliva samples and two samples comprising a 10-fold dilution (in PBS) of either of the whole blood or saliva samples. Each of the four samples was combined with reagents necessary to conduct reverse transcription of the viral RNA and reagents necessary to complete amplification of the complementary DNA obtained from reverse transcription. The reagents necessary to conduct reverse transcription and DNA amplification were supplied as a commercially available pre-mixture (e.g., Takara One-Step RT-PCR or One-Step RT-qPCR kit) comprising reverse transcriptases (e.g., Sensiscript and Omniscript transcriptases), a DNA Polymerase (e.g., HotStarTaq DNA Polymerase), and dNTPs. Moreover, the reaction tubes also included a TaqMan probe comprising a FAM dye for detection of amplified DNA product. To generate amplified DNA product, each reaction mixture was incubated according to a protocol of denaturing and elongation conditions comprising 20 minutes at 45° C., followed by 2 minutes at 94° C., followed by 42 cycles of 5 seconds at 94° C. and 35 seconds at 55° C. in a real-time PCR thermocycler. Detection of amplified product occurred during incubations.

Figure 15A:
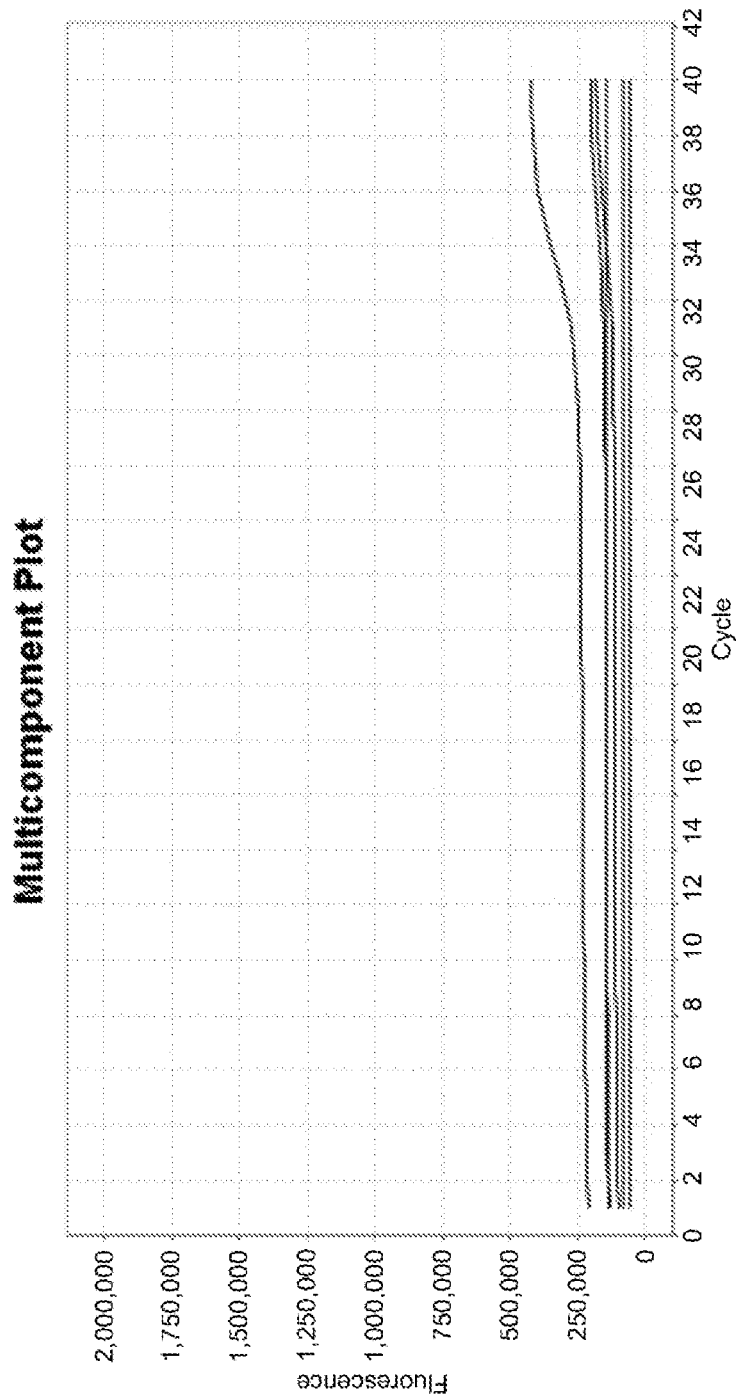
FIGS. 15A and 15B are graphs depicting results of example nucleic acid amplification reactions described in Example 10.
Figure 15B:
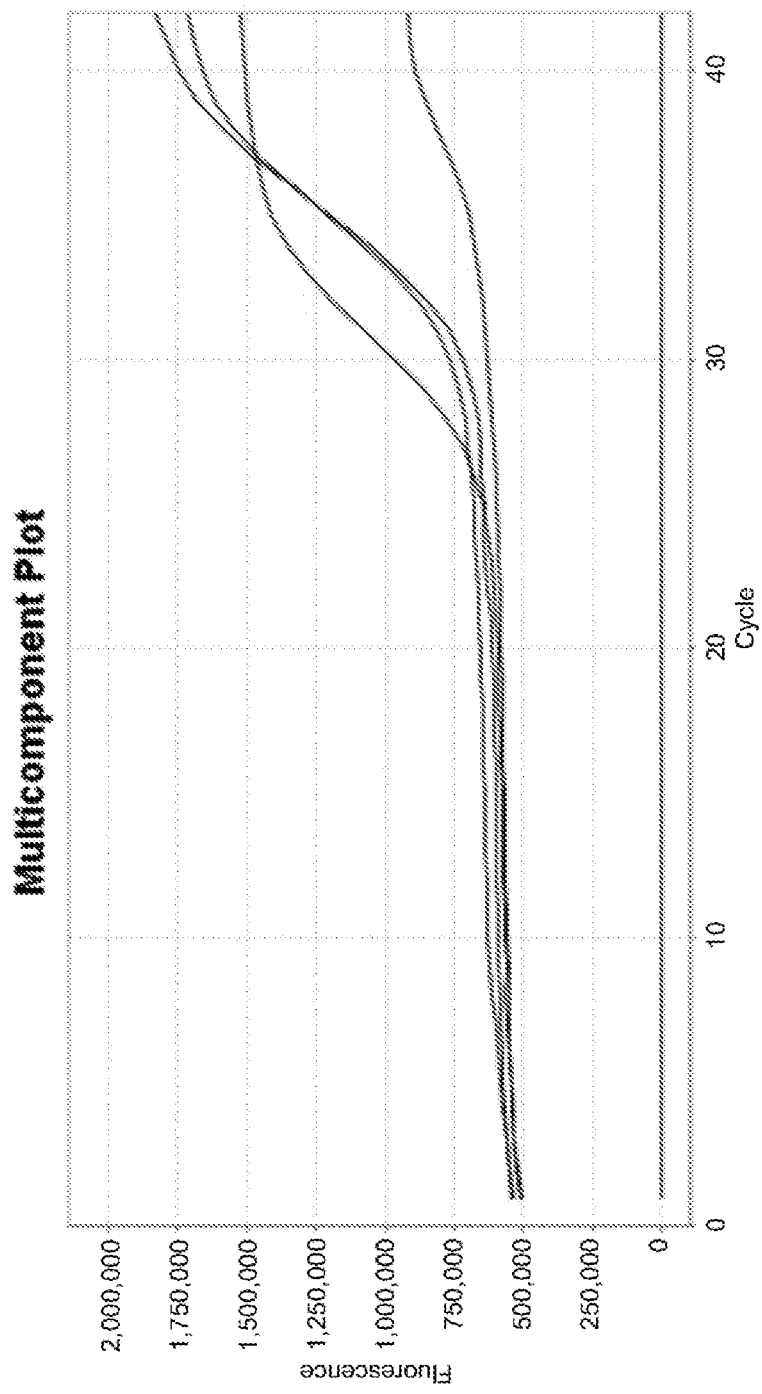
Figure 16A:
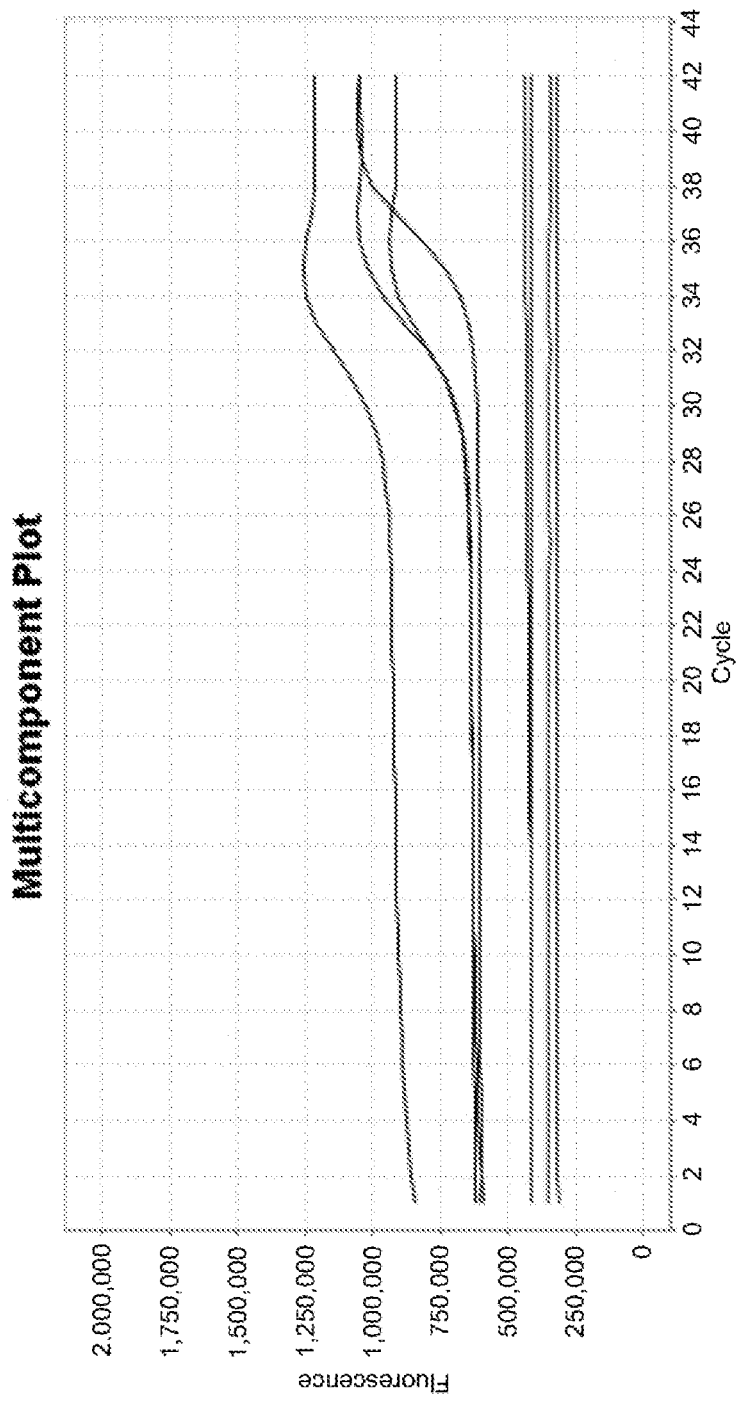
FIGS. 16A and 16B are graphs depicting results of example nucleic acid amplification reactions described in Example 10.
Figure 16B:
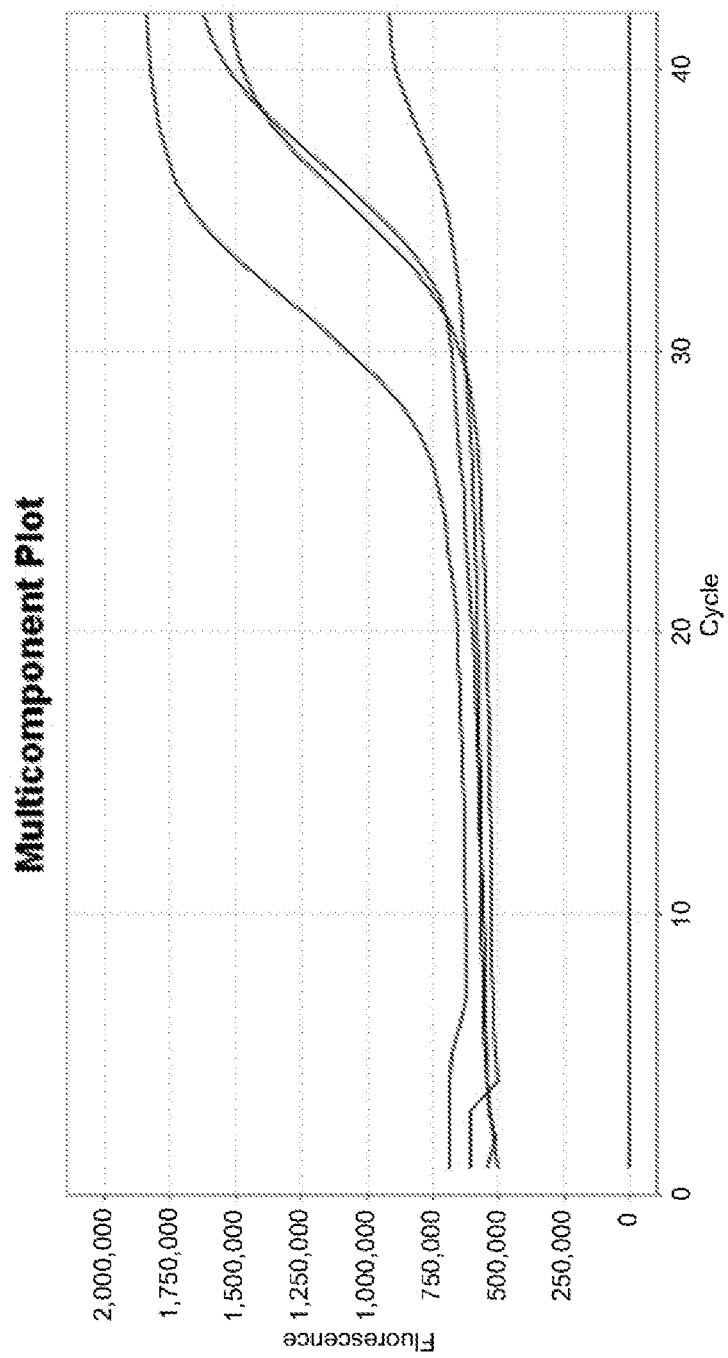

Amplification results for H3N2 are graphically depicted in FIG. 15 (FIG. 15A corresponds to non-diluted blood, FIG. 15B corresponds to diluted blood) and FIG. 16 (FIG. 16A corresponds to non-diluted saliva, FIG. 16B corresponds to diluted saliva). Recorded fluorescence of the FAM dye is plotted against the number of cycles.

As shown in FIG. 15 and FIG. 16, both non-diluted and diluted blood and saliva reaction mixtures showed detectable signal, with Ct values ranging from 24-33. Thus, the data shown in FIGS. 15 and 16 indicate that non-dilute biological samples could be analyzed with good sensitivity, with Ct values of no more than about 40. Moreover, data also indicate that, in cases where dilution of sample is necessary for analysis, amplified product may also be detected in a similar fashion. In some cases, if the inhibitors from samples are too much, dilution may be another way to eliminate the inhibition from the sample, for example, whole blood.

Example 11: Nested PCR

Figure 17:
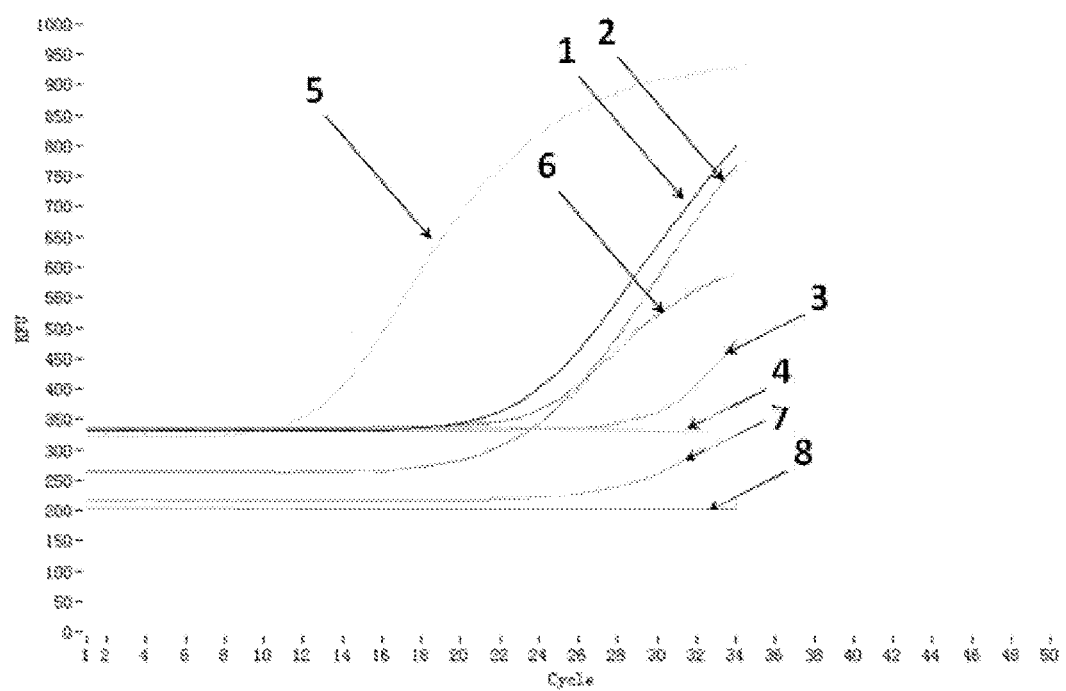
FIG. 17 is a graph depicting results of nucleic acid amplification reactions described in Example 11.
Figure 18:
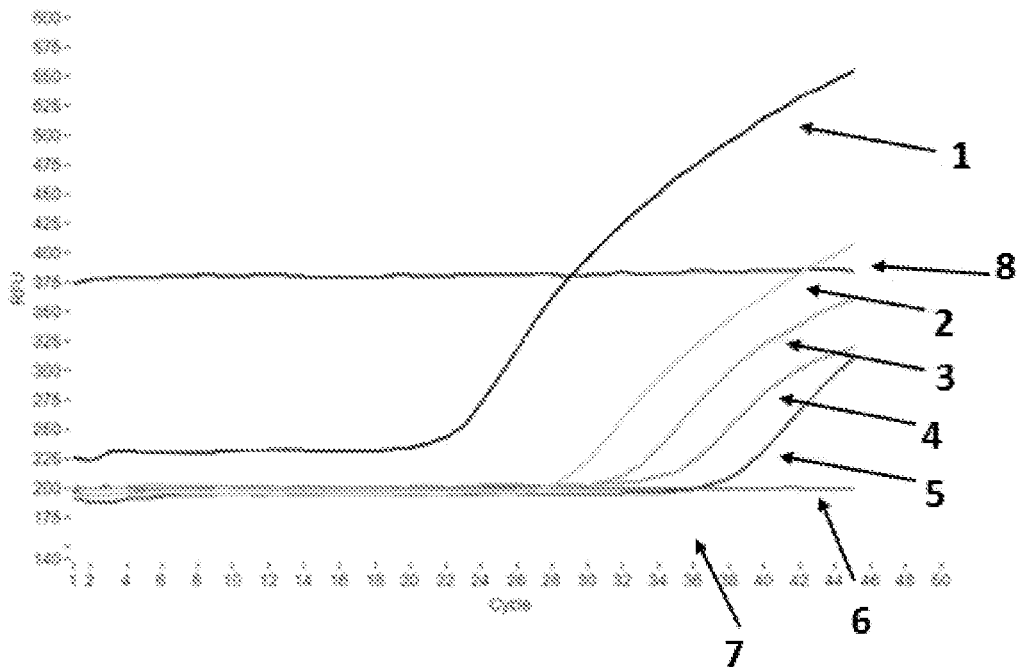
FIG. 18 is a graph depicting results of nucleic acid amplification reactions described in Example 12.

Amplification and detection experiments are performed on H1N1 virus-containing samples. Eight samples are tested. The samples each include H1N1 (2007) virus stock. The samples are each diluted in PBS, at dilutions indicated in Table 13 below. The concentration of virus stock is $1 \times 10^6$ IU/mL. To generate amplified DNA product, a reaction mixture comprising a given sample is incubated according to a protocol of denaturing and elongation conditions. The protocol comprises: (i) in a first run, heating the mixture in a thermocycler at 94° C. for 1 minute followed by 10 or 15 cycles (as indicated in Table 13 below) of 5 seconds at 94° C. and 10 seconds at 57° C.; and (ii) in a second run, heating the mixture in the thermocycler at 94° C. for 1 minute followed by 35 cycles of 5 seconds at 94° C. and 30 seconds at 57° C. A 1 μL series dilution sample is added to a Takara One-step qPCR pre-mixture in a 25 uL reaction volume. After the first run for certain cycles, 1 μL from the reaction is added to the second run reaction mixture. Amplification results for H1N1 are graphically depicted in FIG. 17. The figure shows recorded relative fluorescence units (RFU) as a function of cycle number. Plots for each of the eight samples (1-8) have been indicated in the figure. Samples with detectable signals have Ct values indicated in Table 13.

TABLE 13

Experimental Results of Example 11

| | # | | | | | | | |
|---|---|---|---|---|---|---|---|---|
| | 1 | 2 | 3 | 4 | 5 | 6 | 7 | 8 |
| Sample dilution | 1/10 | 1/100 | 1/1000 | 0 | 1/10 | 1/100 | 1/1000 | 0 |
| Ct | 18 | 21 | 27 | — | 11 | 17 | 24 | — |
| Cycles of the first run | | 10 cycles | | | | 15 Cycles | | |

Example 12: Amplification and Detection of Ebola Recombinant Plasmid

Amplification and detection experiments were performed on human whole blood samples comprising various copy numbers of recombinant plasmid corresponding to the Zaire Ebola Virus (Zaire-EBOV). Eight samples were tested. Six of the samples included the recombinant plasmid at a particular copy number (250000, 25000, 2500, 250, 25 and 2.5 copies) and two of the samples (one having blood only, one having water only) served as control samples. Whole blood samples were analyzed without sample purification.

Each sample was combined with reagents necessary for nucleic acid amplification (e.g., DNA polymerase, dNTPs, primers, co-factors, suitable buffer, primers, etc.) and a reporter agent (e.g., an oligonucleotide probe comprising FAM dye) into a reaction mixture. A summary of the various reaction mixtures by sample number, including copy number of recombinant plasmid, is shown in Table 14. To generate amplified product, each reaction mixture was subjected to two series of denaturing and elongation conditions. The two series were as follows: (i) in a first series, 15 cycles of 1 second at 95° C. and 1 second at 45° C., followed by 1 min at 95° C.; and (ii) in a second series, 45 cycles of 5 seconds at 95° C. and 10 seconds at 55° C. During the second series, signal from the reporter agent was recorded to generate amplification curves and obtain Ct values. Amplification curves for the experiments are graphically depicted in FIG. 18, each labeled by sample number corresponding to sample numbers shown in Table 14. Results depicted in FIG. 18 show recorded relative fluorescence units (RFU) as a function of cycle number. Ct values obtained from the curves shown in FIG. 18 are summarized in Table 15.

As shown in FIG. 18, recombinant plasmid was detected via amplified products for all of the samples that included recombinant plasmid except for sample 6. Moreover, recombinant plasmid was not detected in either of the control samples (samples 7 and 8). Accordingly, results shown in FIG. 18 indicate that, in some cases, a detection sensitivity of 25 copies of plasmid/rxn can be obtained using multiple series of denaturing and elongation conditions and without sample purification.

TABLE 14

Experimental reaction mixtures of Example 12

| Sample | plasmid (copies/rxn) |
|---|---|
| 1 | 250000 |
| 2 | 25000 |
| 3 | 2500 |
| 4 | 250 |
| 5 | 25 |
| 6 | 2.5 |
| 7 | 0 (blood only) |
| 8 | 0 (water only) |

TABLE 15

Determined Ct values from experiments in Example 12

| Sample | Copies/rxn | Ct |
|---|---|---|
| 1 | 250000 | 26.12 |
| 2 | 25000 | 33.61 |
| 3 | 2500 | 37.61 |
| 4 | 250 | 40.61 |

TABLE 15-continued Determined Ct values from experiments in Example 12

| Sample | Copies/rxn | Ct |
|---|---|---|
| 5 | 25 | 42.97 |
| 6 | 2.5 | — |
| 7 | 0 | — |
| 8 | 0 | — |

Example 13: Amplification and Detection of Ebola Virus

Amplification and detection experiments were performed on human whole blood samples comprising various copy numbers of Zaire Ebola Virus (Zaire-EBOV) pseudovirus. Eight samples were tested in duplicate (duplicate set #1 and duplicate set #2) for a total of sixteen samples. Six of the samples included the pseudovirus at a particular copy number (2500000, 250000, 25000, 2500, 250 and 25 copies) and two of the samples (one having blood only, one having water only) served as control samples. Whole blood samples were analyzed without sample purification.

Figure 19A:
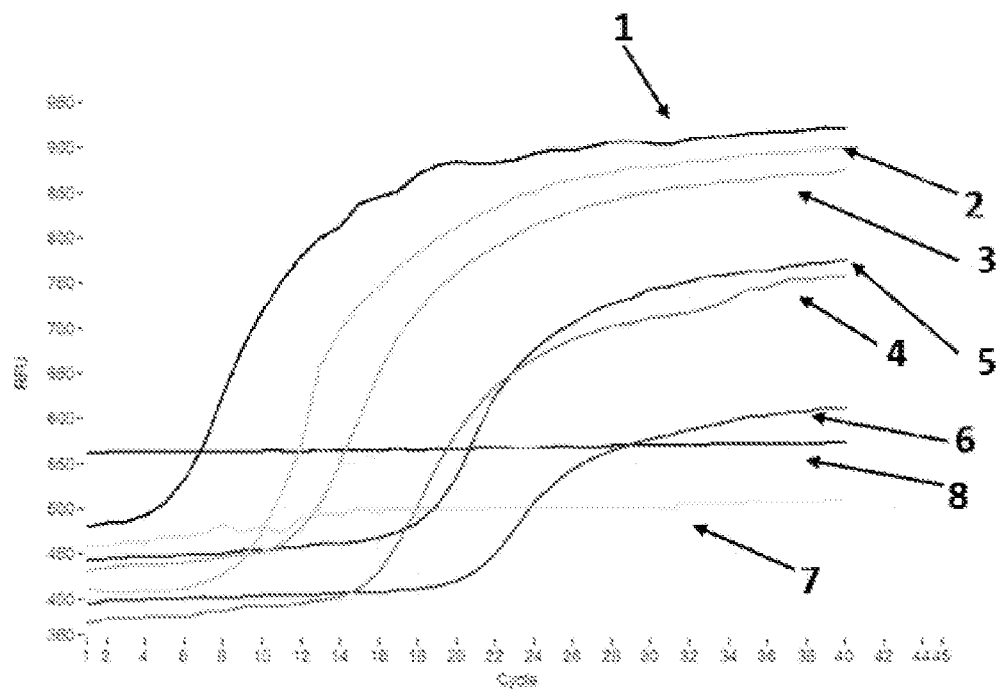
FIG. 19A and FIG. 19B are graphs depicting results of nucleic acid amplification reactions described in Example 13.
Figure 19B:
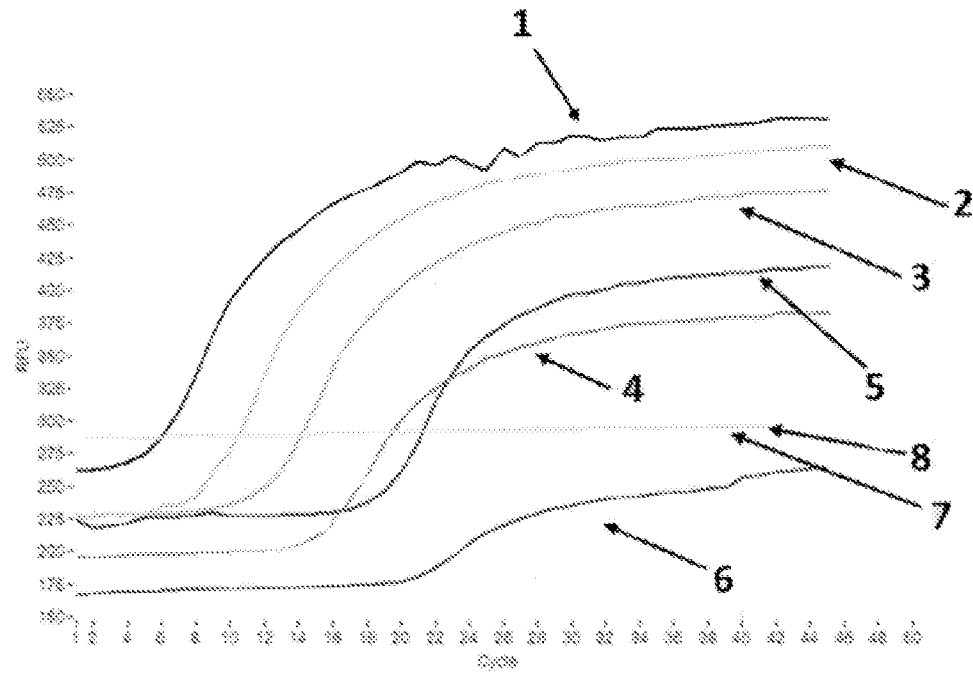

Each sample was combined with reagents necessary for reverse transcription and nucleic acid amplification (e.g., reverse transcriptase, DNA polymerase, dNTPs, co-factors, primers, suitable buffer, etc.) and a reporter agent (e.g., an oligonucleotide probe comprising FAM dye) into a 30 μL reaction mixture. A summary of the reaction mixtures by sample number, including copy number of pseudovirus, is shown in Table 16. To generate amplified product from the pseudovirus, each reaction mixture was subjected to two series of denaturing and elongation conditions. The two series were as follows: (i) in a first series, 15 cycles of 1 second at 95° C. and 1 second at 45° C., followed by 1 min at 95° C.; and (ii) in a second series, 45 cycles of 5 seconds at 95° C. and 10 seconds at 55° C. During the second series, signal from the reporter agent was recorded to generate amplification curves and obtain Ct values. Amplification curves for the experiments are graphically depicted in FIG. 19A (duplicate set #1) and FIG. 19B (duplicate set #2), each labeled by sample number corresponding to those shown in Table 16. Results depicted in FIG. 19A and FIG. 19B show recorded relative fluorescence units (RFU) as a function of cycle number. Ct values obtained from the curves shown in FIG. 19A and FIG. 19B are summarized in Table 17, with "Ct 1" corresponding to duplicate set #1 and "Ct 2" corresponding to duplicate set #2.

As shown in FIG. 19A and FIG. 19B, pseudovirus was detected, in both duplicate sets, via amplified products for all of the samples that included pseudovirus (samples 1-6). Moreover, pseudovirus was not detected in any of the control samples (samples 7 and 8). Accordingly, results shown in FIG. 19A and FIG. 19B indicate that, in some cases, a detection sensitivity of 25 copies of virus/rxn can be obtained using multiple series of denaturing and elongation conditions without sample purification.

TABLE 16

Experimental reaction mixtures of Example 13

| Sample | Pseudovirus (copies/rxn) |
|---|---|
| 1 | 2500000 |
| 2 | 250000 |
| 3 | 25000 |
| 4 | 2500 |
| 5 | 250 |
| 6 | 25 |
| 7 | 0 (blood only) |
| 8 | 0 (water only) |

TABLE 17

Determined Ct values from experiments in Example 13

| Sample | Copies/rxn | Ct 1 | Ct 2 |
|---|---|---|---|
| 1 | 2500000 | 8.57 | 8.44 |
| 2 | 250000 | 12.09 | 11.27 |
| 3 | 25000 | 15.03 | 14.99 |
| 4 | 2500 | 18.90 | 18.87 |
| 5 | 250 | 21.71 | 21.71 |
| 6 | 25 | 27.86 | 39.42 |
| 7 | 0 (blood only) | — | — |
| 8 | 0 (water only) | — | — |

Example 14: Amplification and Detection of Ebola Virus

Amplification and detection experiments were performed on human whole blood samples comprising various copy numbers of Zaire Ebola Virus (Zaire-EBOV) pseudovirus. Eight samples were tested. Six of the samples included the pseudovirus at a particular copy number (2500000, 250000, 25000, 2500, 250 and 25) and two of the samples (one having 20000 copies of a pseudovirus positive control, one having water only) served as control samples. Whole blood samples were analyzed without sample purification.

Figure 20:
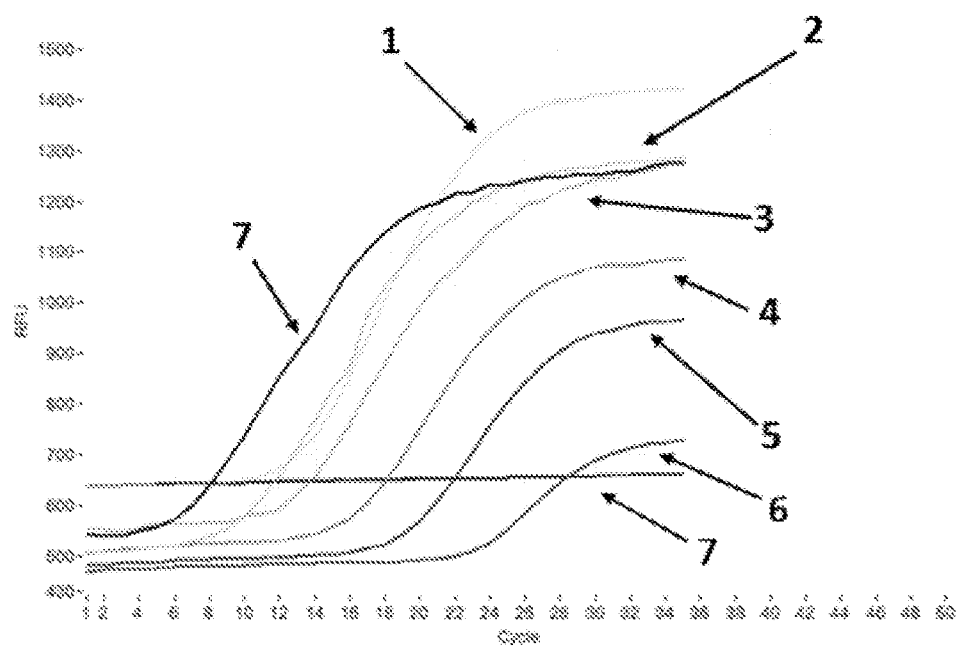
FIG. 20 is a graph depicting results of nucleic acid amplification reactions described in Example 14.
Figure 21:
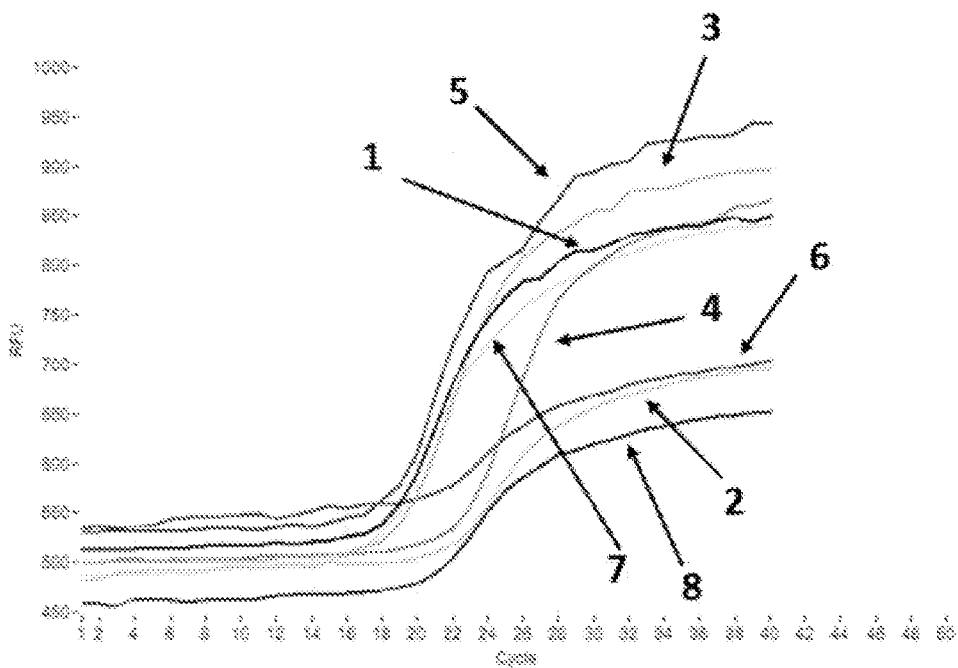
FIG. 21 is a graph depicting results of nucleic acid amplification reactions described in Example 15.

Each sample was combined with reagents necessary for reverse transcription and nucleic acid amplification (e.g., reverse transcriptase, DNA polymerase, primers, dNTPs, co-factors, suitable buffer, etc.) and a reporter agent (e.g., an oligonucleotide probe comprising FAM dye) into a 30 μL reaction mixture. A summary of the various reaction mixtures by sample number, including pseudovirus copy number, is shown in Table 18. To generate amplified product from the pseudovirus, each reaction mixture was subjected to two series of denaturing and elongation conditions. The two series were as follows: (i) in a first series, 15 cycles of 1 second at 95° C. and 1 second at 45° C., followed by 1 min at 95° C.; and (ii) in a second series, 35 cycles of 5 seconds at 95° C. and 10 seconds at 55° C. During the second series, signal from the reporter agent was recorded to generate amplification curves and obtain Ct values. Amplification curves for the experiments are graphically depicted in FIG. 20, each labeled by sample number corresponding to those shown in Table 18. Results depicted in FIG. 20 show recorded relative fluorescence units (RFU) as a function of cycle number. Ct values obtained from the curves shown in FIG. 20 are summarized in Table 19.

As shown in FIG. 20, pseudovirus was detected via amplified products for all of the samples that included pseudovirus (samples 1-6), including the sample including positive control pseudovirus (sample 7). Moreover, pseudovirus was not detected in the water only control sample (sample 8). Accordingly, results shown in FIG. 20 indicate that, in some cases, a detection sensitivity of 25 copies of virus/rxn can be obtained using multiple series of denaturing and elongation conditions without sample purification.

TABLE 18

Experimental reaction mixtures of Example 14

| Sample | Pseudovirus (copies/rxn) |
|---|---|
| 1 | 2500000 |
| 2 | 250000 |
| 3 | 25000 |
| 4 | 2500 |
| 5 | 250 |
| 6 | 25 |
| 7 | 20000 (positive control pseudovirus) |
| 8 | 0 (water only) |

TABLE 19

Determined Ct values from experiments in Example 14

| Sample | Copies/rxn | Ct |
|---|---|---|
| 1 | 2500000 | 10.44 |
| 2 | 250000 | 13.30 |
| 3 | 25000 | 16.14 |
| 4 | 2500 | 19.62 |
| 5 | 250 | 22.92 |
| 6 | 25 | 30.00 |
| 7 | 20000 (positive control) | 15.94 |
| 8 | 0 (water only) | — |

Example 15: Amplification and Detection of Ebola Virus

Amplification and detection experiments were performed on human whole blood samples comprising one of two copy numbers (250 copies/rxn or 25 copies/rxn) of Zaire Ebola Virus (Zaire-EBOV) pseudovirus. Each whole blood sample was tested using one of four reagent systems, for a total of eight samples. Each of the reagent systems (B-1, B-2, B-3 and B-4) included reagents necessary for reverse transcription and nucleic acid amplification (e.g., reverse transcriptase, DNA polymerase, primers, dNTPs, co-factors, suitable buffer, etc.) and a reporter agent (e.g., an oligonucleotide probe comprising FAM dye). Each of the different reagent systems contained different concentrations of the various components in the reagent systems. Each whole blood sample was combined with its appropriate reagent system into a 30 μL reaction mixture. A summary of the various reaction mixtures by sample number, including copy number of pseudovirus and reagent system, is shown below in Table 20. To generate amplified product from the pseudovirus, each reaction mixture was subjected to two series of denaturing and elongation conditions. The two series were as follows: (i) in a first series, 15 cycles of 1 second at 95° C. and 1 second at 45° C., followed by 1 min at 95° C.; and (ii) in a second series, 40 cycles of 5 seconds at 95° C. and 10 seconds at 55° C. During the second series, signal from the reporter agent was recorded to generate amplification curves and obtain Ct values. Amplification curves for the experiments are graphically depicted in FIG. 21, each labeled by sample number corresponding to those shown in Table 20. Results depicted in FIG. 21 show recorded relative fluorescence units (RFU) as a function of cycle number. Ct values obtained from the curves shown in FIG. 21 are summarized in Table 21.

As shown in FIG. 21, pseudovirus was detected via amplified products for all of the samples, including samples having 25 copies/rxn. Accordingly, results shown in FIG. 21 indicate that, in some cases, a detection sensitivity of 25 copies of virus/rxn can be obtained using multiple series of denaturing and elongation conditions, with different reagent systems and without sample purification.

TABLE 20

Experimental reaction mixtures of Example 15

| Sample | Pseudovirus (copies/rxn) | Reagent System |
|---|---|---|
| 1 | 250 | B-1 |
| 2 | 25 | B-1 |
| 3 | 250 | B-2 |
| 4 | 25 | B-2 |
| 5 | 250 | B-3 |
| 6 | 25 | B-3 |
| 7 | 250 | B-4 |
| 8 | 25 | B-4 |

TABLE 21

Determined Ct values from experiments in Example 15

| Sample | Copies/rxn | Ct |
|---|---|---|
| 1 | 250 | 20.38 |
| 2 | 25 | 24.82 |
| 3 | 250 | 20.62 |
| 4 | 25 | 24.05 |
| 5 | 250 | 20.26 |
| 6 | 25 | 25.09 |
| 7 | 250 | 19.86 |
| 8 | 25 | 24.00 |

Example 16: Real-Time PCR Detection for Zaire Ebola Virus

A one-step qPCR method of the present disclosure was used to analyze patient blood serum samples for the Zaire Ebola virus. The samples were not purified. The samples included nine Zaire Ebola virus positive samples and seven Zaire Ebola virus negative samples. A Roche LC96 real-time PCR system was used.

The program employed in this example to analyze the samples is shown in Table 22.

TABLE 22

Thermal cycling program

| Step | Term | Time | Cycle NO. |
|---|---|---|---|
| 1 | 42° C. | 1 min | 1 cycle |
| 2 | 95° C. | 5 second | 10 cycles |
| | 45° C. | 10 second | |
| 3 | 95° C. | 1 min | 1 cycle |
| 4 | 95° C. | 5 second | 40 cycles |
| | 55° C. | 10 second (Reading) | |

The results of the one-step qPCR method are shown in Table 23. The one-step qPCR method testing for the Zaire Ebola virus showed 100% consistency as compared to a verified reagent and method.

TABLE 23

Results

| Sample # | Coyote One-Step QPCR Method (Cq) | Verified reagent and method (Cq) | consistency |
|---|---|---|---|
| 1 | N/A | N/A | Yes |
| 2 | 26.53 | 29.73 | Yes |
| 3 | 17.68 | 19.53 | Yes |
| 4 | N/A | N/A | Yes |
| 5 | N/A | N/A | Yes |
| 6 | N/A | N/A | Yes |
| 7 | N/A | N/A | Yes |
| 8 | 21.52 | 20.98 | Yes |
| 9 | 18.97 | 18.88 | Yes |
| 10 | 24.97 | 24.44 | Yes |
| 11 | 18.92 | 18.91 | Yes |
| 12 | 26.32 | 25.22 | Yes |
| 13 | 20.48 | 20.85 | Yes |
| 14 | 18.5 | 20.45 | Yes |
| 15 | N/A | N/A | Yes |

Example 17: Amplification and Detection of Malaria

Amplification and detection experiments were performed on a human whole blood sample comprising an unknown concentration of Malaria pathogens. Two sets of experiments were completed. In the first set of experiments, duplicate experiments were completed for a 1:4 dilution (in 1×PBS) of the human whole blood sample; an experiment was completed for a sample comprising whole blood and a plasmid corresponding to Malaria pathogens; and an experiment was completed for a water only control. In the second set of experiments, experiments were completed for samples comprising various dilutions (1:4, 1:40, 1:400, 1:4000, 1:40000 and 1:400000) of the human whole blood sample in 1×PBS along with blood only and water only control samples. Whole blood samples were analyzed without sample purification.

Each sample was combined with reagents necessary for nucleic acid amplification (e.g., DNA polymerase, primers, dNTPs, co-factors, suitable buffer, etc.) and a reporter agent (e.g., an oligonucleotide probe comprising FAM dye) into a 30 µL reaction mixture. A summary of the reaction mixtures by sample number, including dilution, for the first set of experiments is shown in Table 24. A summary of the reaction mixtures by sample number, including dilution, for the second set of experiments is shown in Table 25. To generate amplified product from Malaria pathogens, each reaction mixture was subjected to two series of denaturing and elongation conditions. The two series were as follows: (i) in a first series, 13 cycles of 1 second at 95° C. and 1 second at 45° C., followed by 1 min at 95° C.; and (ii) in a second series, 45 cycles of 5 seconds at 95° C. and 10 seconds at 55° C. During the second series, signal from the reporter agent was recorded to generate amplification curves. Amplification curves for the first set of experiments are graphically depicted in FIG. 22A and amplification curves for the second set of experiments are graphically depicted in FIG. 22B. Each curve is labeled by its corresponding sample number in Tables 24 and 25, respectively. Results depicted in FIG. 22A and FIG. 22B show recorded relative fluorescence units (RFU) as a function of cycle number.

Figure 22A:
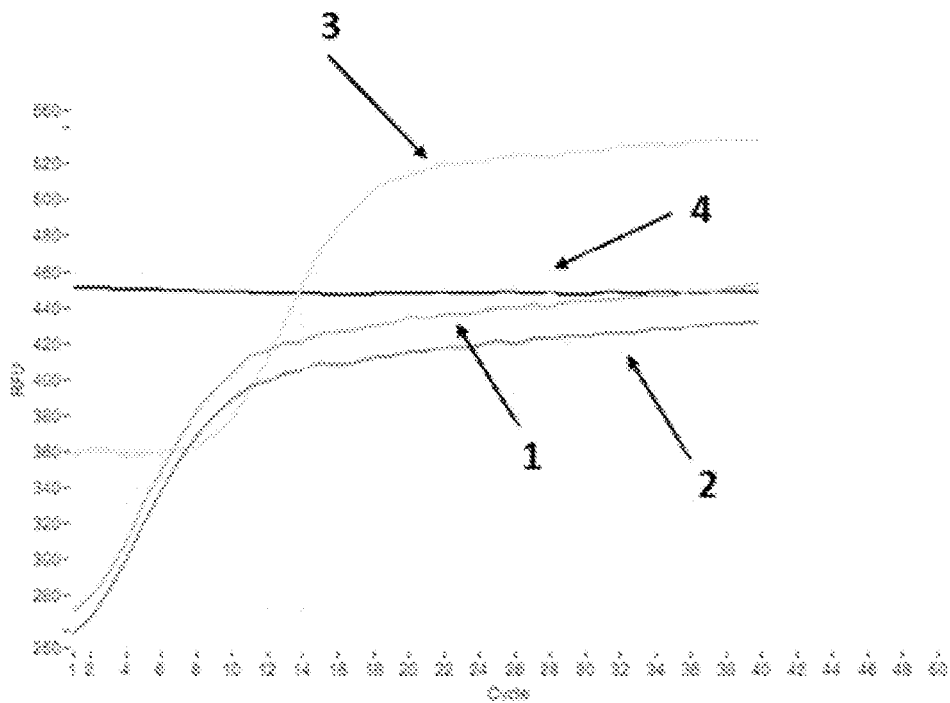
FIG. 22A and FIG. 22B are graphs depicting results of nucleic acid amplification reactions described in Example 17.

As shown in FIG. 22A, Malaria pathogens were detected via amplified products for the two reaction mixtures comprising whole blood sample (samples 1 and 2) and for the positive control comprising recombinant plasmid (sample 3). Moreover, Malaria pathogens were not detected in the water only control sample (sample 4). Accordingly, results shown in FIG. 22A indicate that Malaria pathogens can, in some cases, be detected using multiple series of elongation and denaturation conditions without sample purification.

Figure 22B:
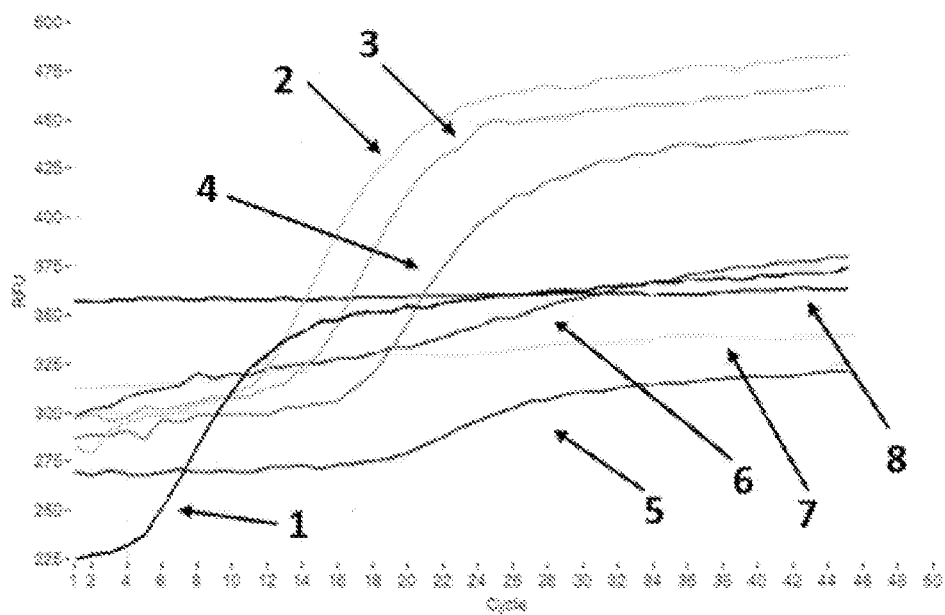

As shown in FIG. 22B, Malaria pathogens were detected via amplified products for all reaction mixtures containing whole blood sample (samples 1-6). Moreover, Malaria pathogens were not detected in the water only and blood only control samples (sample 7 and 8). Accordingly, results shown in FIG. 22B indicate that a pathogen(s), including Malaria pathogens, can, in some cases, be detected at dilutions of up to 1:400000 using multiple series of denaturing and elongation conditions and without sample purification.

TABLE 24

Experimental reaction mixtures for first set of experiments in Example 17

| Sample | Dilution |
|---|---|
| 1 | 1:4 |
| 2 | 1:4 |
| 3 | 1:2 (plasmid in whole blood control) |
| 4 | None (water only) |

TABLE 25

Experimental reaction mixtures for second set of experiments in Example 17

| Sample | Dilution |
|---|---|
| 1 | 1:4 |
| 2 | 1:40 |
| 3 | 1:400 |
| 4 | 1:4000 |
| 5 | 1:40000 |
| 6 | 1:400000 |
| 7 | 0 (blood only) |
| 8 | 0 (water only) |

Example 18: Amplification and Detection of Dengue Virus

Amplification and detection experiments were performed on samples obtained from a culture comprising an unknown concentration of Dengue virus. Three sets of experiments were completed. In the first set of experiments, duplicate experiments were completed for undiluted culture; an experiment was completed for 1:10 dilution of the culture; and an experiment was completed for a water only control. In the second set of experiments, experiments were completed for various dilutions (no dilution, 1:10, 1:100, 1:1000, 1:10000, 1:100000 and 1:1000000) of the culture along with a water only control sample. In the third set of experiments, experiments were completed for various dilutions (no dilution, 1:10, 1:100, 1:1000 and 1:10000) of the culture along with a water only control sample. Culture samples were analyzed without sample purification.

Figure 23A:
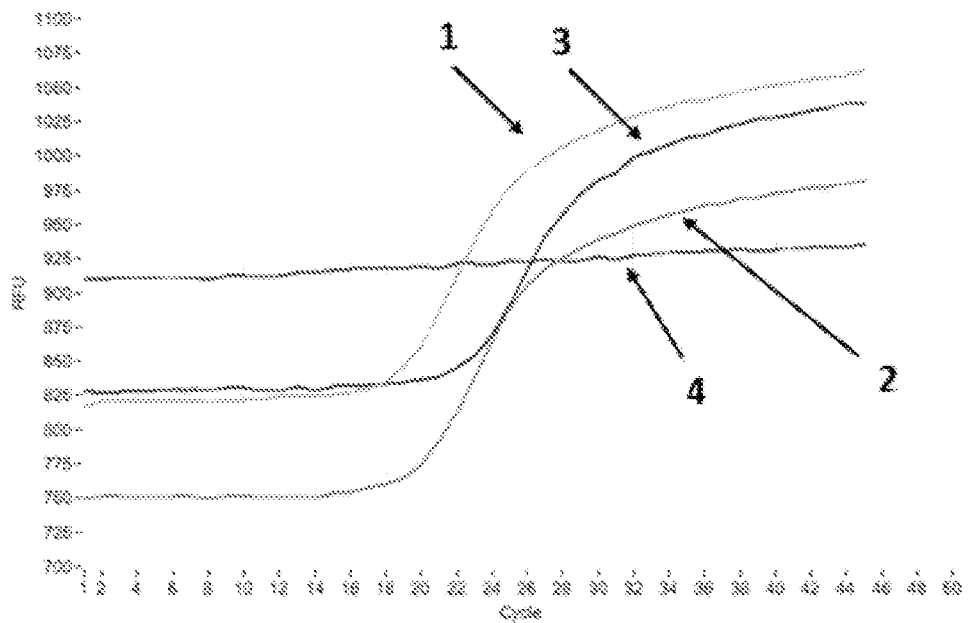
FIG. 23A, FIG. 23B and FIG. 23C are graphs depicting results of nucleic acid amplification reactions described in Example 18.
Figure 23B:
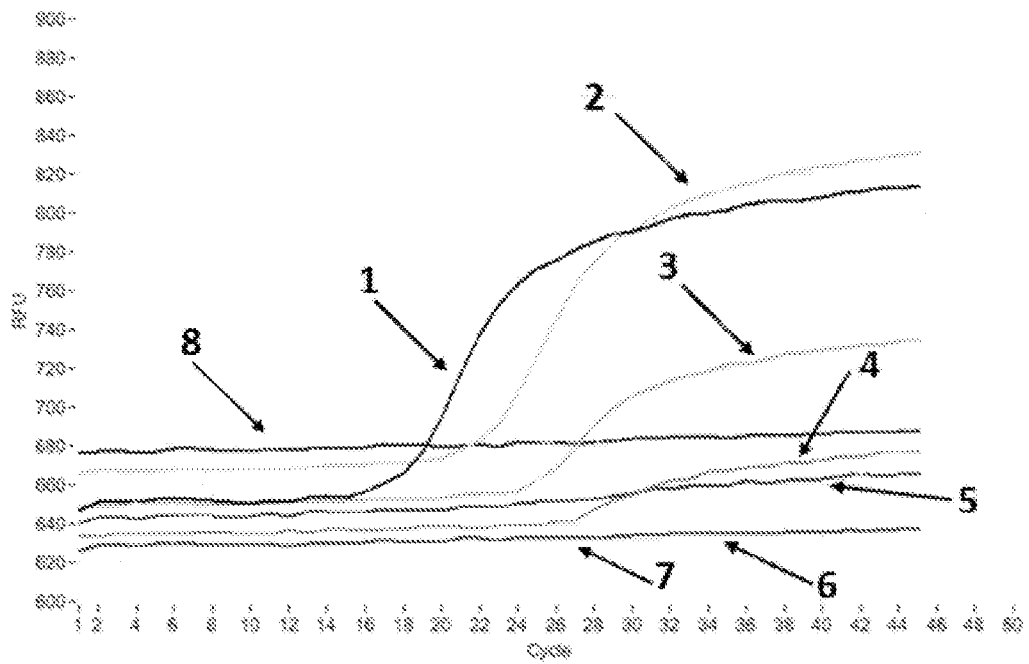
Figure 23C:
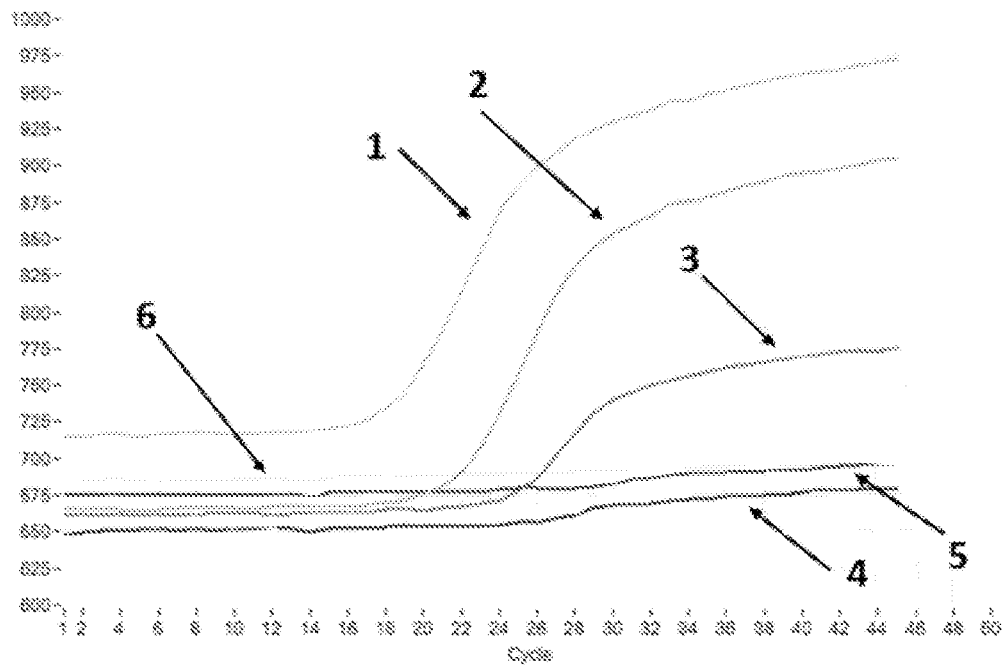

2 µL of each sample was combined with reagents necessary for reverse transcription and nucleic acid amplification (e.g., reverse transcriptase, DNA polymerase, primers, dNTPs, co-factors, suitable buffer, etc.) and a reporter agent (e.g., an oligonucleotide probe comprising FAM dye) into a 30 µL reaction mixture. A summary of the reaction mixtures, including dilution, for the first set of experiments is shown in Table 26, for the second set of experiments in Table 27 and for the third set of experiments in Table 28. To generate amplified product from the virus, each reaction mixture was subjected to two series of denaturing and elongation conditions. The two series were as follows: (i) in a first series, 1 min at 42° C., 10 cycles of 5 seconds at 95° C. and 10 seconds at 45° C., followed by 1 min at 95° C.; and (ii) in a second series, 45 cycles of 5 seconds at 95° C. and 10 seconds at 55° C. During the second series, signal from the reporter agent was recorded to generate amplification curves. Amplification curves for the first set of experiments are graphically depicted in FIG. 23A, amplification curves for the second set of experiments are graphically depicted in FIG. 23B and amplification curves for the third set of experiments are graphically depicted in FIG. 23C. Each curve is labeled by its corresponding sample number in Tables 26, 27 and 28 respectively. Results depicted in FIG. 23A, FIG. 23B and FIG. 23C show recorded relative fluorescence units (RFU) as a function of cycle number. Ct values obtained from the curves shown in FIG. 23A, FIG. 23B and FIG. 23C are shown in Tables 26, 27 and 28 respectively.

As shown in FIG. 23A, virus was detected via amplified products for the three reaction mixtures comprising virus (samples 1-3). Moreover, virus was not detected in the water only control sample (sample 4). Accordingly, results shown in FIG. 23A indicate that Dengue virus can, in some cases, be detected using multiple series of elongation and denaturation conditions.

As shown in FIG. 23B, virus was detected via amplified products for reaction mixtures containing Dengue virus and either not diluted (sample 1) or diluted up to 1:1000 (samples 2, 3 and 4). A Ct value, however, was not determined for the 1:1000 reaction mixture (sample 4). Virus was not detected in higher dilutions (samples 5, 6 and 7) or in the water only control sample (sample 8). Accordingly, results shown in FIG. 23B indicate that virus can, in some cases, be detected at dilutions of up to 1:1000, where Ct values can be generated at dilutions up to 1:100 using multiple series of denaturing and elongation conditions and without sample purification.

As shown in FIG. 23C, virus was detected via amplified products for reaction mixtures containing Dengue virus and either not diluted (sample 1) or diluted up to 1:1000 (samples 2, 3 and 4). A Ct value, however, was not determined for the 1:1000 reaction mixture. Virus was not detected in higher dilutions (sample 5) or in the water only control sample (sample 6). Accordingly, results shown in FIG. 23C indicate that virus can, in some cases, be detected at dilutions of up to 1:1000, where Ct values can be generated at dilutions up to 1:100 using multiple series of denaturing and elongation conditions and without sample purification.

TABLE 26

Experimental reaction mixtures and determined Ct values for first set of experiments in Example 18

| Sample | Dilution | Ct value |
| --- | --- | --- |
| 1 | none | 19.32 |
| 2 | none | 20.40 |
| 3 | 1:10 | 23.23 |
| 4 | no virus (water only) | — |

TABLE 27

Experimental reaction mixtures and determined Ct values for second set of experiments in Example 18

| Sample | Dilution | Ct value |
| --- | --- | --- |
| 1 | none | 20.85 |
| 2 | 1:10 | 25.14 |
| 3 | 1:100 | 31.57 |
| 4 | 1:1000 | — |
| 5 | 1:10000 | — |
| 6 | 1:100000 | — |
| 7 | 1:1000000 | — |
| 8 | no virus (water only) | — |

TABLE 28

Experimental reaction mixtures and determined Ct values for third set of experiments in Example 18

| Sample | Dilution | Ct value |
| --- | --- | --- |
| 1 | None | 19.22 |
| 2 | 1:10 | 22.43 |
| 2 | 1:100 | 26.55 |
| 4 | 1:1000 | — |
| 5 | 1:10000 | — |
| 6 | no virus (water only) | — |

Example 19: Detection of Single Nucleotide Polymorphisms (SNPs)

Amplification and detection experiments were performed on human oropharyngeal swab or blood samples comprising a particular genotype of cytochrome P450 2C19, CYP2C19*2 (having a "GA" genotype) or CYP2C19*3 (having a "GG" genotype). Two sets of experiments were conducted—one set for samples obtained from human oropharyngeal swabs and one set for samples obtained from blood. In the first set of experiments, seven different samples obtained from human oropharyngeal swabs were analyzed without sample purification. In the second set of experiments, five different blood samples were analyzed without sample purification.

Each sample was combined with reagents necessary for nucleic acid amplification (e.g., DNA polymerase, primers, dNTPs, co-factors, suitable buffer, etc.) and two reporter agents (e.g., an oligonucleotide probe comprising FAM dye to detect amplification of nucleic acids, an oligonucleotide probe comprising Texas Red dye to detect the "GA" genotype) into a reaction mixture. To generate amplified product, each reaction mixture was subjected to a thermocycling protocol that included 5 min at 95° C. followed by 50 cycles of 5 seconds at 95° C. and 10 seconds at 49° C. During thermocycling, signals from the reporter agents were recorded to generate amplification curves. Amplification curves for the first set of experiments (human oropharyngeal swabs) are graphically depicted in FIG. 24A (signal corresponding to the FAM oligonucleotide probe) and FIG. 24B (signal corresponding to the Texas Red oligonucleotide probe). Amplification curves for the second set of experiments (blood samples) are graphically depicted in FIG. 25A (signal corresponding to the FAM oligonucleotide probe) and FIG. 25B (signal corresponding to the Texas Red oligonucleotide probe). Results depicted in FIG. 24A, FIG. 24B, FIG. 25A and FIG. 25B show recorded relative fluorescence units (RFU) as a function of cycle number. Each curve is labeled by its corresponding reaction mixture number in Table 29 (oropharyngeal swab experiments) or Table 30 (blood experiments). Ct values determined for amplification curves are also shown in Table 29 or Table 30 along with determined genotype. In amplification curves where signal from Texas Red was observed in FIG. 24B or FIG. 25B, it was determined that the corresponding reaction mixture had the "GA" genotype. Moreover, in amplification curves where signal from Texas Red was not observed in FIG. 24B or FIG. 25B, it was determined that the corresponding reaction mixture had the "GG" genotype.

Figure 24A:
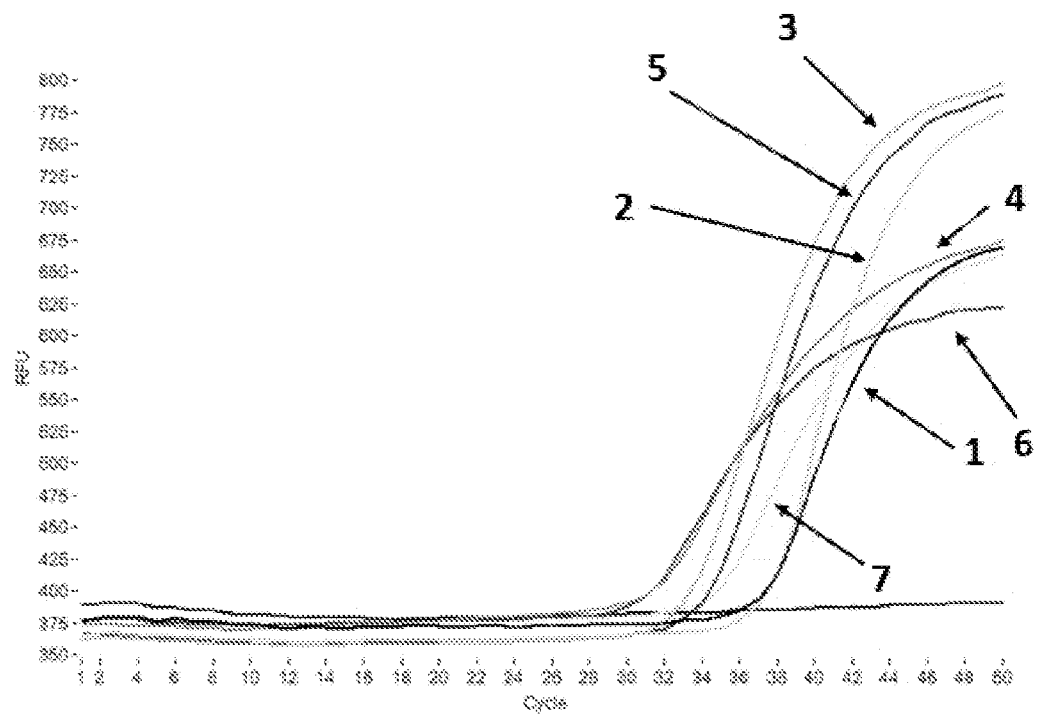
FIG. 24A and FIG. 24B are graphs depicting results of nucleic acid amplification reactions described in Example 19.
Figure 24B:
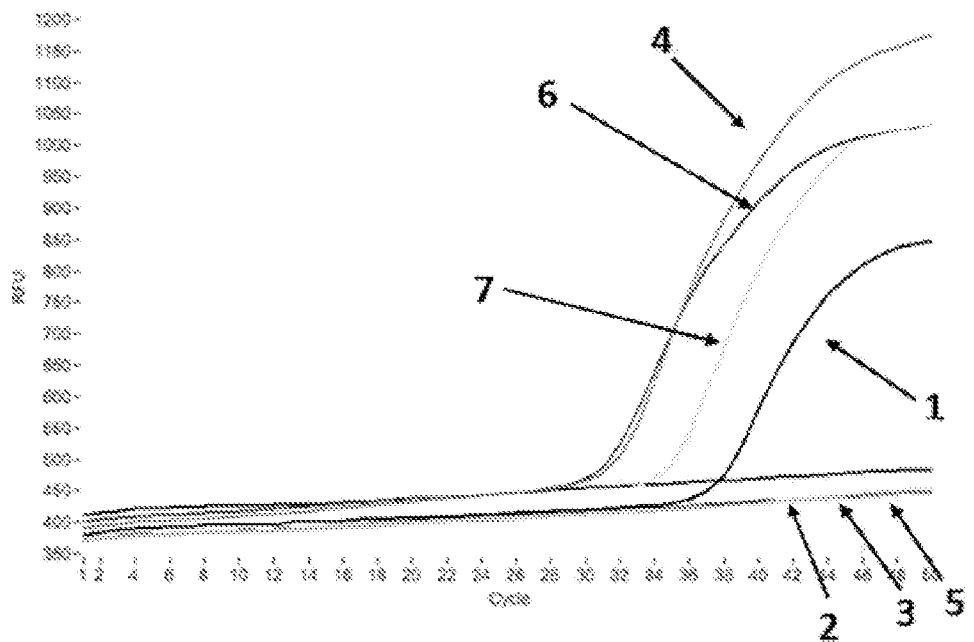

As shown in FIG. 24A, amplified product was observed for each of the reaction mixtures having sample obtained from oropharyngeal swabs, suggesting that amplification of nucleic acids occurs. However, as shown in FIG. 24B, amplified product was observed for only some of the reaction mixtures (reaction mixtures 1, 4, 6 and 7) having sample obtained from oropharyngeal swabs, these reaction mixtures corresponding to the "GA" genotype. In the other reaction mixtures (reaction mixtures 2, 3 and 5), amplified products were not observed, these reaction mixtures corresponding to the "GG" genotype. Results shown in FIG. 24A and FIG. 24B were validated via amplification and detection experiments using DNA extracted from oral swab samples (data not shown). Thus, results shown in FIG. 24A and FIG. 24B suggest that, in some cases, SNPs can be detected via real-time amplification in samples obtained from oropharyngeal swabs without sample purification.

Figure 25A:
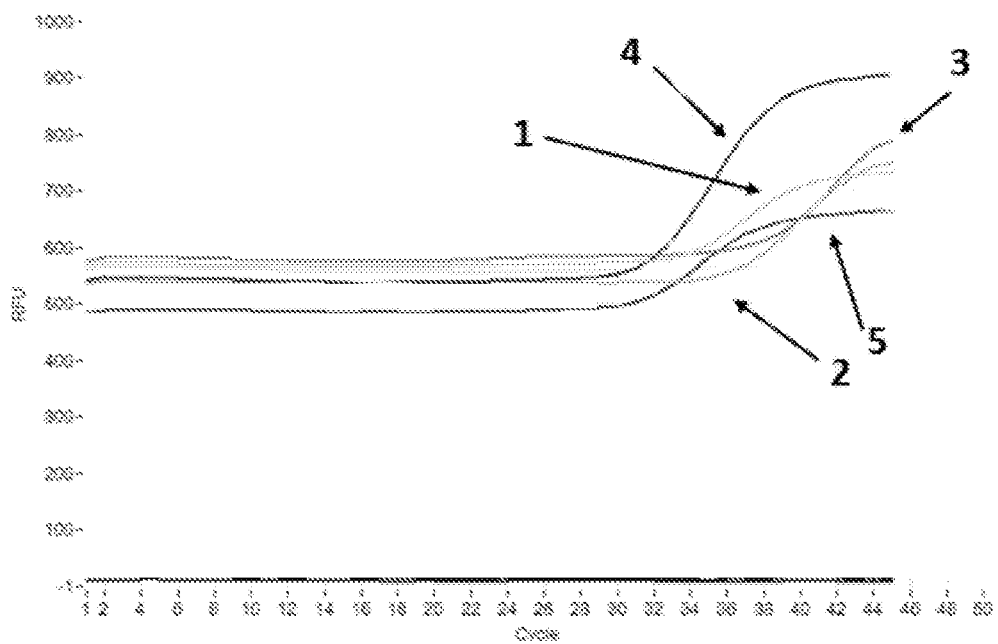
FIG. 25A and FIG. 25B are graphs depicting results of nucleic acid amplification reactions described in Example 19.
Figure 25B:
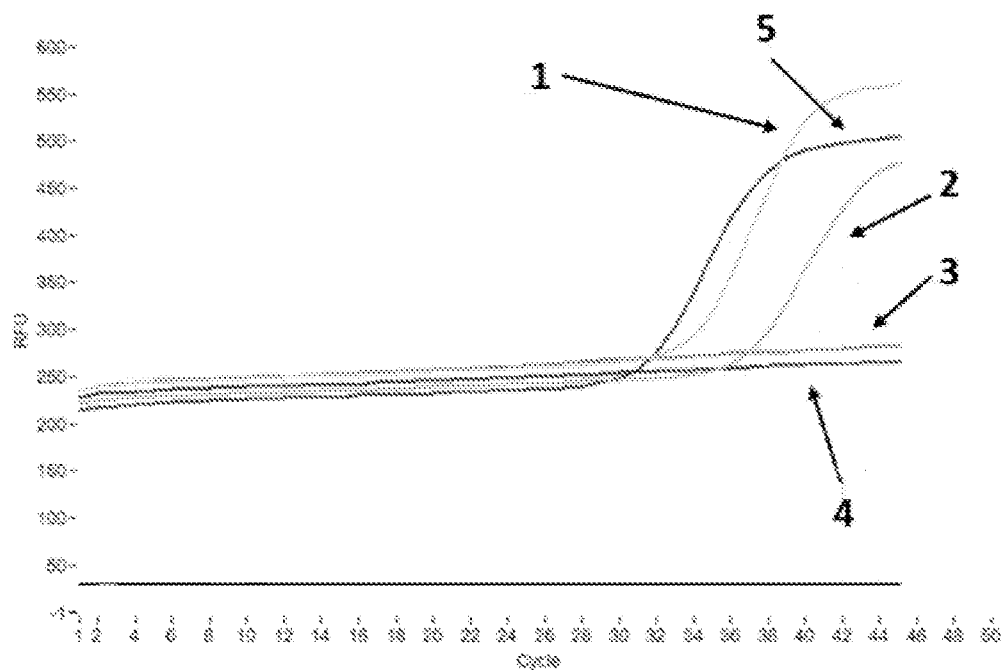

As shown in FIG. 25A, amplified product was observed for each of the reaction mixtures having sample obtained from blood, suggesting that amplification of nucleic acids occurs. However, as shown in FIG. 25B, amplified product was observed for only some of the reaction mixtures (reaction mixtures 1, 2 and 5) having sample obtained from blood, these reaction mixtures corresponding to the "GA" genotype. In the other reaction mixtures (reaction mixtures 3 and 4), amplified products were not observed, these reaction mixtures corresponding to the "GG" genotype. Results shown in FIG. 25A and FIG. 25B were validated using nucleic acid sequencing. Thus, results shown in FIG. 25A and FIG. 25B suggest that, in some cases, SNPs can be detected via real-time amplification in samples obtained from blood without sample purification.

TABLE 29

Determined Ct values and genotypes for oropharyngeal swab experiments in Example 19

| Reaction Mixture | Ct- FAM Reporter | Ct-Texas Red Reporter | Genotype |
|---|---|---|---|
| 1 | 38.70 | 40.25 | GA |
| 2 | 38.28 | — | GG |
| 3 | 34.16 | — | GG |
| 4 | 33.18 | 33.75 | GA |
| 5 | 35.20 | — | GG |
| 6 | 33.08 | 33.59 | GA |
| 7 | 36.45 | 37.01 | GA |

TABLE 30

Determined Ct values and genotypes for blood experiments in Example 19

| Reaction Mixture | Ct- FAM Reporter | Ct-Texas Red Reporter | Genotype |
|---|---|---|---|
| 1 | 38.36 | 36.24 | GA |
| 2 | 39.97 | 39.67 | GA |
| 3 | 41.25 | — | GG |
| 4 | 33.96 | — | GG |
| 5 | 35.68 | 34.12 | GA |

Example 20: Amplification and Detection of Adenovirus Type 55 (ADV55) and Adenovirus Type 7 (ADV7)

Amplification and detection experiments were performed on samples obtained from oropharyngeal swabs comprising various copy numbers of adenovirus type 55 (ADV55) or unknown concentrations of adenovirus type 7 (ADV7). Two sets of experiments were completed—one set for samples having ADV55 and one set for experiments having ADV7. In the first set of experiments, six different experiments having samples comprising differing copy numbers (1, 10, 100, 1000, 10000, and 100000 copies) of ADV55 were completed without sample purification along with an experiments for a negative control. In the second set of experiments, eight different experiments having samples comprising unknown copy number of ADV7 were completed without sample purification.

Each sample was combined with reagents necessary for nucleic acid amplification (e.g., DNA polymerase, primers, dNTPs, co-factors, suitable buffer, etc.) and a reporter agent (e.g., an oligonucleotide probe comprising FAM dye) into a reaction mixture. A summary of the reaction mixtures, including ADV55 copy number, for the first set of experiments is shown in Table 31. To generate amplified product from viruses, each reaction mixture was subjected to two series of denaturing and elongation conditions. The two series were as follows: (i) in a first series, 20 cycles of 1 second at 95° C. and 1 second at 45° C., followed by 1 min at 95° C.; and (ii) in a second series, 35 cycles of 5 seconds at 95° C. and 34 seconds at 60° C. During the second series, signal from the reporter agent was recorded to generate amplification curves and obtain Ct values. Amplification curves for the first set of experiments are graphically depicted in FIG. 26A, each labeled by reaction mixture number corresponding to those shown in Table 31. Amplification curves for the second set of experiments are graphically depicted in FIG. 26B and corresponding Ct values shown in Table 32. Amplification curves in FIG. 26B are labelled as they correspond to reaction mixture number shown in Table 32. Results depicted in FIG. 26A and FIG. 26B show recorded relative fluorescence units (RFU) as a function of cycle number.

Figure 26A:
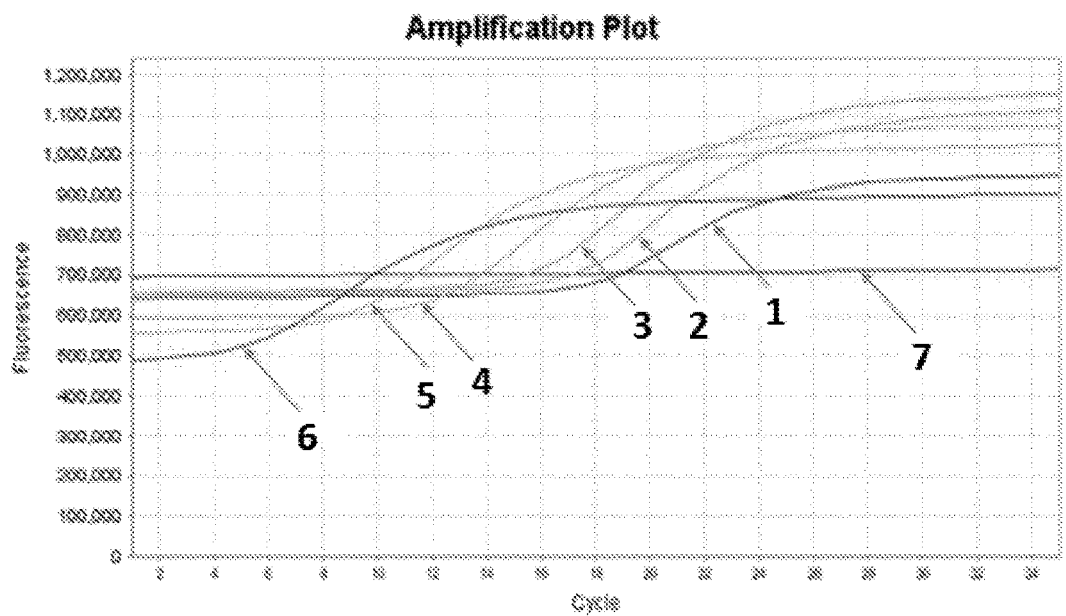
FIG. 26A and FIG. 26B are graphs depicting results of nucleic acid amplification reactions described in Example 20.
Figure 26B:
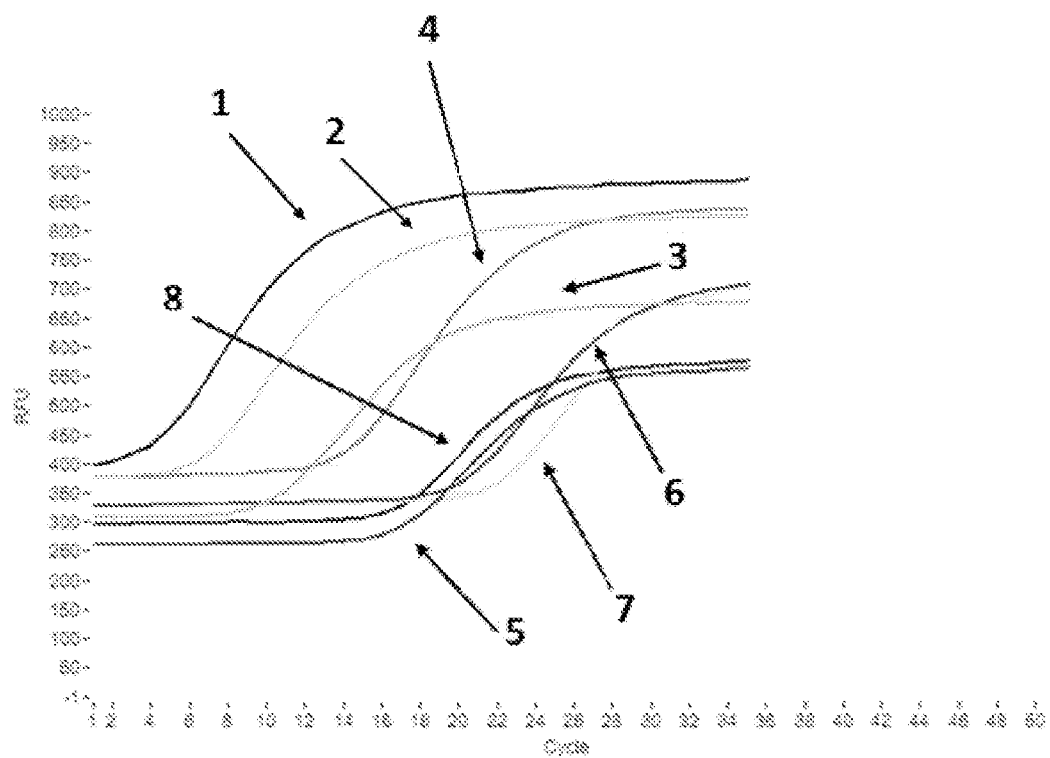

As shown in FIG. 26A, ADV55 was detected via amplified products for all of the reaction mixtures comprising sample containing virus (reaction mixtures 1-6). Moreover, virus was not detected in the negative control reaction mixture (reaction mixture 7). Accordingly, results shown in FIG. 26A indicate that ADV55 virus can, in some cases, be detected using multiple series of elongation and denaturation conditions without sample purification and at various levels of dilution.

As shown in FIG. 26B, ADV7 was detected via amplified products for all of the reaction mixtures. Accordingly, results shown in FIG. 26B indicate that ADV7 virus can, in some cases, be detected using multiple series of elongation and denaturation conditions and without sample purification.

TABLE 31

Experimental reaction mixtures for ADV55 experiments in Example 20

| Reaction Mixture | ADV55 Copy Number/Rxn |
|---|---|
| 1 | 1 |
| 2 | 10 |
| 3 | 100 |
| 4 | 1000 |
| 5 | 10000 |
| 6 | 100000 |
| 7 | 0 (negative control) |

TABLE 32

Determined Ct values for ADV7 experiments in Example 20

| Reaction Mixture | Ct Value |
|---|---|
| 1 | 5.12 |
| 2 | 7.16 |
| 3 | 10.97 |
| 4 | 14.15 |
| 5 | 17.58 |
| 6 | 20.29 |
| 7 | 22.13 |
| 8 | 17.66 |

Example 21: Amplification and Detection of Armored RNA Hepatitis C Virus (RNA-HCV)

Amplification and detection experiments were performed on blood plasma samples comprising various copy numbers of armored RNA Hepatitis C Virus (RNA-HCV). Three different experiments having samples comprising differing copy numbers (10, 100 and 500 copies) of RNA-HCV were completed without sample purification along with an experiment completed for a negative control.

Each sample was combined with reagents necessary for reverse transcription and nucleic acid amplification (e.g., reverse transcriptase, DNA polymerase, primers, dNTPs, co-factors, suitable buffer, etc.) and a reporter agent (e.g., an oligonucleotide probe comprising FAM dye) into a reaction mixture. A summary of the reaction mixtures, including RNA-HCV copy number is shown in Table 33. To generate amplified DNA product from viruses, each reaction mixture was subjected to two series of denaturing and elongation conditions. The two series were as follows: (i) in a first series, 20 cycles of 1 second at 95° C. and 1 second at 45° C., followed by 1 min at 95° C.; and (ii) in a second series, 55 cycles of 5 seconds at 95° C. and 34 seconds at 60° C. During the second series, signal from the reporter agent was recorded to generate amplification curves. Amplification curves for the first set of experiments are graphically depicted in FIG. 27, each labeled by number corresponding to reaction mixture numbers shown in Table 33. Results depicted in FIG. 27 show recorded relative fluorescence units (RFU) as a function of cycle number.

Figure 27:
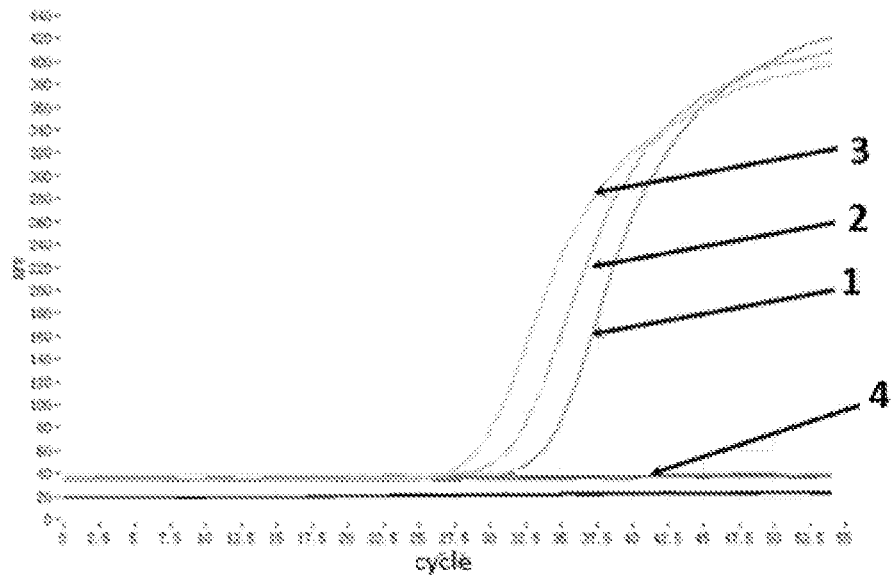
FIG. 27 is a graph depicting results of nucleic acid amplification reactions described in Example 21.

As shown in FIG. 27, RNA-HCV was detected via amplified products for all of the reaction mixtures comprising sample containing virus (reaction mixture 1-3). Moreover, RNA-HCV was not detected in the negative control reaction mixture (reaction mixture 4). Accordingly, results shown in FIG. 27 indicate that RNA-HCV can, in some cases, be detected using multiple series of elongation and denaturation conditions without sample purification. A detection sensitivity of 10 copies/rxn can also be achieved.

TABLE 33

Experimental reaction mixtures for RNA-HCV experiments in Example 21

| Reaction Mixture | RNA-HCV Copy Number/Rxn |
|---|---|
| 1 | 10 |
| 2 | 100 |
| 3 | 500 |
| 4 | 0 (negative control) |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of amplifying a target nucleic acid present in a biological sample obtained from a subject, comprising:
   (a) activating an amplification system comprising (i) an electronic display screen comprising a user interface that displays a graphical element accessible by a user to select an amplification protocol to amplify said target nucleic acid in said biological sample, and (ii) an amplification unit that, in response to selection of said graphical element by said user, implements said amplification protocol;
   (b) receiving said selection of said graphical element by said user on said user interface;
   (c) in response to receiving said selection of said graphical element in (b), using said amplification unit to implement said amplification protocol, which amplification protocol comprises:
      (1) providing a reaction vessel comprising a reaction mixture including said biological sample and reagents for conducting nucleic acid amplification, said reagents comprising (i) a deoxyribonucleic acid (DNA) polymerase and optionally a reverse transcriptase, and (ii) a primer set for said target nucleic acid, wherein said biological sample is obtained from said subject and provided in said reaction vessel without nucleic acid extraction and purification; and
      (2) subjecting said reaction mixture in said reaction vessel to a plurality of series of primer extension reactions to generate amplified product that is indicative of a presence of said target nucleic acid in said biological sample, each series comprising a plurality of cycles of (i) incubating said reaction mixture under an individual denaturing condition characterized by an individual denaturing temperature and an individual denaturing duration, followed by (ii) incubating said reaction mixture under an individual elongation condition characterized by an individual elongation temperature and an individual elongation duration, wherein an individual series of said plurality of series of primer extension reactions differs from at least one other individual series of said plurality of series of primer extension reactions with respect to denaturing temperature or elongation temperature.

2. The method of claim 1, wherein said target nucleic acid is a ribonucleic acid.

3. The method of claim 1, wherein said reagents are for conducting reverse transcription amplification in parallel with deoxyribonucleic acid amplification.

4. The method of claim 1, wherein, in (1), said biological sample is concentrated or diluted.

5. The method of claim 1, wherein said amplification protocol further comprises subjecting said target nucleic acid to one or more denaturing conditions prior to (2).

6. The method of claim 1, wherein said amplification protocol further comprises subjecting said target nucleic acid to one or more denaturing conditions between a first series and a second series of said plurality of series of primer extension reactions.

7. The method of claim 1, wherein said individual series of said plurality of series of primer extension reactions also differs from at least one other individual series of said plurality of series of primer extension reactions with respect to at least any one of ramping rate between denaturing temperature and elongation temperature, denaturing duration, and elongation duration.

8. The method of claim 1, wherein said plurality of series of primer extension reactions comprises a first series and a second series, each cycle of said first series comprising (i) incubating said reaction mixture at about 92° C.-95° C. for no more than 30 seconds, followed by (ii) incubating said reaction mixture at about 35° C.-65° C. for no more than 1 minute, each cycle of said second series comprising (i) incubating said reaction mixture at about 92° C.-95° C. for no more than 30 seconds, followed by (ii) incubating said reaction mixture at about 40° C.-60° C. for no more than 1 minute.

9. The method of claim 1, further comprising, prior to (2), pre-heating said biological sample at a pre-heating temperature from 90° C. to 100° C. for a pre-heating duration of no more than 10 minutes.

10. The method of claim 1, wherein said individual series of said plurality of series of primer extension reactions differs from at least one other individual series of said plurality of series of primer extension reactions with respect to denaturing temperature and elongation temperature.

11. The method of claim 1, wherein an elongation duration of at least one of said plurality of cycles is less than 90 seconds.

12. A system for amplifying a target nucleic acid in a biological sample obtained from a subject, comprising:
an electronic display screen comprising a user interface that displays a graphical element accessible by a user to execute an amplification protocol to amplify said target nucleic acid in said biological sample; and
an amplification unit comprising one or more computer processors coupled to said electronic display screen and programmed to execute said amplification protocol upon selection of said graphical element by said user, which amplification protocol comprises:
(a) providing a reaction vessel comprising a reaction mixture including said biological sample and reagents for conducting nucleic acid amplification, said reagents comprising (i) a deoxyribonucleic acid (DNA) polymerase and optionally a reverse transcriptase, and (ii) a primer set for said target nucleic acid, wherein said biological sample is obtained from said subject and provided in said reaction vessel without nucleic acid extraction and purification; and
(b) subjecting said reaction mixture in said reaction vessel to a plurality of series of primer extension reactions to generate amplified product that is indicative of a presence of said target nucleic acid in said biological sample, each series comprising a plurality of cycles of (i) incubating said reaction mixture under an individual denaturing condition characterized by an individual denaturing temperature and an individual denaturing duration, followed by (ii) incubating said reaction mixture under an individual elongation condition characterized by an individual elongation temperature and an individual elongation duration, wherein an individual series of said plurality of series of primer extension reactions differs from at least one other individual series of said plurality of series of primer extension reactions with respect to denaturing temperature or elongation temperature.

13. The system of claim 12, wherein said amplification protocol further comprises selecting said primer set for said target nucleic acid.

14. The system of claim 12, wherein said user interface displays a plurality of graphical elements, wherein each of said graphical elements is associated with a given amplification protocol among a plurality of amplification protocols.

15. The system of claim 14, wherein each of said graphical elements is associated with a disease, and wherein a given amplification protocol among said plurality of amplification protocols is directed to assaying a presence of said disease in said subject.

16. The system of claim 15, wherein said disease is associated with a virus.

17. The system of claim 16, wherein said virus is selected from the group consisting of human immunodeficiency virus I (HIV I), human immunodeficiency virus II (HIV II), an orthomyxovirus, Ebola virus, Dengue virus, an influenza virus, hepevirus, hepatitis A virus, hepatitis B virus, hepatitis C virus, hepatitis D virus, hepatitis E virus, hepatitis G virus, Epstein-Barr virus, mononucleosis virus, cytomegalovirus, SARS virus, West Nile Fever virus, polio virus, measles virus, herpes simplex virus, smallpox virus, adenovirus, and Varicella virus.

18. The system of claim 15, wherein said disease is associated with a pathogen.

19. The system of claim 18, wherein said pathogen is *Mycobacterium tuberculosis* or *Plasmodium*.

20. The system of claim 12, wherein said target nucleic acid is associated with a disease.

21. The system of claim 20, wherein said amplification protocol is directed to assaying a presence of said disease based on a presence of said amplified product.

22. The system of claim 12, wherein an elongation duration of at least one of said plurality of cycles is less than 90 seconds.

23. The method of claim 12, wherein said individual series of said plurality of series of primer extension reactions differs from at least one other individual series of said plurality of series of primer extension reactions with respect to denaturing temperature and elongation temperature.

* * * * *

UNITED STATES PATENT AND TRADEMARK OFFICE
CERTIFICATE OF CORRECTION

PATENT NO. : 10,465,239 B2
APPLICATION NO. : 15/372195
DATED : November 5, 2019
INVENTOR(S) : Xiang Li It is certified that error appears in the above-identified patent and that said Letters Patent is hereby corrected as shown below:

In the Claims

At Column 58, Line 61, please change:
"The method of claim 12, wherein said individual series of said plurality of series of primer extension reactions differs from at least one other individual series of said plurality of series of primer extension reactions with respect to denaturing temperature and elongation temperature,"

To:
"The system of claim 12, wherein said individual series of said plurality of series of primer extension reactions differs from at least one other individual series of said plurality of series of primer extension reactions with respect to denaturing temperature and elongation temperature."

Signed and Sealed this
Seventh Day of January, 2020

Andrei Iancu
*Director of the United States Patent and Trademark Office*